(12) United States Patent
Leonard et al.

(10) Patent No.: US 11,998,635 B2
(45) Date of Patent: *Jun. 4, 2024

(54) TARGETED EXTRACELLULAR VESICLES COMPRISING MEMBRANE PROTEINS WITH ENGINEERED GLYCOSYLATION SITES

(71) Applicant: Northwestern University, Evanston, IL (US)

(72) Inventors: Joshua N. Leonard, Wilmette, IL (US); Michelle E. Hung, Chicago, IL (US)

(73) Assignee: Northwestern University, Evanston, IL (US)

(*) Notice: Subject to any disclaimer, the term of this patent is extended or adjusted under 35 U.S.C. 154(b) by 942 days.

This patent is subject to a terminal disclaimer.

(21) Appl. No.: 16/852,894

(22) Filed: Apr. 20, 2020

(65) Prior Publication Data

US 2020/0390700 A1    Dec. 17, 2020

Related U.S. Application Data

(63) Continuation of application No. 15/278,568, filed on Sep. 28, 2016, now Pat. No. 10,624,849.

(60) Provisional application No. 62/233,625, filed on Sep. 28, 2015.

(51) Int. Cl.
| | | |
|---|---|---|
| *A61K 9/107* | (2006.01) | |
| *A61K 9/00* | (2006.01) | |
| *A61K 31/713* | (2006.01) | |
| *A61K 47/46* | (2006.01) | |
| *C07K 14/705* | (2006.01) | |
| *C12N 15/88* | (2006.01) | |

(52) U.S. Cl.
CPC .......... *A61K 9/1075* (2013.01); *A61K 9/0019* (2013.01); *A61K 31/713* (2013.01); *A61K 47/46* (2013.01); *C07K 14/70596* (2013.01); *C12N 15/88* (2013.01); *C07K 2319/03* (2013.01); *C07K 2319/06* (2013.01); *C07K 2319/74* (2013.01); *C07K 2319/85* (2013.01); *C07K 2319/91* (2013.01); *C12N 2740/16043* (2013.01); *C12N 2810/6081* (2013.01)

(58) Field of Classification Search
CPC ............ A61K 31/713; A61K 47/48776; A61K 9/5068; C07K 14/705; C07K 2319/03; C07K 2319/06; C07K 2319/85; C12N 15/85; C12N 15/88; C12N 2795/00022
USPC .................................................... 424/93.21
See application file for complete search history.

(56) References Cited

U.S. PATENT DOCUMENTS

| | | | | |
|---|---|---|---|---|
| 10,624,849 | B2* | 4/2020 | Leonard ................. | A61K 47/46 |
| 2007/0298118 | A1* | 12/2007 | Lotvall ................... | A61P 31/00 |
| | | | | 435/69.3 |
| 2013/0053426 | A1* | 2/2013 | Seow ................... | C07K 14/435 |
| | | | | 514/44 R |
| 2017/0073382 | A1* | 3/2017 | Wong ................... | C12N 5/0619 |

OTHER PUBLICATIONS

Kundra et al. JBC, vol. 274, No. 43, Issue of Oct. 22, pp. 31039-31046, 1999. (Year: 1999).*
Keryer-Bibens et al. Biol Cell, 2008, 100(2): p. 125-38. (Year: 2008).*
Raposo et al. (J. Cell Biol. Vol. 200, No. 4, pp. 373-383) (Year: 2013).*
Zhu et al. Am. J. Cardiovasc. Des. 2011, 1(2):138-149. (Year: 2011).*
Akao, Y., et al., Microvesicle-mediated RNA molecule delivery system using monocytes/macrophages. Mol Ther, 2011. 19(2): p. 395-399.
Alvarez-Erviti, L., et al., Delivery of siRNA to the mouse brain by systemic injection of targeted exosomes. Nat Biotechnol, 2011. 29(4): p. 341-345.
Bano-Polo et al. "N-Glycosylation efficiency is determined by the distance to the C-terminus and the amino acid preceding an Asn-Ser-Thr sequon", Protein Sci., 2011, 20:179-186.
Bolukbasi, M.F., et al., miR-1289 and "Zipcode"—like Sequence Enrich mRNAs in Microvesicles. Mol Ther Nucleic Acids, 2012. 1: p. e10.
Hergenreider, E., et al., Atheroprotective communication between endothelial cells and smooth muscle cells through miRNAs. Nat Cell Biol, 2012. 14(3): p. 249-256.
Hung, et al., "A Platform for Actively Loading Cargo RNA to Elucidate Limiting Steps in EV-Mediated Delivery", Journal of Extracellular Vesicles, 2016, 5: 31027, p. 1-13.
Iguchi, H., N. Kosaka, and T. Ochiya, Secretory microRNAs as a versatile communication too. Commun Integr Biol, 2010. 3(5): p. 478-481.
Johnstone, R.M., et al., Vesicle formation during reticulocyte maturation. Association of plasma membrane activities with released vesicles (exosomes). J Biol Chem, 1987. 262(19): p. 9412-9420.
Keryer-Bibens, C., C. Barreau, and H.B. Osborne, Tethering of proteins to RNAs by bacteriophage proteins. Biol Cell, 2008. 100(2): p. 125-138.
Koppers-Lallic, D.H., M.; van Eijndhoven, M.E.; Sabogal Pineros, Y.; Sie, D.; YIstra, B.; Middeldorp, J.M.; Pegtel, D.M., Comprehensive deep-sequencing analysis reveals non-random small RNA incorporation into tumour exosomes and biomarker potential. Journal of Extracellular Vesicles, 2013. 2: p. 20826.
Kosaka, N., et al., Competitive interactions of cancer cells and normal cells via secretory microRNAs. J Biol Chem, 2012. 287(2): p. 1397-1405.

(Continued)

*Primary Examiner* — Janet L Epps-Smith
(74) *Attorney, Agent, or Firm* — Foley & Lardner LLP

(57) ABSTRACT

Disclosed are extracellular vesicles comprising an engineered targeting protein for targeting the extracellular vesicles to target cells. The targeting protein is a fusion protein that includes a ligand, an engineered glycosylation site, and an exosome-targeting domain. Exemplary extracellular vesicles may include but are not limited to exosomes.

18 Claims, 12 Drawing Sheets

Specification includes a Sequence Listing.

(56) References Cited

OTHER PUBLICATIONS

Kucharzewska, P., et al., Exosomes reflect the hypoxic status of glioma cells and mediate hypoxia-dependent activation of vascular cells during tumor development. Proc Natl Acad Sci U S A, 2013. 110(18): p. 7312-7317.

Kundra et al. "Asparagine-linked oligosaccharides protect Lamp-1 and Lamp-2 from intracellular proteolysis", J. Biol. Chem., 1999, 274:31039-31046.

Mizrak, A., et al., Genetically engineered microvesicles carrying suicide mRNA/protein inhibit schwannoma tumor growth. Mol Ther, 2013. 21(1): p. 101-108.

Montecalvo, A., et al., Mechanism of transfer of functional microRNAs between mouse dendritic cells via exosomes. Blood, 2012. 119(3): p. 756-766.

Ohno, S., et al., Systemically injected exosomes targeted to EGFR deliver antitumor microRNA to breast cancer cells. Mol Ther, 2013. 21(1): p. 185-191.

Raposo et al., J. Cell. Biol., 2013, 200(4):373-383.

Raposo, G., et al., B lymphocytes secrete antigen-presenting vesicles. J Exp Med, 1996. 183(3): p. 1161-1172.

Rechavi, O., et al., Cell contact-dependent acquisition of cellular and viral nonautonomously encoded small RNAs. Genes Dev, 2009. 23(16): p. 1971-1979.

Schulz et al., Chapter 2: Beyond the Sequon: Sites of N-Glycosylation, Biochemistry, Genetics and Molecular Biology "Glycosylation," edited by Stefana Petrescu, Sep. 26, 2012.

Skokos, D., et al., Mast cell-dependent B and T lymphocyte activation is mediated by the secretion of immunologically active exosomes. J Immunol, 2001. 166(2): p. 868-876.

Valadi, H., et al., Exosome-mediated transfer of mRNAs and microRNAs is a novel mechanism of genetic exchange between cells. Nat Cell Biol, 2007. 9(6): p. 654-659.

Zhu et al., Am. J. Cardiovasc. Dis., 2011, 1(2):138-149.

Zitvogel, L., et al., Eradication of established murine tumors using a novel cell-free vaccine: dendritic cell-derived exosomes. Nat Med, 1998. 4(5): p. 594-600.

\* cited by examiner

Figure 3

For displaying proteins on the exosome surface:

N-term | Signal peptide | Protein of Interest | Lamp2b | C-term

For displaying proteins on the exosome lumen:

N-term | Signal peptide | Lamp2b | Protein of Interest | C-term

SEQUENCE LISTING

<160> NUMBER OF SEQ ID NOS: 38

<210> SEQ ID NO 1
<211> LENGTH: 130

```
<212> TYPE: PRT
<213> ORGANISM: Levivirus Bacteriophage MS2

<400> SEQUENCE: 1

Met Ala Ser Asn Phe Thr Gln Phe Val Leu Val Asp Asn Gly Gly Thr
1               5                   10                  15

Gly Asp Val Thr Val Ala Pro Ser Asn Phe Ala Asn Gly Val Ala Glu
            20                  25                  30

Trp Ile Ser Ser Asn Ser Arg Ser Gln Ala Tyr Lys Val Thr Cys Ser
        35                  40                  45

Val Arg Gln Ser Ser Ala Gln Asn Arg Lys Tyr Thr Ile Lys Val Glu
    50                  55                  60

Val Pro Lys Val Ala Thr Gln Thr Val Gly Gly Val Glu Leu Pro Val
65                  70                  75                  80

Ala Ala Trp Arg Ser Tyr Leu Asn Met Glu Leu Thr Ile Pro Ile Phe
                85                  90                  95

Ala Thr Asn Ser Asp Cys Glu Leu Ile Val Lys Ala Met Gln Gly Leu
            100                 105                 110

Leu Lys Asp Gly Asn Pro Ile Pro Ser Ala Ile Ala Ala Asn Ser Gly
        115                 120                 125

Ile Tyr
    130

<210> SEQ ID NO 2
<211> LENGTH: 53
<212> TYPE: PRT
<213> ORGANISM: Levivirus Bacteriophage MS2

<400> SEQUENCE: 2

Tyr Lys Val Thr Cys Ser Val Arg Gln Ser Ser Ala Gln Asn Arg Lys
1               5                   10                  15

Tyr Thr Ile Lys Val Glu Val Pro Lys Val Ala Thr Gln Thr Val Gly
            20                  25                  30

Gly Val Glu Leu Pro Val Ala Ala Trp Arg Ser Tyr Leu Asn Met Glu
        35                  40                  45

Leu Thr Ile Pro Ile
    50

<210> SEQ ID NO 3
<211> LENGTH: 10
<212> TYPE: RNA
<213> ORGANISM: Levivirus Bacteriophage MS2
<220> FEATURE:
<221> NAME/KEY: misc_feature
<222> LOCATION: (1)..(3)
<223> OTHER INFORMATION: n is a, c, g, or u
<220> FEATURE:
<221> NAME/KEY: misc_feature
<222> LOCATION: (8)..(10)
<223> OTHER INFORMATION: n is a, c, g, or u

<400> SEQUENCE: 3 nnnauuannn                                                          10

<210> SEQ ID NO 4
<211> LENGTH: 23
<212> TYPE: RNA
<213> ORGANISM: Levivirus Bacteriophage MS2
<220> FEATURE:
<221> NAME/KEY: misc_feature
<222> LOCATION: (1)..(7)
<223> OTHER INFORMATION: n is a, c, g, or u
```

```
<220> FEATURE:
<221> NAME/KEY: misc_feature
<222> LOCATION: (9)..(10)
<223> OTHER INFORMATION: n is a, c, g, or u
<220> FEATURE:
<221> NAME/KEY: misc_feature
<222> LOCATION: (15)..(23)
<223> OTHER INFORMATION: n is a, c, g, or u

<400> SEQUENCE: 4
nnnnnnnann auuannnnnn nnn                                           23

<210> SEQ ID NO 5
<211> LENGTH: 23
<212> TYPE: RNA
<213> ORGANISM: Levivirus Bacteriophage MS2
<220> FEATURE:
<221> NAME/KEY: misc_feature
<222> LOCATION: (1)..(7)
<223> OTHER INFORMATION: n is a, c, g, or u
<220> FEATURE:
<221> NAME/KEY: misc_feature
<222> LOCATION: (9)..(10)
<223> OTHER INFORMATION: n is a, c, g, or u
<220> FEATURE:
<221> NAME/KEY: misc_feature
<222> LOCATION: (15)..(23)
<223> OTHER INFORMATION: n is a, c, g, or u

<400> SEQUENCE: 5
nnnnnnnann aucannnnnn nnn                                           23

<210> SEQ ID NO 6
<211> LENGTH: 23
<212> TYPE: RNA
<213> ORGANISM: Levivirus Bacteriophage MS2
<220> FEATURE:
<221> NAME/KEY: misc_feature
<222> LOCATION: (1)..(7)
<223> OTHER INFORMATION: n is a, c, g, or u
<220> FEATURE:
<221> NAME/KEY: misc_feature
<222> LOCATION: (9)..(10)
<223> OTHER INFORMATION: n is a, c, g, or u
<220> FEATURE:
<221> NAME/KEY: misc_feature
<222> LOCATION: (15)..(23)
<223> OTHER INFORMATION: n is a, c, g, or u

<400> SEQUENCE: 6
nnnnnnnann acuannnnnn nnn                                           23

<210> SEQ ID NO 7
<211> LENGTH: 23
<212> TYPE: RNA
<213> ORGANISM: Levivirus Bacteriophage MS2

<400> SEQUENCE: 7
aaacaugagg auuacccaug ucg                                           23

<210> SEQ ID NO 8
<211> LENGTH: 23
<212> TYPE: RNA
<213> ORGANISM: Levivirus Bacteriophage MS2

<400> SEQUENCE: 8
aaacaugagg aucacccaug ucg                                           23

<210> SEQ ID NO 9
```

<211> LENGTH: 23
<212> TYPE: RNA
<213> ORGANISM: Levivirus Bacteriophage MS2

<400> SEQUENCE: 9
aaacaugagg acuacccaug ucg                                               23

<210> SEQ ID NO 10
<211> LENGTH: 107
<212> TYPE: PRT
<213> ORGANISM: Enterobacteria phage lambda

<400> SEQUENCE: 10

Met Asp Ala Gln Thr Arg Arg Glu Arg Arg Ala Glu Lys Gln Ala
1               5                   10                  15

Gln Trp Lys Ala Ala Asn Pro Leu Leu Val Gly Val Ser Ala Lys Pro
            20                  25                  30

Val Asn Arg Pro Ile Leu Ser Leu Asn Arg Lys Pro Lys Ser Arg Val
        35                  40                  45

Glu Ser Ala Leu Asn Pro Ile Asp Leu Thr Val Leu Ala Glu Tyr His
    50                  55                  60

Lys Gln Ile Glu Ser Asn Leu Gln Arg Ile Glu Arg Lys Asn Gln Arg
65                  70                  75                  80

Thr Trp Tyr Ser Lys Pro Gly Glu Arg Gly Ile Thr Cys Ser Gly Arg
                85                  90                  95

Gln Lys Ile Lys Gly Lys Ser Ile Pro Leu Ile
            100                 105

<210> SEQ ID NO 11
<211> LENGTH: 100
<212> TYPE: PRT
<213> ORGANISM: Enterobacteria phage P22

<400> SEQUENCE: 11

Met Thr Val Ile Thr Tyr Gly Lys Ser Thr Phe Ala Gly Asn Ala Lys
1               5                   10                  15

Thr Arg Arg His Glu Arg Arg Arg Lys Leu Ala Ile Glu Arg Asp Thr
            20                  25                  30

Ile Cys Asn Ile Ile Asp Ser Ile Phe Gly Cys Asp Ala Pro Asp Ala
        35                  40                  45

Ser Gln Glu Val Lys Ala Lys Arg Ile Asp Arg Val Thr Lys Ala Ile
    50                  55                  60

Ser Leu Ala Gly Thr Arg Gln Lys Glu Val Glu Gly Gly Ser Val Leu
65                  70                  75                  80

Leu Pro Gly Val Ala Leu Tyr Ala Ala Gly His Arg Lys Ser Lys Gln
                85                  90                  95

Ile Thr Ala Arg
            100

<210> SEQ ID NO 12
<211> LENGTH: 99
<212> TYPE: PRT
<213> ORGANISM: Enterobacteria phage Phi21

<400> SEQUENCE: 12

Met Val Thr Ile Val Trp Lys Glu Ser Lys Gly Thr Ala Lys Ser Arg
1               5                   10                  15

Tyr Lys Ala Arg Arg Ala Glu Leu Ile Ala Glu Arg Arg Ser Asn Glu
            20                  25                  30

```
Ala Leu Ala Arg Lys Ile Ala Leu Lys Leu Ser Gly Cys Val Arg Ala
         35                  40                  45

Asp Lys Ala Ala Ser Leu Gly Ser Leu Arg Cys Lys Ala Glu Glu
     50                  55                  60

Val Glu Arg Lys Gln Asn Arg Ile Tyr Tyr Ser Lys Pro Arg Ser Glu
 65                  70                  75                  80

Met Gly Val Thr Cys Val Gly Arg Gln Lys Ile Lys Leu Gly Ser Lys
                 85                  90                  95

Pro Leu Ile

<210> SEQ ID NO 13
<211> LENGTH: 21
<212> TYPE: PRT
<213> ORGANISM: Enterobacteria phage lambda

<400> SEQUENCE: 13

Asp Ala Gln Thr Arg Arg Arg Glu Arg Arg Ala Glu Lys Gln Ala Gln
 1               5                  10                  15

Trp Lys Ala Ala Asn
             20

<210> SEQ ID NO 14
<211> LENGTH: 25
<212> TYPE: PRT
<213> ORGANISM: Enterobacteria phage P22

<400> SEQUENCE: 14

Lys Ser Thr Phe Ala Gly Asn Ala Lys Thr Arg Arg His Glu Arg Arg
 1               5                  10                  15

Arg Lys Leu Ala Ile Glu Arg Asp Thr
             20                  25

<210> SEQ ID NO 15
<211> LENGTH: 22
<212> TYPE: PRT
<213> ORGANISM: Enterobacteria phage Phi21

<400> SEQUENCE: 15

Glu Ser Lys Gly Thr Ala Lys Ser Arg Tyr Lys Ala Arg Arg Ala Glu
 1               5                  10                  15

Leu Ile Ala Glu Arg Arg
             20

<210> SEQ ID NO 16
<211> LENGTH: 15
<212> TYPE: RNA
<213> ORGANISM: Enterobacteria phage lambda

<400> SEQUENCE: 16
gcccugaaga agggc                                                15

<210> SEQ ID NO 17
<211> LENGTH: 15
<212> TYPE: RNA
<213> ORGANISM: Enterobacteria phage lambda

<400> SEQUENCE: 17
gcccugaaaa agggc                                                15

<210> SEQ ID NO 18
```

```
<211> LENGTH: 15
<212> TYPE: RNA
<213> ORGANISM: Enterobacteria phage P22

<400> SEQUENCE: 18
gcgcugacaa agcgc                                                    15

<210> SEQ ID NO 19
<211> LENGTH: 20
<212> TYPE: RNA
<213> ORGANISM: Enterobacteria phage Phi21

<400> SEQUENCE: 19
uucaccucua accgggugag                                               20

<210> SEQ ID NO 20
<211> LENGTH: 410
<212> TYPE: PRT
<213> ORGANISM: Homo sapiens

<400> SEQUENCE: 20
```

| | | | | | | | | | | | | | | | |
|---|---|---|---|---|---|---|---|---|---|---|---|---|---|---|---|
| Met | Val | Cys | Phe | Arg | Leu | Phe | Pro | Val | Pro | Gly | Ser | Gly | Leu | Val | Leu |
| 1 | | | | 5 | | | | | 10 | | | | | 15 | |
| Val | Cys | Leu | Val | Leu | Gly | Ala | Val | Arg | Ser | Tyr | Ala | Leu | Glu | Leu | Asn |
| | | | 20 | | | | | 25 | | | | | 30 | | |
| Leu | Thr | Asp | Ser | Glu | Asn | Ala | Thr | Cys | Leu | Tyr | Ala | Lys | Trp | Gln | Met |
| | | 35 | | | | | 40 | | | | | 45 | | | |
| Asn | Phe | Thr | Val | Arg | Tyr | Glu | Thr | Thr | Asn | Lys | Thr | Tyr | Lys | Thr | Val |
| | 50 | | | | | 55 | | | | | 60 | | | | |
| Thr | Ile | Ser | Asp | His | Gly | Thr | Val | Thr | Tyr | Asn | Gly | Ser | Ile | Cys | Gly |
| 65 | | | | | 70 | | | | | 75 | | | | | 80 |
| Asp | Asp | Gln | Asn | Gly | Pro | Lys | Ile | Ala | Val | Gln | Phe | Gly | Pro | Gly | Phe |
| | | | | 85 | | | | | 90 | | | | | 95 | |
| Ser | Trp | Ile | Ala | Asn | Phe | Thr | Lys | Ala | Ala | Ser | Thr | Tyr | Ser | Ile | Asp |
| | | | 100 | | | | | 105 | | | | | 110 | | |
| Ser | Val | Ser | Phe | Ser | Tyr | Asn | Thr | Gly | Asp | Asn | Thr | Thr | Phe | Pro | Asp |
| | | | 115 | | | | | 120 | | | | | 125 | | |
| Ala | Glu | Asp | Lys | Gly | Ile | Leu | Thr | Val | Asp | Glu | Leu | Leu | Ala | Ile | Arg |
| | 130 | | | | | 135 | | | | | 140 | | | | |
| Ile | Pro | Leu | Asn | Asp | Leu | Phe | Arg | Cys | Asn | Ser | Leu | Ser | Thr | Leu | Glu |
| 145 | | | | | 150 | | | | | 155 | | | | | 160 |
| Lys | Asn | Asp | Val | Val | Gln | His | Tyr | Trp | Asp | Val | Leu | Val | Gln | Ala | Phe |
| | | | | 165 | | | | | 170 | | | | | 175 | |
| Val | Gln | Asn | Gly | Thr | Val | Ser | Thr | Asn | Glu | Phe | Leu | Cys | Asp | Lys | Asp |
| | | | 180 | | | | | 185 | | | | | 190 | | |
| Lys | Thr | Ser | Thr | Val | Ala | Pro | Thr | Ile | His | Thr | Thr | Val | Pro | Ser | Pro |
| | | | 195 | | | | | 200 | | | | | 205 | | |
| Thr | Thr | Thr | Pro | Thr | Pro | Lys | Glu | Lys | Pro | Glu | Ala | Gly | Thr | Tyr | Ser |
| | 210 | | | | | 215 | | | | | 220 | | | | |
| Val | Asn | Asn | Gly | Asn | Asp | Thr | Cys | Leu | Leu | Ala | Thr | Met | Gly | Leu | Gln |
| 225 | | | | | 230 | | | | | 235 | | | | | 240 |
| Leu | Asn | Ile | Thr | Gln | Asp | Lys | Val | Ala | Ser | Val | Ile | Asn | Ile | Asn | Pro |
| | | | | 245 | | | | | 250 | | | | | 255 | |
| Asn | Thr | Thr | His | Ser | Thr | Gly | Ser | Cys | Arg | Ser | His | Thr | Ala | Leu | Leu |
| | | | 260 | | | | | 265 | | | | | 270 | | |
| Arg | Leu | Asn | Ser | Ser | Thr | Ile | Lys | Tyr | Leu | Asp | Phe | Val | Phe | Ala | Val |
| | | | 275 | | | | | 280 | | | | | 285 | | |

-continued

Lys Asn Glu Asn Arg Phe Tyr Leu Lys Glu Val Asn Ile Ser Met Tyr
        290                 295                 300

Leu Val Asn Gly Ser Val Phe Ser Ile Ala Asn Asn Leu Ser Tyr
305                 310                 315                 320

Trp Asp Ala Pro Leu Gly Ser Ser Tyr Met Cys Asn Lys Glu Gln Thr
                325                 330                 335

Val Ser Val Ser Gly Ala Phe Gln Ile Asn Thr Phe Asp Leu Arg Val
            340                 345                 350

Gln Pro Phe Asn Val Thr Gln Gly Lys Tyr Ser Thr Ala Gln Asp Cys
        355                 360                 365

Ser Ala Asp Asp Asp Asn Phe Leu Val Pro Ile Ala Val Gly Ala Ala
370                 375                 380

Leu Ala Gly Val Leu Ile Leu Val Leu Leu Ala Tyr Phe Ile Gly Leu
385                 390                 395                 400

Lys His His His Ala Gly Tyr Glu Gln Phe
                405                 410

<210> SEQ ID NO 21
<211> LENGTH: 410
<212> TYPE: PRT
<213> ORGANISM: Homo sapiens

<400> SEQUENCE: 21

Met Val Cys Phe Arg Leu Phe Pro Val Pro Gly Ser Gly Leu Val Leu
1               5                   10                  15

Val Cys Leu Val Leu Gly Ala Val Arg Ser Tyr Ala Leu Glu Leu Asn
                20                  25                  30

Leu Thr Asp Ser Glu Asn Ala Thr Cys Leu Tyr Ala Lys Trp Gln Met
            35                  40                  45

Asn Phe Thr Val Arg Tyr Glu Thr Thr Asn Lys Thr Tyr Lys Thr Val
        50                  55                  60

Thr Ile Ser Asp His Gly Thr Val Thr Tyr Asn Gly Ser Ile Cys Gly
65                  70                  75                  80

Asp Asp Gln Asn Gly Pro Lys Ile Ala Val Gln Phe Gly Pro Gly Phe
                85                  90                  95

Ser Trp Ile Ala Asn Phe Thr Lys Ala Ala Ser Thr Tyr Ser Ile Asp
            100                 105                 110

Ser Val Ser Phe Ser Tyr Asn Thr Gly Asp Asn Thr Thr Phe Pro Asp
        115                 120                 125

Ala Glu Asp Lys Gly Ile Leu Thr Val Asp Glu Leu Leu Ala Ile Arg
    130                 135                 140

Ile Pro Leu Asn Asp Leu Phe Arg Cys Asn Ser Leu Ser Thr Leu Glu
145                 150                 155                 160

Lys Asn Asp Val Val Gln His Tyr Trp Asp Val Leu Val Gln Ala Phe
                165                 170                 175

Val Gln Asn Gly Thr Val Ser Thr Asn Glu Phe Leu Cys Asp Lys Asp
            180                 185                 190

Lys Thr Ser Thr Val Ala Pro Thr Ile His Thr Thr Val Pro Ser Pro
        195                 200                 205

Thr Thr Thr Pro Thr Pro Lys Glu Lys Pro Glu Ala Gly Thr Tyr Ser
    210                 215                 220

Val Asn Asn Gly Asn Asp Thr Cys Leu Leu Ala Thr Met Gly Leu Gln
225                 230                 235                 240

Leu Asn Ile Thr Gln Asp Lys Val Ala Ser Val Ile Asn Ile Asn Pro

-continued

```
                    245                 250                 255
Asn Thr Thr His Ser Thr Gly Ser Cys Arg Ser His Thr Ala Leu Leu
                260                 265                 270

Arg Leu Asn Ser Ser Thr Ile Lys Tyr Leu Asp Phe Val Phe Ala Val
            275                 280                 285

Lys Asn Glu Asn Arg Phe Tyr Leu Lys Glu Val Asn Ile Ser Met Tyr
        290                 295                 300

Leu Val Asn Gly Ser Val Phe Ser Ile Ala Asn Asn Asn Leu Ser Tyr
    305                 310                 315                 320

Trp Asp Ala Pro Leu Gly Ser Ser Tyr Met Cys Asn Lys Glu Gln Thr
                325                 330                 335

Val Ser Val Ser Gly Ala Phe Gln Ile Asn Thr Phe Asp Leu Arg Val
            340                 345                 350

Gln Pro Phe Asn Val Thr Gln Gly Lys Tyr Ser Thr Ala Gln Glu Cys
        355                 360                 365

Ser Leu Asp Asp Asp Thr Ile Leu Ile Pro Ile Ile Val Gly Ala Gly
    370                 375                 380

Leu Ser Gly Leu Ile Ile Val Ile Val Ile Ala Tyr Val Ile Gly Arg
385                 390                 395                 400

Arg Lys Ser Tyr Ala Gly Tyr Gln Thr Leu
                405                 410

<210> SEQ ID NO 22
<211> LENGTH: 411
<212> TYPE: PRT
<213> ORGANISM: Homo sapiens

<400> SEQUENCE: 22

Met Val Cys Phe Arg Leu Phe Pro Val Pro Gly Ser Gly Leu Val Leu
1               5                   10                  15

Val Cys Leu Val Leu Gly Ala Val Arg Ser Tyr Ala Leu Glu Leu Asn
            20                  25                  30

Leu Thr Asp Ser Glu Asn Ala Thr Cys Leu Tyr Ala Lys Trp Gln Met
        35                  40                  45

Asn Phe Thr Val Arg Tyr Glu Thr Thr Asn Lys Thr Tyr Lys Thr Val
    50                  55                  60

Thr Ile Ser Asp His Gly Thr Val Thr Tyr Asn Gly Ser Ile Cys Gly
65                  70                  75                  80

Asp Asp Gln Asn Gly Pro Lys Ile Ala Val Gln Phe Gly Pro Gly Phe
                85                  90                  95

Ser Trp Ile Ala Asn Phe Thr Lys Ala Ala Ser Thr Tyr Ser Ile Asp
            100                 105                 110

Ser Val Ser Phe Ser Tyr Asn Thr Gly Asp Asn Thr Thr Phe Pro Asp
        115                 120                 125

Ala Glu Asp Lys Gly Ile Leu Thr Val Asp Glu Leu Leu Ala Ile Arg
    130                 135                 140

Ile Pro Leu Asn Asp Leu Phe Arg Cys Asn Ser Leu Ser Thr Leu Glu
145                 150                 155                 160

Lys Asn Asp Val Val Gln His Tyr Trp Asp Val Leu Val Gln Ala Phe
                165                 170                 175

Val Gln Asn Gly Thr Val Ser Thr Asn Glu Phe Leu Cys Asp Lys Asp
            180                 185                 190

Lys Thr Ser Thr Val Ala Pro Thr Ile His Thr Thr Val Pro Ser Pro
        195                 200                 205
```

```
Thr Thr Thr Pro Thr Pro Lys Glu Lys Pro Glu Ala Gly Thr Tyr Ser
            210                 215                 220

Val Asn Asn Gly Asn Asp Thr Cys Leu Leu Ala Thr Met Gly Leu Gln
225                 230                 235                 240

Leu Asn Ile Thr Gln Asp Lys Val Ala Ser Val Ile Asn Ile Asn Pro
                245                 250                 255

Asn Thr Thr His Ser Thr Gly Ser Cys Arg Ser His Thr Ala Leu Leu
                260                 265                 270

Arg Leu Asn Ser Ser Thr Ile Lys Tyr Leu Asp Phe Val Phe Ala Val
                275                 280                 285

Lys Asn Glu Asn Arg Phe Tyr Leu Lys Glu Val Asn Ile Ser Met Tyr
290                 295                 300

Leu Val Asn Gly Ser Val Phe Ser Ile Ala Asn Asn Asn Leu Ser Tyr
305                 310                 315                 320

Trp Asp Ala Pro Leu Gly Ser Ser Tyr Met Cys Asn Lys Glu Gln Thr
                325                 330                 335

Val Ser Val Ser Gly Ala Phe Gln Ile Asn Thr Phe Asp Leu Arg Val
                340                 345                 350

Gln Pro Phe Asn Val Thr Gln Gly Lys Tyr Ser Thr Ala Glu Glu Cys
                355                 360                 365

Ser Ala Asp Ser Asp Leu Asn Phe Leu Ile Pro Val Ala Val Gly Val
370                 375                 380

Ala Leu Gly Phe Leu Ile Ile Val Val Phe Ile Ser Tyr Met Ile Gly
385                 390                 395                 400

Arg Arg Lys Ser Arg Thr Gly Tyr Gln Ser Val
                405                 410

<210> SEQ ID NO 23
<211> LENGTH: 10
<212> TYPE: PRT
<213> ORGANISM: Homo sapiens

<400> SEQUENCE: 23

Lys His His His Ala Gly Tyr Glu Gln Phe
1               5                   10

<210> SEQ ID NO 24
<211> LENGTH: 11
<212> TYPE: PRT
<213> ORGANISM: Homo sapiens

<400> SEQUENCE: 24

Arg Arg Lys Ser Tyr Ala Gly Tyr Gln Thr Leu
1               5                   10

<210> SEQ ID NO 25
<211> LENGTH: 11
<212> TYPE: PRT
<213> ORGANISM: Homo sapiens

<400> SEQUENCE: 25

Arg Arg Lys Ser Arg Thr Gly Tyr Gln Ser Val
1               5                   10

<210> SEQ ID NO 26
<211> LENGTH: 417
<212> TYPE: PRT
<213> ORGANISM: Homo sapiens

<400> SEQUENCE: 26
```

```
Met Ala Ala Pro Gly Ser Ala Arg Arg Pro Leu Leu Leu Leu Leu
1               5                   10                  15

Leu Leu Leu Leu Gly Leu Met His Cys Ala Ser Ala Ala Met Phe Met
        20                  25                  30

Val Lys Asn Gly Asn Gly Thr Ala Cys Ile Met Ala Asn Phe Ser Ala
        35                  40                  45

Ala Phe Ser Val Asn Tyr Asp Thr Lys Ser Gly Pro Lys Asn Met Thr
50                  55                  60

Phe Asp Leu Pro Ser Asp Ala Thr Val Val Leu Asn Arg Ser Ser Cys
65                  70                  75                  80

Gly Lys Glu Asn Thr Ser Asp Pro Ser Leu Val Ile Ala Phe Gly Arg
                85                  90                  95

Gly His Thr Leu Thr Leu Asn Phe Thr Arg Asn Ala Thr Arg Tyr Ser
                100                 105                 110

Val Gln Leu Met Ser Phe Val Tyr Asn Leu Ser Asp Thr His Leu Phe
                115                 120                 125

Pro Asn Ala Ser Ser Lys Glu Ile Lys Thr Val Glu Ser Ile Thr Asp
        130                 135                 140

Ile Arg Ala Asp Ile Asp Lys Lys Tyr Arg Cys Val Ser Gly Thr Gln
145                 150                 155                 160

Val His Met Asn Asn Val Thr Val Thr Leu His Asp Ala Thr Ile Gln
                165                 170                 175

Ala Tyr Leu Ser Asn Ser Ser Phe Ser Arg Gly Glu Thr Arg Cys Glu
                180                 185                 190

Gln Asp Arg Pro Ser Pro Thr Thr Ala Pro Pro Ala Pro Pro Ser Pro
                195                 200                 205

Ser Pro Ser Pro Val Pro Lys Ser Pro Ser Val Asp Lys Tyr Asn Val
210                 215                 220

Ser Gly Thr Asn Gly Thr Cys Leu Leu Ala Ser Met Gly Leu Gln Leu
225                 230                 235                 240

Asn Leu Thr Tyr Glu Arg Lys Asp Asn Thr Thr Val Thr Arg Leu Leu
                245                 250                 255

Asn Ile Asn Pro Asn Lys Thr Ser Ala Ser Gly Ser Cys Gly Ala His
                260                 265                 270

Leu Val Thr Leu Glu Leu His Ser Glu Gly Thr Thr Val Leu Leu Phe
                275                 280                 285

Gln Phe Gly Met Asn Ala Ser Ser Arg Phe Phe Leu Gln Gly Ile
                290                 295                 300

Gln Leu Asn Thr Ile Leu Pro Asp Ala Arg Asp Pro Ala Phe Lys Ala
305                 310                 315                 320

Ala Asn Gly Ser Leu Arg Ala Leu Gln Ala Thr Val Gly Asn Ser Tyr
                325                 330                 335

Lys Cys Asn Ala Glu Glu His Val Arg Val Thr Lys Ala Phe Ser Val
                340                 345                 350

Asn Ile Phe Lys Val Trp Val Gln Ala Phe Lys Val Glu Gly Gly Gln
                355                 360                 365

Phe Gly Ser Val Glu Glu Cys Leu Leu Asp Glu Asn Ser Met Leu Ile
                370                 375                 380

Pro Ile Ala Val Gly Gly Ala Leu Ala Gly Leu Val Leu Ile Val Leu
385                 390                 395                 400

Ile Ala Tyr Leu Val Gly Arg Lys Arg Ser His Ala Gly Tyr Gln Thr
                405                 410                 415
```

Ile

<210> SEQ ID NO 27
<211> LENGTH: 11
<212> TYPE: PRT
<213> ORGANISM: Homo sapiens

<400> SEQUENCE: 27

Arg Lys Arg Ser His Ala Gly Tyr Gln Thr Ile
1               5                   10

<210> SEQ ID NO 28
<211> LENGTH: 238
<212> TYPE: PRT
<213> ORGANISM: Homo sapiens

<400> SEQUENCE: 28

Met Ala Val Glu Gly Gly Met Lys Cys Val Lys Phe Leu Leu Tyr Val
1               5                   10                  15

Leu Leu Leu Ala Phe Cys Ala Cys Ala Val Gly Leu Ile Ala Val Gly
                20                  25                  30

Val Gly Ala Gln Leu Val Leu Ser Gln Thr Ile Ile Gln Gly Ala Thr
            35                  40                  45

Pro Gly Ser Leu Leu Pro Val Val Ile Ile Ala Val Gly Val Phe Leu
        50                  55                  60

Phe Leu Val Ala Phe Val Gly Cys Cys Gly Ala Cys Lys Glu Asn Tyr
65                  70                  75                  80

Cys Leu Met Ile Thr Phe Ala Ile Phe Leu Ser Leu Ile Met Leu Val
                85                  90                  95

Glu Val Ala Ala Ala Ile Ala Gly Tyr Val Phe Arg Asp Lys Val Met
                100                 105                 110

Ser Glu Phe Asn Asn Asn Phe Arg Gln Gln Met Glu Asn Tyr Pro Lys
            115                 120                 125

Asn Asn His Thr Ala Ser Ile Leu Asp Arg Met Gln Ala Asp Phe Lys
        130                 135                 140

Cys Cys Gly Ala Ala Asn Tyr Thr Asp Trp Glu Lys Ile Pro Ser Met
145                 150                 155                 160

Ser Lys Asn Arg Val Pro Asp Ser Cys Cys Ile Asn Val Thr Val Gly
                165                 170                 175

Cys Gly Ile Asn Phe Asn Glu Lys Ala Ile His Lys Glu Gly Cys Val
                180                 185                 190

Glu Lys Ile Gly Gly Trp Leu Arg Lys Asn Val Leu Val Val Ala Ala
            195                 200                 205

Ala Ala Leu Gly Ile Ala Phe Val Glu Val Leu Gly Ile Val Phe Ala
        210                 215                 220

Cys Cys Leu Val Lys Ser Ile Arg Ser Gly Tyr Glu Val Met
225                 230                 235

<210> SEQ ID NO 29
<211> LENGTH: 215
<212> TYPE: PRT
<213> ORGANISM: Homo sapiens

<400> SEQUENCE: 29

Met Ala Val Glu Gly Gly Met Lys Cys Val Lys Phe Leu Leu Tyr Val
1               5                   10                  15

Leu Leu Leu Ala Phe Cys Gly Ala Thr Pro Gly Ser Leu Leu Pro Val
                20                  25                  30

```
Val Ile Ile Ala Val Gly Val Phe Leu Phe Leu Val Ala Phe Val Gly
             35                  40                  45

Cys Cys Gly Ala Cys Lys Glu Asn Tyr Cys Leu Met Ile Thr Phe Ala
         50                  55                  60

Ile Phe Leu Ser Leu Ile Met Leu Val Glu Val Ala Ala Ala Ile Ala
 65                  70                  75                  80

Gly Tyr Val Phe Arg Asp Lys Val Met Ser Glu Phe Asn Asn Asn Phe
                 85                  90                  95

Arg Gln Gln Met Glu Asn Tyr Pro Lys Asn Asn His Thr Ala Ser Ile
            100                 105                 110

Leu Asp Arg Met Gln Ala Asp Phe Lys Cys Cys Gly Ala Ala Asn Tyr
            115                 120                 125

Thr Asp Trp Glu Lys Ile Pro Ser Met Ser Lys Asn Arg Val Pro Asp
            130                 135                 140

Ser Cys Cys Ile Asn Val Thr Val Gly Cys Gly Ile Asn Phe Asn Glu
145                 150                 155                 160

Lys Ala Ile His Lys Glu Gly Cys Val Glu Lys Ile Gly Gly Trp Leu
                165                 170                 175

Arg Lys Asn Val Leu Val Val Ala Ala Ala Leu Gly Ile Ala Phe
            180                 185                 190

Val Glu Val Leu Gly Ile Val Phe Ala Cys Cys Leu Val Lys Ser Ile
                195                 200                 205

Arg Ser Gly Tyr Glu Val Met
        210                 215

<210> SEQ ID NO 30
<211> LENGTH: 166
<212> TYPE: PRT
<213> ORGANISM: Homo sapiens

<400> SEQUENCE: 30

Cys Gly Ala Cys Lys Glu Asn Tyr Cys Leu Met Ile Thr Phe Ala Ile
  1               5                  10                  15

Phe Leu Ser Leu Ile Met Leu Val Glu Val Ala Ala Ala Ile Ala Gly
                 20                  25                  30

Tyr Val Phe Arg Asp Lys Val Met Ser Glu Phe Asn Asn Asn Phe Arg
             35                  40                  45

Gln Gln Met Glu Asn Tyr Pro Lys Asn Asn His Thr Ala Ser Ile Leu
         50                  55                  60

Asp Arg Met Gln Ala Asp Phe Lys Cys Cys Gly Ala Ala Asn Tyr Thr
 65                  70                  75                  80

Asp Trp Glu Lys Ile Pro Ser Met Ser Lys Asn Arg Val Pro Asp Ser
                 85                  90                  95

Cys Cys Ile Asn Val Thr Val Gly Cys Gly Ile Asn Phe Asn Glu Lys
            100                 105                 110

Ala Ile His Lys Glu Gly Cys Val Glu Lys Ile Gly Gly Trp Leu Arg
            115                 120                 125

Lys Asn Val Leu Val Val Ala Ala Ala Leu Gly Ile Ala Phe Val
            130                 135                 140

Glu Val Leu Gly Ile Val Phe Ala Cys Cys Leu Val Lys Ser Ile Arg
145                 150                 155                 160

Ser Gly Tyr Glu Val Met
                165
```

```
<210> SEQ ID NO 31
<211> LENGTH: 14
<212> TYPE: PRT
<213> ORGANISM: Homo sapiens

<400> SEQUENCE: 31

Cys Cys Leu Val Lys Ser Ile Arg Ser Gly Tyr Glu Val Met
1               5                   10

<210> SEQ ID NO 32
<211> LENGTH: 478
<212> TYPE: PRT
<213> ORGANISM: Homo sapiens

<400> SEQUENCE: 32

Met Gly Arg Cys Cys Phe Tyr Thr Ala Gly Thr Leu Ser Leu Leu
1               5                   10                  15

Leu Val Thr Ser Val Thr Leu Leu Val Ala Arg Val Phe Gln Lys Ala
                20                  25                  30

Val Asp Gln Ser Ile Glu Lys Lys Ile Val Leu Arg Asn Gly Thr Glu
            35                  40                  45

Ala Phe Asp Ser Trp Glu Lys Pro Pro Leu Pro Val Tyr Thr Gln Phe
        50                  55                  60

Tyr Phe Phe Asn Val Thr Asn Pro Glu Glu Ile Leu Arg Gly Glu Thr
65                  70                  75                  80

Pro Arg Val Glu Glu Val Gly Pro Tyr Thr Tyr Arg Glu Leu Arg Asn
                    85                  90                  95

Lys Ala Asn Ile Gln Phe Gly Asp Asn Gly Thr Thr Ile Ser Ala Val
            100                 105                 110

Ser Asn Lys Ala Tyr Val Phe Glu Arg Asp Gln Ser Val Gly Asp Pro
        115                 120                 125

Lys Ile Asp Leu Ile Arg Thr Leu Asn Ile Pro Val Leu Thr Val Ile
130                 135                 140

Glu Trp Ser Gln Val His Phe Leu Arg Glu Ile Ile Glu Ala Met Leu
145                 150                 155                 160

Lys Ala Tyr Gln Gln Lys Leu Phe Val Thr His Thr Val Asp Glu Leu
                    165                 170                 175

Leu Trp Gly Tyr Lys Asp Glu Ile Leu Ser Leu Ile His Val Phe Arg
                180                 185                 190

Pro Asp Ile Ser Pro Tyr Phe Gly Leu Phe Tyr Glu Lys Asn Gly Thr
            195                 200                 205

Asn Asp Gly Asp Tyr Val Phe Leu Thr Gly Glu Asp Ser Tyr Leu Asn
        210                 215                 220

Phe Thr Lys Ile Val Glu Trp Asn Gly Lys Thr Ser Leu Asp Trp Trp
225                 230                 235                 240

Ile Thr Asp Lys Cys Asn Met Ile Asn Gly Thr Asp Gly Asp Ser Phe
                245                 250                 255

His Pro Leu Ile Thr Lys Asp Glu Val Leu Tyr Val Phe Pro Ser Asp
            260                 265                 270

Phe Cys Arg Ser Val Tyr Ile Thr Phe Ser Asp Tyr Glu Ser Val Gln
        275                 280                 285

Gly Leu Pro Ala Phe Arg Tyr Lys Val Pro Ala Glu Ile Leu Ala Asn
    290                 295                 300

Thr Ser Asp Asn Ala Gly Phe Cys Ile Pro Glu Gly Asn Cys Leu Gly
305                 310                 315                 320

Ser Gly Val Leu Asn Val Ser Ile Cys Lys Asn Gly Ala Pro Ile Ile
```

```
            325                 330                 335
Met Ser Phe Pro His Phe Tyr Gln Ala Asp Glu Arg Phe Val Ser Ala
            340                 345                 350

Ile Glu Gly Met His Pro Asn Gln Glu Asp His Glu Thr Phe Val Asp
            355                 360                 365

Ile Asn Pro Leu Thr Gly Ile Ile Leu Lys Ala Ala Lys Arg Phe Gln
            370                 375                 380

Ile Asn Ile Tyr Val Lys Lys Leu Asp Asp Phe Val Glu Thr Gly Asp
385                 390                 395                 400

Ile Arg Thr Met Val Phe Pro Val Met Tyr Leu Asn Glu Ser Val His
                    405                 410                 415

Ile Asp Lys Glu Thr Ala Ser Arg Leu Lys Ser Met Ile Asn Thr Thr
                    420                 425                 430

Leu Ile Ile Thr Asn Ile Pro Tyr Ile Ile Met Ala Leu Gly Val Phe
                    435                 440                 445

Phe Gly Leu Val Phe Thr Trp Leu Ala Cys Lys Gly Gln Gly Ser Met
            450                 455                 460

Asp Glu Gly Thr Ala Asp Glu Arg Ala Pro Leu Ile Arg Thr
465                 470                 475

<210> SEQ ID NO 33
<211> LENGTH: 335
<212> TYPE: PRT
<213> ORGANISM: Homo sapiens

<400> SEQUENCE: 33

Met Gly Arg Cys Cys Phe Tyr Thr Ala Gly Thr Leu Ser Leu Leu Leu
1               5                   10                  15

Leu Val Thr Ser Val Thr Leu Leu Val Ala Arg Val Phe Gln Lys Ala
            20                  25                  30

Val Asp Gln Ser Ile Glu Lys Lys Ile Val Leu Arg Asn Gly Thr Glu
        35                  40                  45

Ala Phe Asp Ser Trp Glu Lys Pro Leu Pro Val Tyr Thr Gln Phe
    50                  55                  60

Tyr Phe Phe Asn Val Thr Asn Pro Glu Glu Ile Leu Arg Gly Glu Thr
65                  70                  75                  80

Pro Arg Val Glu Glu Val Gly Pro Tyr Thr Tyr Arg Ser Leu Asp Trp
                    85                  90                  95

Trp Ile Thr Asp Lys Cys Asn Met Ile Asn Gly Thr Asp Gly Asp Ser
            100                 105                 110

Phe His Pro Leu Ile Thr Lys Asp Glu Val Leu Tyr Val Phe Pro Ser
            115                 120                 125

Asp Phe Cys Arg Ser Val Tyr Ile Thr Phe Ser Asp Tyr Glu Ser Val
    130                 135                 140

Gln Gly Leu Pro Ala Phe Arg Tyr Lys Val Pro Ala Glu Ile Leu Ala
145                 150                 155                 160

Asn Thr Ser Asp Asn Ala Gly Phe Cys Ile Pro Glu Gly Asn Cys Leu
                    165                 170                 175

Gly Ser Gly Val Leu Asn Val Ser Ile Cys Lys Asn Gly Ala Pro Ile
            180                 185                 190

Ile Met Ser Phe Pro His Phe Tyr Gln Ala Asp Glu Arg Phe Val Ser
            195                 200                 205

Ala Ile Glu Gly Met His Pro Asn Gln Glu Asp His Glu Thr Phe Val
    210                 215                 220
```

```
Asp Ile Asn Pro Leu Thr Gly Ile Ile Leu Lys Ala Ala Lys Arg Phe
225                 230                 235                 240

Gln Ile Asn Ile Tyr Val Lys Lys Leu Asp Asp Phe Val Glu Thr Gly
            245                 250                 255

Asp Ile Arg Thr Met Val Phe Pro Val Met Tyr Leu Asn Glu Ser Val
        260                 265                 270

His Ile Asp Lys Glu Thr Ala Ser Arg Leu Lys Ser Met Ile Asn Thr
    275                 280                 285

Thr Leu Ile Ile Thr Asn Ile Pro Tyr Ile Ile Met Ala Leu Gly Val
290                 295                 300

Phe Phe Gly Leu Val Phe Thr Trp Leu Ala Cys Lys Gly Gln Gly Ser
305                 310                 315                 320

Met Asp Glu Gly Thr Ala Asp Glu Arg Ala Pro Leu Ile Arg Thr
            325                 330                 335

<210> SEQ ID NO 34
<211> LENGTH: 19
<212> TYPE: PRT
<213> ORGANISM: Homo sapiens

<400> SEQUENCE: 34

Gly Gln Gly Ser Met Asp Glu Gly Thr Ala Asp Glu Arg Ala Pro Leu
1               5                   10                  15

Ile Arg Thr

<210> SEQ ID NO 35
<211> LENGTH: 156
<212> TYPE: PRT
<213> ORGANISM: Homo sapiens

<400> SEQUENCE: 35

Met Ile Thr Phe Ala Ile Phe Leu Ser Leu Ile Met Leu Val Glu Val
1               5                   10                  15

Ala Ala Ala Ile Ala Gly Tyr Val Phe Arg Asp Lys Val Met Ser Glu
            20                  25                  30

Phe Asn Asn Asn Phe Arg Gln Gln Met Glu Asn Tyr Pro Lys Asn Asn
        35                  40                  45

His Thr Ala Ser Ile Leu Asp Arg Met Gln Ala Asp Phe Lys Cys Cys
    50                  55                  60

Gly Ala Ala Asn Tyr Thr Asp Trp Glu Lys Ile Pro Ser Met Ser Lys
65                  70                  75                  80

Asn Arg Val Pro Asp Ser Cys Cys Ile Asn Val Thr Val Gly Cys Gly
                85                  90                  95

Ile Asn Phe Asn Glu Lys Ala Ile His Lys Glu Gly Cys Val Glu Lys
            100                 105                 110

Ile Gly Gly Trp Leu Arg Lys Asn Val Leu Val Val Ala Ala Ala Ala
        115                 120                 125

Leu Gly Ile Ala Phe Val Glu Val Leu Gly Ile Val Phe Ala Cys Cys
    130                 135                 140

Leu Val Lys Ser Ile Arg Ser Gly Tyr Glu Val Met
145                 150                 155

<210> SEQ ID NO 36
<211> LENGTH: 511
<212> TYPE: PRT
<213> ORGANISM: Vesicular Stomatitis Virus

<400> SEQUENCE: 36
```

```
Met Lys Cys Leu Leu Tyr Leu Ala Phe Leu Phe Ile Gly Val Asn Cys
1               5                   10                  15

Lys Phe Thr Ile Val Phe Pro His Asn Gln Lys Gly Asn Trp Lys Asn
                20                  25                  30

Val Pro Ser Asn Tyr His Tyr Cys Pro Ser Ser Ser Asp Leu Asn Trp
            35                  40                  45

His Asn Asp Leu Val Gly Thr Ala Leu Gln Val Lys Met Pro Lys Ser
50                      55                  60

His Lys Ala Ile Gln Ala Asp Gly Trp Met Cys His Ala Ser Lys Trp
65                  70                  75                  80

Val Thr Thr Cys Asp Phe Arg Trp Tyr Gly Pro Lys Tyr Ile Thr His
                85                  90                  95

Ser Ile Arg Ser Phe Thr Pro Ser Val Glu Gln Cys Lys Glu Ser Ile
            100                 105                 110

Glu Gln Thr Lys Gln Gly Thr Trp Leu Asn Pro Gly Phe Pro Pro Gln
        115                 120                 125

Ser Cys Gly Tyr Ala Thr Val Thr Asp Ala Glu Ala Ile Val Gln
        130                 135                 140

Val Thr Pro His His Val Leu Val Asp Glu Tyr Thr Gly Glu Trp Val
145                 150                 155                 160

Asp Ser Gln Phe Ile Asn Gly Lys Cys Ser Asn Asp Ile Cys Pro Thr
                165                 170                 175

Val His Asn Ser Thr Thr Trp His Ser Asp Tyr Lys Val Lys Gly Leu
            180                 185                 190

Cys Asp Ser Asn Leu Ile Ser Met Asp Ile Thr Phe Phe Ser Glu Asp
        195                 200                 205

Gly Glu Leu Ser Ser Leu Gly Lys Lys Gly Thr Gly Phe Arg Ser Asn
210                 215                 220

Tyr Phe Ala Tyr Glu Thr Gly Asp Lys Ala Cys Lys Met Gln Tyr Cys
225                 230                 235                 240

Lys His Trp Gly Val Arg Leu Pro Ser Gly Val Trp Phe Glu Met Ala
                245                 250                 255

Asn Lys Asp Leu Phe Ala Ala Ala Arg Phe Pro Glu Cys Pro Glu Gly
            260                 265                 270

Ser Ser Ile Ser Ala Pro Ser Gln Thr Ser Val Asp Val Ser Leu Ile
        275                 280                 285

Gln Asp Val Glu Arg Ile Leu Asp Tyr Ser Leu Cys Gln Glu Thr Trp
        290                 295                 300

Ser Lys Ile Arg Ala Gly Leu Pro Ile Ser Pro Val Asp Leu Ser Tyr
305                 310                 315                 320

Leu Ala Pro Lys Asn Pro Gly Thr Gly Pro Val Phe Thr Ile Ile Asn
                325                 330                 335

Gly Thr Leu Lys Tyr Phe Glu Thr Arg Tyr Ile Arg Val Asp Ile Ala
            340                 345                 350

Ala Pro Ile Leu Ser Arg Met Val Gly Met Ile Ser Gly Thr Thr Lys
        355                 360                 365

Glu Arg Val Leu Trp Asp Asp Trp Ala Pro Tyr Glu Asp Val Glu Ile
370                 375                 380

Gly Pro Asn Gly Val Leu Arg Thr Ser Ser Gly Tyr Lys Phe Pro Leu
385                 390                 395                 400

Tyr Met Ile Gly His Gly Met Leu Asp Ser Asp Leu His Leu Ser Ser
                405                 410                 415
```

```
Lys Ala Gln Val Phe Glu His Pro His Ile Gln Asp Ala Ala Ser Gln
            420                 425                 430

Leu Pro Asp Gly Glu Thr Leu Phe Phe Gly Asp Thr Gly Leu Ser Lys
        435                 440                 445

Asn Pro Ile Glu Phe Val Glu Gly Trp Phe Ser Ser Trp Lys Ser Ser
    450                 455                 460

Ile Ala Ser Phe Phe Phe Thr Ile Gly Leu Ile Ile Gly Leu Phe Leu
465                 470                 475                 480

Val Leu Arg Val Gly Ile Tyr Leu Cys Ile Lys Leu Lys His Thr Lys
            485                 490                 495

Lys Arg Gln Ile Tyr Thr Asp Ile Glu Met Asn Arg Leu Gly Lys
            500                 505                 510

<210> SEQ ID NO 37
<211> LENGTH: 3
<212> TYPE: PRT
<213> ORGANISM: Artificial
<220> FEATURE:
<223> OTHER INFORMATION: Consensus amino acid sequence of sequon for
      N-linked glycosylation

<400> SEQUENCE: 37

Asn Ser Thr
1

<210> SEQ ID NO 38
<211> LENGTH: 5
<212> TYPE: PRT
<213> ORGANISM: Artificial
<220> FEATURE:
<223> OTHER INFORMATION: Consensus sequence for sequon for N-linked
      glycosylation

<400> SEQUENCE: 38

Gly Asn Ser Thr Met
1               5
```

TARGETED EXTRACELLULAR VESICLES COMPRISING MEMBRANE PROTEINS WITH ENGINEERED GLYCOSYLATION SITES

CROSS-REFERENCE TO RELATED APPLICATIONS

The present application is a Continuation of U.S. application Ser. No. 15/278,568, filed Sep. 28, 2016, which claims the benefit of priority to U.S. Provisional Patent Application No. 62/233,625, filed on Sep. 28, 2015, the content of which is incorporated herein by reference in its entirety.

The instant application contains a Sequence Listing which has been submitted in ASCII format via EFS-WEB and is hereby incorporated by reference in its entirety. Said ASCII copy, created on Apr. 17, 2020, is named sequenct.txt and is 42,536 bytes.

STATEMENT REGARDING FEDERALLY SPONSORED RESEARCH OR DEVELOPMENT

This invention was made with government support under grant number P50 CA090386 awarded by the National Institutes of Health. The government has certain rights in the invention.

BACKGROUND

The field of the invention relates to the use of lipid particles for delivering agents to target cells. In particular, the field of the invention relates to secreted extracellular vesicles (EVs) that contain a targeting membrane protein having an engineered glycosylation site. The secreted extracellular vesicles may be utilized to deliver an agent to a target cell, such as a therapeutic agent.

Secreted extracellular vesicles, such as exosomes, are nanometer-scale lipid vesicles that are produced by many cell types and transfer proteins, nucleic acids, and other molecules between cells in the human body, as well as those of other animals. Targeted exosomes have a wide variety of potential therapeutic uses and have already been shown to be effective for delivery of RNA to neural cells and tumor cells in mice. Here, we describe a method for displaying peptide-based targeting ligands on the exterior of exosomes such that ligands are not degraded by endosomal proteases during exosome biogenesis. This method is novel in that it is the first to acknowledge and address the widespread problem of cleavage of targeting ligands from the luminal terminus extra of integral exosome membrane proteins during exosome biogenesis. Therefore this technology is the first robust method for display of targeting ligands on the exterior of exosomes via the expression of engineered proteins that localize to exosomes. This targeting system can be used for engineering exosomes as targeted gene therapy or drug delivery vehicles in vivo, which could be applied to a wide variety of cell types and diseases.

SUMMARY

Disclosed are extracellular vesicles comprising an engineered targeting protein that targets the extracellular vesicles to a target cell. The targeting protein is a fusion protein that includes as domains: a ligand, an engineered glycosylation site, and an exosome-targeting domain. Exemplary extracellular vesicles may include but are not limited to exosomes.

The ligand of the fusion protein is expressed on the surface of the extracellular vesicles and targets the extracellular vesicles to target cells. The engineered glycosylation site enables the fusion protein to be glycosylated in the cell. Preferably, when the engineered glycosylation site is glycosylated, the fusion protein and/or the component domains of the fusion protein are protected from cleavage from the fusion protein and/or degradation in lysosomes. For example, when the engineered glycosylation site is glycosylated, preferably the ligand is protected from being cleaved from the fusion protein. The exosome-targeting domain targets the fusion protein to intracellular vesicles such as lysosomes, where the fusion protein may be incorporated into the membranes of lysosomes and secreted as extracellular vesicles such as exosomes.

The extracellular vesicles further may comprise an agent, such as a therapeutic agent, and the extracellular vesicles may be utilized to deliver the comprised agent to a target cell. Agents comprised by the extracellular vesicles may include but are not limited to biological molecules, such as cargo RNAs, and other small molecular therapeutic molecules. For example, the fusion protein further may comprise an RNA-domain domain that binds to one or more RNA-motifs present on a cargo RNA such that the fusion protein functions as a packaging protein in order to package the cargo RNA into the extracellular vesicle, prior to the extracellular vesicles being secreted from a cell. In some embodiments, the packaging protein may be referred to as extracellular vesicle-loading protein or "EV-loading protein."

BRIEF DESCRIPTION OF THE FIGURES

FIG. 3. Schematic representation of one embodiment of fusion proteins as contemplated herein. (Top) LAMP2b fusion proteins for expressing a protein of interest on the exosome surface; (Bottom) LAMP2b fusion proteins for expressing a protein of interest on the exosome lumen.

DETAILED DESCRIPTION

Figure 1:
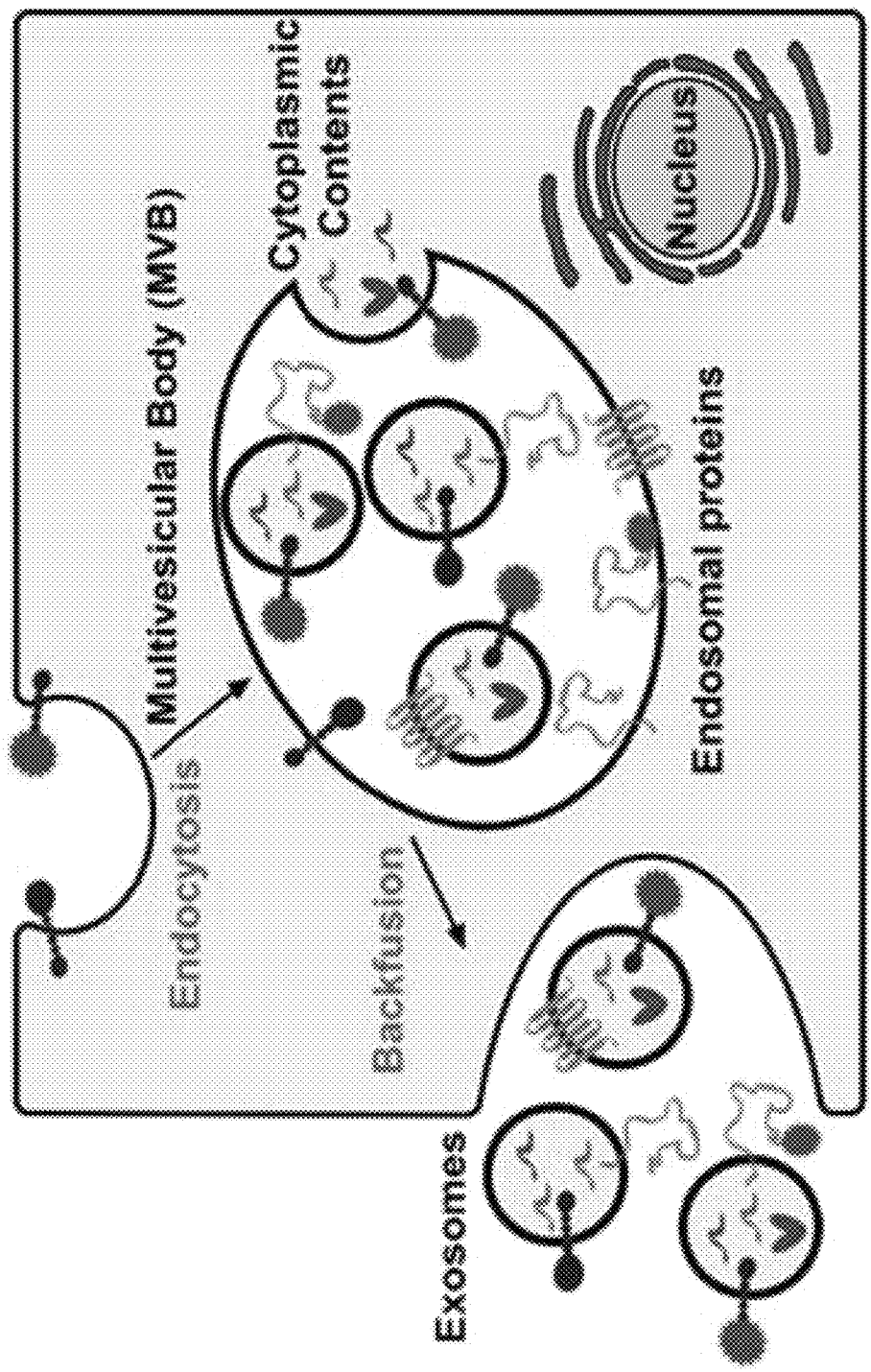
FIG. 1. Exosome Production: Exosomes are formed when the intraluminal vesicles of a multivesicular body (MVB) are released during MVB backfusion with the cell's outer membrane. Exosomes encapsulate endosomal membrane proteins, plasma membrane proteins, and cytoplasmic proteins and RNA.

The present invention is described herein using several definitions, as set forth below and throughout the application.

Unless otherwise specified or indicated by context, the terms "a", "an", and "the" mean "one or more." For example, "a fusion protein," "an RNA," and "a loop" should be interpreted to mean "one or more fusion proteins," "one or more RNAs," and "one or more loops," respectively. An "engineered glycosylation site" should be interpreted to mean "one or more engineered glycosylation sites."

As used herein, "about," "approximately," "substantially," and "significantly" will be understood by persons of ordinary skill in the art and will vary to some extent on the context in which they are used. If there are uses of these terms which are not clear to persons of ordinary skill in the art given the context in which they are used, "about" and "approximately" will mean plus or minus ≤10% of the particular term and "substantially" and "significantly" will mean plus or minus >10% of the particular term.

As used herein, the terms "include" and "including" have the same meaning as the terms "comprise" and "comprising" in that these latter terms are "open" transitional terms that do not limit claims only to the recited elements succeeding these transitional terms. The term "consisting of," while encompassed by the term "comprising," should be interpreted as a "closed" transitional term that limits claims only to the recited elements succeeding this transitional term. The term "consisting essentially of," while encompassed by the term "comprising," should be interpreted as a "partially closed" transitional term which permits additional elements succeeding this transitional term, but only if those additional elements do not materially affect the basic and novel characteristics of the claim.

Disclosed are extracellular vesicles comprising a targeting protein that targets the extracellular vesicles to a target cell. Exemplary extracellular vesicles may include but are not limited to exosomes. However, the term "extracellular vesicles" should be interpreted to include all nanometer-scale lipid vesicles that are secreted by cells such as secreted vesicles formed from lysosomes.

The disclosed extracellular vesicles comprise a "targeting protein." The target protein may be described as a "fusion protein," and the term "targeting protein" and "fusion protein" may be used interchangeably herein depending on context. The fusion protein typically includes: (i) a ligand (e.g., a heterologous ligand) that is expressed on the surface of the extracellular vesicles and targets the extracellular vesicles to target cells, (ii) an engineered glycosylation site (e.g., a heterologous glycosylation site), and (iii) an exosome-targeting domain. In some embodiments, the fusion protein has a luminal N-terminus and a cytosolic C-terminus and the fusion protein comprises from N-terminus to C-terminus: the ligand, the glycosylation site, and the exosome-targeting domain.

The ligand of the fusion protein typically is a heterologous amino acid sequence (i.e., relative to the engineered glycosylation site and/or relative to the exosome-targeting domain) that binds to a receptor present on the surface of a target cell (e.g., a protein receptor, a carbohydrate receptor, or a lipid receptor present on the surface of a cell). For example, suitable ligands may include a ligand for a cell receptor present on a target cell, or an antibody or binding fragment thereof that binds to a cell receptor or other membrane protein present on a target cell. The ligand of the fusion protein typically is present at the luminal end of the fusion protein, which optionally may be the N-terminus of the fusion protein. For example, the fusion protein may comprise a structure as follows: $N_{ter}$-signal peptide-ligand for target cell—engineered glycosylation site—exosome targeting domain—$C_{ter}$.

The engineered glycosylation site of the fusion protein may be defined as a sequence of amino acids that is a target for enzymatic, N-linked glycosylation when the fusion protein is expressed in a cell. The engineered glycosylation site may be present adjacent to the ligand of the fusion protein (e.g., $N_{ter}$-signal peptide-ligand for target cell-engineered glycosylation site-exosome targeting domain-$C_{ter}$). Preferably, when the engineered glycosylation site is glycosylated, the fusion protein or the component domains of the fusion protein are protected from cleavage from the fusion protein and/or degradation in lysosomes. (See Hung et al.; and Schulz). For example, the fusion protein may include a glycosylation motif and/or may be engineered to include a glycosylation motif in order to protect or inhibit the fusion protein and/or component domains of the fusion protein from proteolytic cleavage from the fusion protein or degradation, such as intracellular proteolysis. (See Kundra et al.). Suitable glycosylation motifs may include the NX(S/T) consensus sequon and in particular the NST sequon (SEQ ID NO:37). In some embodiments, the fusion protein may include a GNSTM sequon (SEQ ID NO:38). The NST sequence is a known N-linked glycosylation sequon, and the amino acids G and M flanking the sequon may increase glycosylation frequency in mammals. (See Ballo-Polo et al.). The glycosylation site typically is "engineered," meaning that the glycosylation site typically is not naturally present in the fusion protein or any of the component proteins of the fusion protein, and rather, is introduced into the fusion protein, for example, by recombinant engineering.

The exosome targeting domain of the fusion protein may include but is not limited to a domain of an exosomal-associated protein and/or a lysosome-associated protein. A database of exosomal proteins, RNA, and lipids is provided by ExoCarta at its website. (See also, Mathivanan et al., Nucl. Acids Res. 2012, Vol. 40, Database issue D1241-1244, published online 11 Oct. 2011, the content of which is incorporated herein by reference in its entirety.) Suitable exosomal-associated proteins, which also may be described as exosomal vesicle-enriched proteins or (EEPs) have been described. (See Hung and Leonard, "A platform for actively loading cargo RNA to elucidate limiting steps in EV-mediated delivery," *J. Extracellular Vesicles*, 2016, 5: 31027, published 13 May 2016, the content of which is incorporated herein by reference in its entirety). In some embodiments, suitable domains of lysosome-associated proteins may include domains from lysosome membrane proteins having a luminal N-terminus and a cytoplasmic C-terminus, although membrane proteins having different orientations also may be suitable (e.g. membrane proteins having a luminal C-terminus and a cytoplasmic N-terminus).

In some embodiments, the exosome-targeting domain is a domain of a lysosome-associated protein. Suitable lysosome-associated protein may include, but are not limited to, lysosome membrane proteins. (See Saftig, Lysosomes, Chapter 6, "Lysosome Membrane Proteins" 2004). Lysosome-associated membrane proteins (LAMPs) and lysosome integral membrane proteins (LIMPs) are the most abundant proteins of the lysosome membrane. (See id.).

In some embodiments of the fusion proteins disclosed herein, the exosome-targeting domain is an exosome-targeting domain of a LAMP. Suitable LAMPs may include, but are not limited to, LAMP-1 and LAMP-2, and isoforms thereof. (See Fukuda et al., "Cloning of cDNAs Encoding Human Lysosomal Membrane Glycoproteins, h-lamp-1 and h-lamp-2," J. Biol. Chem., Vol. 263, No. 35 December 1988, pp. 18920-18928; and Fukuda, "Lysosomal Membrane Glycoproteins," J. Biol. Chem., Vol. 266, No. 32, November 1991, pp. 21327, 21330.) LAMPs are lysosome-membrane proteins having a luminal (i.e., extracytoplasmic) N-terminus and a cytoplasmic C-terminus. (See id.). The mRNAs for expressing LAMPs may be processed differently to give isoforms. For example, there are three isoforms for LAMP-2 designated as LAMP-2a, LAMP-2b, and LAMP-2c. (See UniProt Database, entry number P13473-LAMP2_HUMAN, the contents of which is incorporated herein by reference in its entirety). LAMP-1 has a single isoform. (See UniProt Database, entry number P11279-LAMP1_HUMAN, the content of which is incorporated herein by reference in its entirety). The full-length amino acid sequence of LAMP-2a, LAMP-2b, and LAMP-2c are provided herein as SEQ ID NOs:20, 21, and 22, respectively. The full-length amino acid sequence of LAMP-1 is provided herein as SEQ ID NO:26. The fusion proteins disclosed herein may include the full-length amino acid sequence of a LAMP or a variant thereof as contemplated herein having a percentage of sequence identity in comparison to the amino acid sequence of the wild-type LAMP, or a fragment thereof comprising a portion of the wild-type LAMP (e.g., SEQ ID NOs:23, 24, 25, and 27 comprising a portion of the C-termini of LAMP-2a, LAMP-2b, LAMP-2c, and LAMP-1, respectively).

For LAMPs, the C-terminus (e.g., comprising the 10-11 C-terminal amino acids) has been shown to be important for targeting LAMPs to lysosomes. (See id.; and Fukuda 1991). In some embodiments of the disclosed extracellular vesicles, the fusion protein comprises the RNA-binding domain fused to the C-terminus of one of SEQ ID NOs:23, 24, 25, and 27, which comprise a portion of the C-termini of LAMP-2a, LAMP-2b, LAMP-2c, and LAMP-1, respectively). The fusion protein may include the cytoplasmic domain of a LAMP and optionally may include additional amino acid sequences (e.g., at least a portion of the transmembrane domain and/or at least a portion of the luminal domain).

In some embodiments, the exosome-targeting domain is an exosome-targeting domain of a LIMP. Suitable LIMPs may include, but are not limited to, LIMP-1 (CD63) and LAMP-2, and isoforms thereof. LIMPs are lysosome-membrane proteins having one or more luminal domains, multiple transmembrane domains, and a cytoplasmic C-terminus. (See Ogata et al., "Lysosomal Targeting of Limp II Membrane Glycoprotein Requires a Novel Leu-Ile Motif at a Particular Position in Its Cytoplasmic Tail," J. Biol. Chem., Vol. 269, No. 7, February 1994, pp. 5210-5217). The mRNAs for expressing LIMPs may be processed differently to give isoforms. For example, there are three isoforms for LIMP-1 designated as LIMP-1a, LIMP-1b, and LIMP-1c and two isoforms for LIMP-2 designated as LIMP-2a and LIMP-2b. (See UniProt Database, entry number Q10148-SCRB2_HUMAN, and UniProt Database, entry number P08962-CD63_HUMAN, the content of which is incorporated herein by reference in its entirety). The full-length amino acid sequence of LIMP-1a, LIMP-1b, and LIMP-1c are provided herein as SEQ ID NOs:28, 29, and 30, respectively. The full-length amino acid sequence of LIMP-2A and LIMP-2b are provided herein as SEQ ID NOs:32 and 33, respectively. The fusion proteins disclosed herein may include the full-length amino acid sequence of a LIMP or a variant thereof as contemplated herein having a percentage of sequence identity in comparison to the amino acid sequence of the wild-type LIMP, or a fragment thereof comprising a portion of the wild-type LIMP (e.g., SEQ ID NO:31 comprising a portion of the C-termini of LIMP-1a, LIMP-1b, LIMP-1C and SEQ ID NO:34 comprising a portion of the C-termini of LIMP-2a and LIMP-2b).

For LIMPs, the C-terminus (e.g., comprising the 14-19 C-terminal amino acids) has been shown to be important for targeting LAMPs to lysosomes. (See Ogata et al.). In some embodiments of the disclosed extracellular vesicles, the fusion protein comprises the RNA-binding domain fused to the C-terminus of one of SEQ ID NOs:31 and 34, which comprise a portion of the C-termini of LIMP-1a, LIMP-1b, LIMP-1c, and LIMP-2a and LIMP-2b). The fusion protein may include the cytoplasmic domain of a LIMP and optionally may include additional amino acid sequences (e.g., at least a portion of the transmembrane domain and/or at least a portion of the luminal domain).

In some embodiments of the fusion proteins disclosed herein the exosome-targeting domain is an exosome-targeting domain of CD63 or isoforms thereof. The CD63 protein alternately may be referred to by aliases including Lysosome-Integrated Membrane Protein 1 (LIMP-1), MLA1, Lysosomal-Associated Membrane Protein 3, Ocular Melanoma-Associated Antigen, Melanoma 1 Antigen, Melanoma-Associated Antigen ME491, Tetraspanin-30, Granulophysin, and Tspan-30. Isoforms of CD63 may include CD63 Isoform A (i.e., LIMP-1a (SEQ ID NO:28)), CD63 Isoform C (i.e., LIMP-1b (SEQ ID NO:29)) and CD63 Isoform D Precursor (provided herein as SEQ ID NO:35).

In some embodiments of the fusion proteins disclosed herein the exosome-targeting domain is an exosome-targeting domain of a viral transmembrane protein. Viral transmembrane proteins are known in the art. (See e.g., Fields Virology, Sixth Edition, 2013. See also White et al., Crit. Rev. Biochem. Mol. Biol. 2008; 43(3): 189-219). Specifically, the exosome-targeting domain may be an exosome-targeting domain of the G glycoprotein of Vesicular Stomatitis Virus (VSV G-protein). The amino acid sequence of VSV G-protein is provided herein as SEQ ID NO:36.

The disclosed extracellular vesicles further may comprise an agent, such as a therapeutic agent, where the extracellular vesicles deliver the agent to a target cell. Agents comprised by the extracellular vesicles may include but are not limited to therapeutic drugs (e.g., small molecule drugs), therapeutic proteins, and therapeutic nucleic acids (e.g., therapeutic RNA). In some embodiments, the disclosed extracellular vesicles comprise a therapeutic RNA as a so-called "cargo RNA." For example, in some embodiments the fusion protein further may comprise an RNA-domain (e.g., at a cytosolic C-terminus of the fusion protein) that binds to one or more RNA-motifs present in the cargo RNA in order to package the cargo RNA into the extracellular vesicle, prior to the extracellular vesicles being secreted from a cell. As such, the fusion protein may function as both of a "targeting protein" and a "packaging protein." In some embodiments, the packaging protein may be referred to as extracellular vesicle-loading protein or "EV-loading protein." (See Hung and Leonard, "A platform for actively loading cargo RNA to elucidate limiting steps in EV-mediated delivery," *J. Extracellular Vesicles,* 2016, 5: 31027, published 13 May 2016, the content of which is incorporated herein by reference in its entirety.)

In embodiments in which the extracellular vesicles comprise a cargo RNA, the cargo RNA which may be described as a fusion RNA comprising: (1) a RNA-motif that binds the RNA-binding domain of the fusion protein and further, (2) additional functional RNA sequences that be utilized for therapeutic purposes (e.g., miRNA, shRNA, mRNA, ncRNA, sgRNA or a combination of any of these RNAs).

The cargo RNA of the disclosed extracellular vesicles may be of any suitable length. For example, in some embodiments the cargo RNA may have a nucleotide length of at least about 10 nt, 20 nt, 30 nt, 40 nt, 50 nt, 100 nt, 200 nt, 500 nt, 1000 nt, 2000 nt, 5000 nt, or longer. In other embodiments, the cargo RNA may have a nucleotide length of no more than about 5000 nt, 2000 nt, 1000 nt, 500 nt, 200 nt, 100 nt, 50 nt, 40 nt, 30 nt, 20 nt, or 10 nt. In even further embodiments, the cargo RNA may have a nucleotide length within a range of these contemplated nucleotide lengths, for example, a nucleotide length between a range of about 10 nt-5000 nt, or other ranges. The cargo RNA of the disclosed extracellular vesicles may be relatively long, for example, where the cargo RNA comprises an mRNA or another relatively long RNA.

Suitable RNA-binding domains and RNA-motifs for the components of the presently disclosed extracellular vesicles may include, but are not limited to, RNA-binding domains and RNA-motifs of bacteriophage. (See, e.g., Keryer-Bibens et al., "Tethering of proteins to RNAs by bacteriophage proteins," Biol. Cell (2008) 100, 125-138, the content of which is incorporated herein by reference in its entirety).

In some embodiments of the disclosed extracellular vesicles, the RNA-binding domain of the fusion protein is an RNA-binding domain of coat protein of MS2 bacteriophage or R17 bacteriophage, which may be considered to be interchangeable. (See, e.g., Keryer-Bibens et al.; and Stockley et al., "Probing sequence-specific RNA recognition by the bacteriophage MS2 coat protein," Nucl. Acids. Res., 1995, Vol. 23, No. 13, pages 2512-2518, the content of which is incorporated herein by reference in its entirety). The full-length amino acid sequence of the coat protein of MS2 bacteriophage is provided herein as SEQ ID NO:1. The fusion proteins disclosed herein may include the full-length amino acid sequence of the coat protein of MS2 bacteriophage or a variant thereof as contemplated herein having a percentage of sequence identity in comparison to the amino acid sequence of the coat protein of MS2 bacteriophage, or a fragment thereof comprising a portion of the coat protein of MS2 bacteriophage (e.g., the RNA-binding domain of MS2 or SEQ ID NO:2, comprising the amino acid sequence (2-22) of the coat protein of MS2 bacteriophage).

In embodiments where the fusion protein comprises an RNA-binding domain of coat protein of MS2 bacteriophage, the cargo RNA typically comprises an RNA-motif of MS2 bacteriophage RNA which may form a high affinity binding loop that binds to the RNA-binding domain of the fusion protein. (See Peabody et al., "The RNA binding site of bacteriophage MS2 coat protein," The EMBO J., vol. 12, no. 2, pp. 595-600, 1993; Keryer-Bibens et al.; and Stockley et al., the contents of which are incorporated herein by reference in their entireties). The RNA-motif of MS2 bacteriophage and R17 bacteriophage has been characterized. (See id.). The RNA-motif has been determined to comprise minimally a 21-nt stem-loop structure where the identity of the nucleotides forming the stem do not appear to influence the affinity of the coat protein for the RNA-motif, but where the sequence of the loop contains a 4-nt sequence (AUUA (SEQ ID NO:3)), which does influence the affinity of the coat protein for the RNA-motif. Also important, is an unpaired adenosine two nucleotides upstream of the loop. In some embodiments of the disclosed extracellular vesicles, the RNA-motif comprises one or more high affinity binding loops comprising a sequence and structure selected from the group consisting of:

```
                                    SEQ ID NO: 4
         U U
        A   A
         N-N
         N-N
        A
         N-N
         N-N
         N-N
         N-N
```

-continued

```
              SEQ ID NO: 5
      C U
    A   A,
    N-N
    N-N
   A
    N-N
    N-N
    N-N
    N-N
              SEQ ID NO: 6
      U C
    A   A,
    N-N
    N-N
   A
    N-N
    N-N
    N-N
    N-N
``` where N—N is any two base-paired RNA nucleotides (e.g., where each occurrence of N—N is independently selected from any of A-U, C-G, G-C, G-U, U-A, or U-G, and each occurrence of N—N may be the same or different). Specifically, the high affinity binding loop may comprise a sequence selected from the group consisting of SEQ ID NO:7 (5'-ACAUGAGGAUUACCCAUGU-3'), SEQ ID NO:8 (5'-ACAUGAGGACUACCCAUGU-3'), and SEQ ID NO:9 (5'-ACAUGAGGAUCACCCAUGU-3'), or a variant thereof having a percentage sequence identity.

Preferably, the RNA-binding domain of the fusion protein binds to the RNA-motif with an affinity of at least about $1\times10^{-8}$ M. More preferably, the RNA-binding domain of the fusion protein binds to the RNA-motif with an affinity of at least about $1\times10^{-9}$ M, even more preferably with an affinity of at least about $1\times10^{-10}$ M.

In addition to the RNA-motif for binding to the RNA-binding domain of the fusion protein, the cargo RNA may include additional functional RNA sequences that be utilized for therapeutic purposes (e.g., miRNA, shRNA, mRNA, ncRNA, sgRNA, or a combination of any of these RNAs). (See Marcus et al., "FedExosomes: Engineering Therapeutic Biological Nanoparticles that Truly Deliver," Pharmaceuticals 2013, 6, 659-680; György et al., Therapeutic application of extracellular vesicles: clinical promise and open questions," Annu. Rev. Pharmacol. Toxicol. 2015; 55:439-64, Epub 2014 Oct. 3, the contents of which are incorporated herein by reference in their entireties). As such, the cargo RNA may be characterized as a hybrid RNA including the RNA-motif for binding to the RNA-binding domain of the fusion protein and including an additional RNA (e.g., miRNA, shRNA, mRNA, ncRNA, sgRNA, or a combination of any of these RNAs fused at the 5'-terminus or 3'-terminus or at an internal portion within the RNA), which may be a therapeutic RNA.

In other embodiments of the disclosed extracellular vesicles, the RNA-binding domain of the fusion protein is an RNA-binding domain of the N-protein of a lambdoid bacteriophage, which may include but is not limited to lambda bacteriophage, P22 bacteriophage, and phi21 bacteriophage. (See, e.g., Keryer-Bibens et al.; Bahadur et al., "Binding of the Bacteriophage P22 N-peptide to the boxB RNA-motif Studied by Molecule Dynamics Simulations," Biophysical J., Vol., 97, December 2009, 3139-3149; Cilley et al., "Structural mimicry in the phage phi21 N peptide-boxB RNA complex," RNA (2003), 9:663-376; the contents of which are incorporated herein by reference in their entireties). The full-length amino acid sequence of the N-protein of lambda bacteriophage, P22 bacteriophage, and phi21 bacteriophage are provided herein as SEQ ID NOs:10, 11, and 12, respectively. The fusion proteins disclosed herein may include the full-length amino acid sequence of the N-protein of the lambdoid bacteriophage or a variant thereof as contemplated herein having a percentage of sequence identity in comparison to the amino acid sequence of the N-protein of the lambdoid bacteriophage, or a fragment thereof comprising a portion of the N-protein of the lambdoid bacteriophage (e.g., the RNA-binding domain of the N-protein of any of lambda bacteriophage, P22 bacteriophage, and phi21 bacteriophage, or SEQ ID NOs:13, 14, and 15, comprising portions of the N-proteins of lambda bacteriophage, P22 bacteriophage, and phi21 bacteriophage, respectively).

In embodiments where the fusion protein comprises an RNA-binding domain of coat protein of a lambdoid bacteriophage, the cargo RNA typically comprises an RNA-motif of lambda bacteriophage RNA which may form a high affinity binding loop called "boxB" that binds to the RNA-binding domain of the fusion protein. (See Keryer-Bibens et al.). BoxB of lambdoid bacteriophage has been characterized. (See id.; Bahadur, et al.; and Cilley et al.). For lambda bacteriophage, boxB has been determined to comprise minimally a 15-nt stem-loop structure where the identity of the nucleotides forming the stem and loop influence the affinity of the coat protein for the RNA-motif. (See Keryer-Bibens et al.). In some embodiments of the disclosed extracellular vesicles, the RNA-motif comprises one or more high affinity binding loops comprising a sequence and structure selected from the group consisting of:

```
              SEQ ID NO: 16
       A
      A G
     G   A
     U-A
     C-G
     C-G
     C-G
     G-C
              SEQ ID NO: 17
       A
      A A
     G   A,
     U-A
     C-G
     C-G
     C-G
     G-C
``` or a variant thereof having a percentage sequence identity, where the variant binds to the RNA-binding domain of the fusion protein. Preferably, the RNA-motif binds to the RNA-binding domain of the fusion protein with an affinity of at least about $1\times10^{-8}$ M, more preferably with an affinity of at least about $1\times10^{-9}$ M, even more preferably with an affinity of at least about $1\times10^{-19}$ M.

For P22 bacteriophage, boxB has been determined to comprise minimally a 15-nt stem-loop structure where the identity of the nucleotides forming the stem and loop influence the affinity of the coat protein for the RNA-motif. (See Bahadur et al.). In some embodiments of the disclosed extracellular vesicles, the RNA-motif comprises one or more high affinity binding loops comprising a sequence and structure of:

```
                              SEQ ID NO: 18
          C
        A   A
       G    A
        U-A
        C-G
        G-C
        C-G
        G-C
```

For phi21 bacteriophage, boxB has been determined to comprise minimally a 20-nt stem-loop structure where the identity of the nucleotides forming the stem and loop influence the affinity of the coat protein for the RNA-motif. (See Cilley et al.). In some embodiments of the disclosed extracellular vesicles, the RNA-motif comprises one or more high affinity binding loops comprising a sequence and structure of:

```
                              SEQ ID NO: 19
         A A
        U   C
       C     C.
        U-G
        C-G
        C-G
        A-U
        C-G
        U-A
        U-G
```

The disclosed extracellular vesicles may be prepared by methods known in the art. For example, the disclosed extracellular vesicles may be prepared by expressing in a eukaryotic cell (a) an mRNA that encodes the packaging/fusion protein and (b) expressing in the eukaryotic cell the cargo RNA (or transducing the eukaryotic cell with the cargo RNA that has been prepared in silico). The mRNA for the packaging/fusion protein and the cargo RNA may be expressed from vectors that are transfected into suitable production cells for producing the disclosed extracellular vesicles. The mRNA for the packaging/fusion protein and the cargo RNA may be expressed from the same vector (e.g., where the vector expresses the mRNA for the packaging/fusion protein and the cargo RNA from separate promoters), or the mRNA for the packaging/fusion protein and the cargo RNA may be expressed from separate vectors. The vector or vectors for expressing the mRNA for the packaging/fusion protein and the cargo RNA may be packaged in a kit designed for preparing the disclosed extracellular vesicles.

Also contemplated herein are methods for using the disclosed extracellular vesicles. For example, the disclosed extracellular vesicles may be used for delivering a therapeutic agent such as cargo RNA to a target cell, where the methods include contacting the target cell with the disclosed extracellular vesicles. The disclosed extracellular vesicles may be formulated as part of a pharmaceutical composition for treating a disease or disorder and the pharmaceutical composition may be administered to a patient in need thereof to delivery the cargo RNA to target cells in order to treat the disease or disorder.

The disclosed extracellular vesicles may comprise novel proteins, polypeptides, or peptides. As used herein, the terms "protein" or "polypeptide" or "peptide" may be used interchangeable to refer to a polymer of amino acids. Typically, a "polypeptide" or "protein" is defined as a longer polymer of amino acids, of a length typically of greater than 50, 60, 70, 80, 90, or 100 amino acids. A "peptide" is defined as a short polymer of amino acids, of a length typically of 50, 40, 30, 20 or less amino acids.

A "protein" as contemplated herein typically comprises a polymer of naturally or non-naturally occurring amino acids (e.g., alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine). The proteins contemplated herein may be further modified in vitro or in vivo to include non-amino acid moieties. These modifications may include but are not limited to acylation (e.g., O-acylation (esters), N-acylation (amides), S-acylation (thioesters)), acetylation (e.g., the addition of an acetyl group, either at the N-terminus of the protein or at lysine residues), formylation lipoylation (e.g., attachment of a lipoate, a C8 functional group), myristoylation (e.g., attachment of myristate, a C14 saturated acid), palmitoylation (e.g., attachment of palmitate, a C16 saturated acid), alkylation (e.g., the addition of an alkyl group, such as an methyl at a lysine or arginine residue), isoprenylation or prenylation (e.g., the addition of an isoprenoid group such as farnesol or geranylgeraniol), amidation at C-terminus, glycosylation (e.g., the addition of a glycosyl group to either asparagine, hydroxylysine, serine, or threonine, resulting in a glycoprotein). Distinct from glycation, which is regarded as a non-enzymatic attachment of sugars, polysialylation (e.g., the addition of polysialic acid), glypiation (e.g., glycosylphosphatidylinositol (GPI) anchor formation, hydroxylation, iodination (e.g., of thyroid hormones), and phosphorylation (e.g., the addition of a phosphate group, usually to serine, tyrosine, threonine or histidine).

The term "amino acid residue" also may include amino acid residues contained in the group consisting of homocysteine, 2-Aminoadipic acid, N-Ethylasparagine, 3-Aminoadipic acid, Hydroxylysine, β-alanine, β-Amino-propionic acid, allo-Hydroxylysine acid, 2-Aminobutyric acid, 3-Hydroxyproline, 4-Aminobutyric acid, 4-Hydroxyproline, piperidinic acid, 6-Aminocaproic acid, Isodesmosine, 2-Aminoheptanoic acid, allo-Isoleucine, 2-Aminoisobutyric acid, N-Methylglycine, sarcosine, 3-Aminoisobutyric acid, N-Methylisoleucine, 2-Aminopimelic acid, 6-N-Methyllysine, 2,4-Diaminobutyric acid, N-Methylvaline, Desmosine, Norvaline, 2,2'-Diaminopimelic acid, Norleucine, 2,3-Diaminopropionic acid, Ornithine, and N-Ethylglycine.

The proteins disclosed herein may include "wild type" proteins and variants, mutants, and derivatives thereof. As used herein the term "wild type" is a term of the art understood by skilled persons and means the typical form of an organism, strain, gene or characteristic as it occurs in nature as distinguished from mutant or variant forms. As used herein, a "variant, "mutant," or "derivative" refers to a protein molecule having an amino acid sequence that differs from a reference protein or polypeptide molecule. A variant or mutant may have one or more insertions, deletions, or substitutions of an amino acid residue relative to a reference molecule. A variant or mutant may include a fragment of a reference molecule. For example, a mutant or variant molecule may one or more insertions, deletions, or substitution of at least one amino acid residue relative to a reference polypeptide (e.g., any of SEQ ID NOs: 1, 2, 10-15, and 20-36). The sequence of the full-length coat protein of MS2 bacteriophage, the sequence of the full-length N-protein of lambda bacteriophage, the sequence of the full-length N-protein of P22 bacteriophage, the sequence of the full-length N-protein of phi21 bacteriophage, the sequence of the full-length LAMP-2a, the sequence of the full-length LAMP-2b, and the sequence of the full-length LAMP-2c, are presented as SEQ ID NOs:1, 10, 11, 12, 20, 21, and 22, respectively, and may be used as a reference in this regard.

Regarding proteins, a "deletion" refers to a change in the amino acid sequence that results in the absence of one or more amino acid residues. A deletion may remove at least 1, 2, 3, 4, 5, 10, 20, 50, 100, 200, or more amino acids residues. A deletion may include an internal deletion and/or a terminal deletion (e.g., an N-terminal truncation, a C-terminal truncation or both of a reference polypeptide). A "variant," "mutant," or "derivative" of a reference polypeptide sequence may include a deletion relative to the reference polypeptide sequence.

Regarding proteins, "fragment" is a portion of an amino acid sequence which is identical in sequence to but shorter in length than a reference sequence. A fragment may comprise up to the entire length of the reference sequence, minus at least one amino acid residue. For example, a fragment may comprise from 5 to 1000 contiguous amino acid residues of a reference polypeptide, respectively. In some embodiments, a fragment may comprise at least 5, 10, 15, 20, 25, 30, 40, 50, 60, 70, 80, 90, 100, 150, 250, or 500 contiguous amino acid residues of a reference polypeptide. Fragments may be preferentially selected from certain regions of a molecule. The term "at least a fragment" encompasses the full length polypeptide. For example, a fragment of a protein may comprise or consist essentially of a contiguous portion of an amino acid sequence of the full-length proteins of any of SEQ ID NOS: 1, 2, 10-15, and 20-36. A fragment may include an N-terminal truncation, a C-terminal truncation, or both truncations relative to the full-length protein. A "variant," "mutant," or "derivative" of a reference polypeptide sequence may include a fragment of the reference polypeptide sequence.

Regarding proteins, the words "insertion" and "addition" refer to changes in an amino acid sequence resulting in the addition of one or more amino acid residues. An insertion or addition may refer to 1, 2, 3, 4, 5, 10, 20, 30, 40, 50, 60, 70, 80, 90, 100, 150, 200, or more amino acid residues. A "variant," "mutant," or "derivative" of a reference polypeptide sequence may include an insertion or addition relative to the reference polypeptide sequence. A variant of a protein may have N-terminal insertions, C-terminal insertions, internal insertions, or any combination of N-terminal insertions, C-terminal insertions, and internal insertions.

Regarding proteins, the phrases "percent identity" and "% identity," refer to the percentage of residue matches between at least two amino acid sequences aligned using a standardized algorithm. Methods of amino acid sequence alignment are well-known. Some alignment methods take into account conservative amino acid substitutions. Such conservative substitutions, explained in more detail below, generally preserve the charge and hydrophobicity at the site of substitution, thus preserving the structure (and therefore function) of the polypeptide. Percent identity for amino acid sequences may be determined as understood in the art. (See, e.g., U.S. Pat. No. 7,396,664, which is incorporated herein by reference in its entirety). A suite of commonly used and freely available sequence comparison algorithms is provided by the National Center for Biotechnology Information (NCBI) Basic Local Alignment Search Tool (BLAST), which is available from several sources, including the NCBI, Bethesda, Md., at its website. The BLAST software suite includes various sequence analysis programs including "blastp," that is used to align a known amino acid sequence with other amino acids sequences from a variety of databases. As described herein, variants, mutants, or fragments (e.g., a protein variant, mutant, or fragment thereof) may have 99%, 98%, 97%, 96%, 95%, 94%, 93%, 92%, 91%, 90%, 80%, 70%, 60%, 50%, 40%, 30%, or 20% amino acid sequence identity relative to a reference molecule (e.g., relative to any of SEQ ID NOs: 1, 2, 10-15, and 20-36).

Regarding proteins, percent identity may be measured over the length of an entire defined polypeptide sequence, for example, as defined by a particular SEQ ID number, or may be measured over a shorter length, for example, over the length of a fragment taken from a larger, defined polypeptide sequence, for instance, a fragment of at least 15, at least 20, at least 30, at least 40, at least 50, at least 70 or at least 150 contiguous residues. Such lengths are exemplary only, and it is understood that any fragment length supported by the sequences shown herein, in the tables, figures or Sequence Listing, may be used to describe a length over which percentage identity may be measured.

Regarding proteins, the amino acid sequences of variants, mutants, or derivatives as contemplated herein may include conservative amino acid substitutions relative to a reference amino acid sequence. For example, a variant, mutant, or derivative protein may include conservative amino acid substitutions relative to a reference molecule. "Conservative amino acid substitutions" are those substitutions that are a substitution of an amino acid for a different amino acid where the substitution is predicted to interfere least with the properties of the reference polypeptide. In other words, conservative amino acid substitutions substantially conserve the structure and the function of the reference polypeptide. The following table provides a list of exemplary conservative amino acid substitutions which are contemplated herein:

| Original Residue | Conservative Substitution |
|---|---|
| Ala | Gly, Ser |
| Arg | His, Lys |
| Asn | Asp, Gln, His |
| Asp | Asn, Glu |
| Cys | Ala, Ser |
| Gln | Asn, Glu, His |
| Glu | Asp, Gln, His |
| Gly | Ala |
| His | Asn, Arg, Gln, Glu |
| Ile | Leu, Val |
| Leu | Ile, Val |
| Lys | Arg, Gln, Glu |
| Met | Leu, Ile |
| Phe | His, Met, Leu, Trp, Tyr |
| Ser | Cys, Thr |
| Thr | Ser, Val |
| Trp | Phe, Tyr |
| Tyr | His, Phe, Trp |
| Val | Ile, Leu, Thr |

Conservative amino acid substitutions generally maintain (a) the structure of the polypeptide backbone in the area of the substitution, for example, as a beta sheet or alpha helical conformation, (b) the charge or hydrophobicity of the molecule at the site of the substitution, and/or (c) the bulk of the side chain.

The disclosed proteins, mutants, variants, or described herein may have one or more functional or biological activities exhibited by a reference polypeptide (e.g., one or more functional or biological activities exhibited by wildtype protein). For example, the disclosed proteins, mutants, variants, or derivatives thereof may have one or more biological activities that include binding to a single-stranded RNA, binding to a double-stranded RNA, binding to a target polynucleotide sequence, and targeting a protein to a vesicle (e.g. a lysosome or exosome).

The disclosed proteins may be substantially isolated or purified. The term "substantially isolated or purified" refers to proteins that are removed from their natural environment, and are at least 60% free, preferably at least 75% free, and more preferably at least 90% free, even more preferably at least 95% free from other components with which they are naturally associated.

Also disclosed herein are polynucleotides, for example polynucleotide sequences that encode proteins (e.g., DNA that encodes a polypeptide having the amino acid sequence of any of SEQ ID NOs: 1, 2, 10-15, and 20-36 or a polypeptide variant having an amino acid sequence with at least about 20%, 30%, 40%, 50%, 60%, 70%, 80%, 90%, 95%, 96%, 97%, 98%, or 99% sequence identity to any of SEQ ID NOs: 1, 2, 10-15, and 20-36; DNA encoding the polynucleotide sequence of any of SEQ ID NOs:3-9 and 16-19 or encoding a polynucleotide variant having a nucleotide sequence with at least about 20%, 30%, 40%, 50%, 60%, 70%, 80%, 90%, 95%, 96%, 97%, 98%, or 99% sequence identity to any of SEQ ID NOs:3-9 and 16-19; RNA comprising the polynucleotide sequence of any of SEQ ID NOs:3-9 and 16-19 or a polynucleotide variant having a nucleotide sequence with at least about 20%, 30%, 40%, 50%, 60%, 70%, 80%, 90%, 95%, 96%, 97%, 98%, or 99% sequence identity to any of SEQ ID NOs:3-9 and 16-19).

The terms "polynucleotide," "polynucleotide sequence," "nucleic acid" and "nucleic acid sequence" refer to a nucleotide, oligonucleotide, polynucleotide (which terms may be used interchangeably), or any fragment thereof. These phrases also refer to DNA or RNA of genomic, natural, or synthetic origin (which may be single-stranded or double-stranded and may represent the sense or the antisense strand).

Regarding polynucleotide sequences, the terms "percent identity" and "% identity" refer to the percentage of residue matches between at least two polynucleotide sequences aligned using a standardized algorithm. Such an algorithm may insert, in a standardized and reproducible way, gaps in the sequences being compared in order to optimize alignment between two sequences, and therefore achieve a more meaningful comparison of the two sequences. Percent identity for a nucleic acid sequence may be determined as understood in the art. (See, e.g., U.S. Pat. No. 7,396,664, which is incorporated herein by reference in its entirety). A suite of commonly used and freely available sequence comparison algorithms is provided by the National Center for Biotechnology Information (NCBI) Basic Local Alignment Search Tool (BLAST), which is available from several sources, including the NCBI, Bethesda, Md., at its website. The BLAST software suite includes various sequence analysis programs including "blastn," that is used to align a known polynucleotide sequence with other polynucleotide sequences from a variety of databases. Also available is a tool called "BLAST 2 Sequences" that is used for direct pairwise comparison of two nucleotide sequences. "BLAST 2 Sequences" can be accessed and used interactively at the NCBI website. The "BLAST 2 Sequences" tool can be used for both blastn and blastp (discussed above).

Regarding polynucleotide sequences, percent identity may be measured over the length of an entire defined polynucleotide sequence, for example, as defined by a particular SEQ ID number, or may be measured over a shorter length, for example, over the length of a fragment taken from a larger, defined sequence, for instance, a fragment of at least 20, at least 30, at least 40, at least 50, at least 70, at least 100, or at least 200 contiguous nucleotides. Such lengths are exemplary only, and it is understood that any fragment length supported by the sequences shown herein, in the tables, figures, or Sequence Listing, may be used to describe a length over which percentage identity may be measured.

Regarding polynucleotide sequences, "variant," "mutant," or "derivative" may be defined as a nucleic acid sequence having at least 50% sequence identity to the particular nucleic acid sequence over a certain length of one of the nucleic acid sequences using blastn with the "BLAST 2 Sequences" tool available at the National Center for Biotechnology Information's website. (See Tatiana A. Tatusova, Thomas L. Madden (1999), "Blast 2 sequences—a new tool for comparing protein and nucleotide sequences", FEMS Microbiol Lett. 174:247-250). Such a pair of nucleic acids may show, for example, at least 60%, at least 70%, at least 80%, at least 85%, at least 90%, at least 91%, at least 92%, at least 93%, at least 94%, at least 95%, at least 96%, at least 97%, at least 98%, or at least 99% or greater sequence identity over a certain defined length.

Nucleic acid sequences that do not show a high degree of identity may nevertheless encode similar amino acid sequences due to the degeneracy of the genetic code where multiple codons may encode for a single amino acid. It is understood that changes in a nucleic acid sequence can be made using this degeneracy to produce multiple nucleic acid sequences that all encode substantially the same protein. For example, polynucleotide sequences as contemplated herein may encode a protein and may be codon-optimized for expression in a particular host. In the art, codon usage frequency tables have been prepared for a number of host organisms including humans, mouse, rat, pig, E. coli, plants, and other host cells.

A "recombinant nucleic acid" is a sequence that is not naturally occurring or has a sequence that is made by an artificial combination of two or more otherwise separated segments of sequence. This artificial combination is often accomplished by chemical synthesis or, more commonly, by the artificial manipulation of isolated segments of nucleic acids, e.g., by genetic engineering techniques known in the art. The term recombinant includes nucleic acids that have been altered solely by addition, substitution, or deletion of a portion of the nucleic acid. Frequently, a recombinant nucleic acid may include a nucleic acid sequence operably linked to a promoter sequence. Such a recombinant nucleic acid may be part of a vector that is used, for example, to transform a cell.

The nucleic acids disclosed herein may be "substantially isolated or purified." The term "substantially isolated or purified" refers to a nucleic acid that is removed from its natural environment, and is at least 60% free, preferably at least 75% free, and more preferably at least 90% free, even more preferably at least 95% free from other components with which it is naturally associated.

"Transformation" or "transfected" describes a process by which exogenous nucleic acid (e.g., DNA or RNA) is introduced into a recipient cell. Transformation or transfection may occur under natural or artificial conditions according to various methods well known in the art, and may rely on any known method for the insertion of foreign nucleic acid sequences into a prokaryotic or eukaryotic host cell.

The method for transformation or transfection is selected based on the type of host cell being transformed and may include, but is not limited to, bacteriophage or viral infection or non-viral delivery. Methods of non-viral delivery of nucleic acids include lipofection, nucleofection, microinjection, electroporation, heat shock, particle bombardment, biolistics, virosomes, liposomes, immunoliposomes, polycation or lipid:nucleic acid conjugates, naked DNA, artificial virions, and agent-enhanced uptake of DNA. Lipofection is described in e.g., U.S. Pat. Nos. 5,049,386, 4,946,787; and 4,897,355) and lipofection reagents are sold commercially (e.g., Transfectam™ and Lipofectin™). Cationic and neutral lipids that are suitable for efficient receptor-recognition lipofection of polynucleotides include those of Felgner, WO 91/17424; WO 91/16024. Delivery can be to cells (e.g. in vitro or ex vivo administration) or target tissues (e.g. in vivo administration). The term "transformed cells" or "transfected cells" includes stably transformed or transfected cells in which the inserted DNA is capable of replication either as an autonomously replicating plasmid or as part of the host chromosome, as well as transiently transformed or transfected cells which express the inserted DNA or RNA for limited periods of time.

The polynucleotide sequences contemplated herein may be present in expression vectors. For example, the vectors may comprise: (a) a polynucleotide encoding an ORF of a protein; (b) a polynucleotide that expresses an RNA that directs RNA-mediated binding, nicking, and/or cleaving of a target DNA sequence; and both (a) and (b). The polynucleotide present in the vector may be operably linked to a prokaryotic or eukaryotic promoter. "Operably linked" refers to the situation in which a first nucleic acid sequence is placed in a functional relationship with a second nucleic acid sequence. For instance, a promoter is operably linked to a coding sequence if the promoter affects the transcription or expression of the coding sequence. Operably linked DNA sequences may be in close proximity or contiguous and, where necessary to join two protein coding regions, in the same reading frame. Vectors contemplated herein may comprise a heterologous promoter (e.g., a eukaryotic or prokaryotic promoter) operably linked to a polynucleotide that encodes a protein. A "heterologous promoter" refers to a promoter that is not the native or endogenous promoter for the protein or RNA that is being expressed. For example, a heterologous promoter for a LAMP may include a eukaryotic promoter or a prokaryotic promoter that is not the native, endogenous promoter for the LAMP.

As used herein, "expression" refers to the process by which a polynucleotide is transcribed from a DNA template (such as into and mRNA or other RNA transcript) and/or the process by which a transcribed mRNA is subsequently translated into peptides, polypeptides, or proteins. Transcripts and encoded polypeptides may be collectively referred to as "gene product." If the polynucleotide is derived from genomic DNA, expression may include splicing of the mRNA in a eukaryotic cell.

The term "vector" refers to some means by which nucleic acid (e.g., DNA) can be introduced into a host organism or host tissue. There are various types of vectors including plasmid vector, bacteriophage vectors, cosmid vectors, bacterial vectors, and viral vectors. As used herein, a "vector" may refers to a recombinant nucleic acid that has been engineered to express a heterologous polypeptide (e.g., the fusion proteins disclosed herein). The recombinant nucleic acid typically includes cis-acting elements for expression of the heterologous polypeptide.

Any of the conventional vectors used for expression in eukaryotic cells may be used for directly introducing DNA into a subject. Expression vectors containing regulatory elements from eukaryotic viruses may be used in eukaryotic expression vectors (e.g., vectors containing SV40, CMV, or retroviral promoters or enhancers). Exemplary vectors include those that express proteins under the direction of such promoters as the SV40 early promoter, SV40 later promoter, metallothionein promoter, human cytomegalovirus promoter, murine mammary tumor virus promoter, and Rous sarcoma virus promoter. Expression vectors as contemplated herein may include eukaryotic or prokaryotic control sequences that modulate expression of a heterologous protein (e.g. the fusion protein disclosed herein). Prokaryotic expression control sequences may include constitutive or inducible promoters (e.g., T3, T7, Lac, trp, or phoA), ribosome binding sites, or transcription terminators.

The vectors contemplated herein may be introduced and propagated in a prokaryote, which may be used to amplify copies of a vector to be introduced into a eukaryotic cell or as an intermediate vector in the production of a vector to be introduced into a eukaryotic cell (e.g. amplifying a plasmid as part of a viral vector packaging system). A prokaryote may be used to amplify copies of a vector and express one or more nucleic acids, such as to provide a source of one or more proteins for delivery to a host cell or host organism. Expression of proteins in prokaryotes may be performed using *Escherichia coli* with vectors containing constitutive or inducible promoters directing the expression of either a protein or a fusion protein comprising a protein or a fragment thereof. Fusion vectors add a number of amino acids to a protein encoded therein, such as to the amino terminus of the recombinant protein. Such fusion vectors may serve one or more purposes, such as: (i) to increase expression of recombinant protein; (ii) to increase the solubility of the recombinant protein; (iii) to aid in the purification of the recombinant protein by acting as a ligand in affinity purification (e.g., a His tag); (iv) to tag the recombinant protein for identification (e.g., such as Green fluorescence protein (GFP) or an antigen (e.g., HA) that can be recognized by a labelled antibody); (v) to promote localization of the recombinant protein to a specific area of the cell (e.g., where the protein is fused (e.g., at its N-terminus or C-terminus) to a nuclear localization signal (NLS) which may include the NLS of SV40, nucleoplasmin, C-myc, M9 domain of hnRNP A1, or a synthetic NLS). The importance of neutral and acidic amino acids in NLS have been studied. (See Makkerh et al. (1996) *Curr Biol* 6(8):1025-1027). Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase.

The presently disclosed methods may include delivering one or more polynucleotides, such as or one or more vectors as described herein, one or more transcripts thereof, and/or one or proteins transcribed therefrom, to a host cell. Further contemplated are host cells produced by such methods, and organisms (such as animals, plants, or fungi) comprising or produced from such cells. The disclosed extracellular vesicles may be prepared by introducing vectors that express mRNA encoding a fusion protein and a cargo RNA as disclosed herein. Conventional viral and non-viral based gene transfer methods can be used to introduce nucleic acids in mammalian cells or target tissues. Non-viral vector delivery systems include DNA plasmids, RNA (e.g. a transcript of a vector described herein), naked nucleic acid, and nucleic acid complexed with a delivery vehicle, such as a liposome. Viral vector delivery systems include DNA and RNA viruses, which have either episomal or integrated genomes after delivery to the cell.

In the methods contemplated herein, a host cell may be transiently or non-transiently transfected (i.e., stably transfected) with one or more vectors described herein. In some embodiments, a cell is transfected as it naturally occurs in a subject (i.e., in situ). In some embodiments, a cell that is transfected is taken from a subject (i.e., explanted). In some embodiments, the cell is derived from cells taken from a subject, such as a cell line. Suitable cells may include stem cells (e.g., embryonic stem cells and pluripotent stem cells). A cell transfected with one or more vectors described herein may be used to establish a new cell line comprising one or more vector-derived sequences. In the methods contemplated herein, a cell may be transiently transfected with the components of a system as described herein (such as by transient transfection of one or more vectors, or transfection with RNA), and modified through the activity of a complex, in order to establish a new cell line comprising cells containing the modification but lacking any other exogenous sequence.

EXAMPLES

The following Examples are illustrative and are not intended to limit the scope of the claimed subject matter.

Example 1—A Targeted and Modular Exosome Loading (TAMEL) System

Reference is made to U.S. Published Patent Application No. 2015/0093433, published on Apr. 2, 2015, and Hung and Leonard, "A platform for actively loading cargo RNA to elucidate limiting steps in EV-mediated delivery," *J. Extracellular Vesicles,* 2016, 5: 31027, published 13 May 2016, the contents of which are incorporated herein by reference in their entireties.

Abstract

Figure 2:
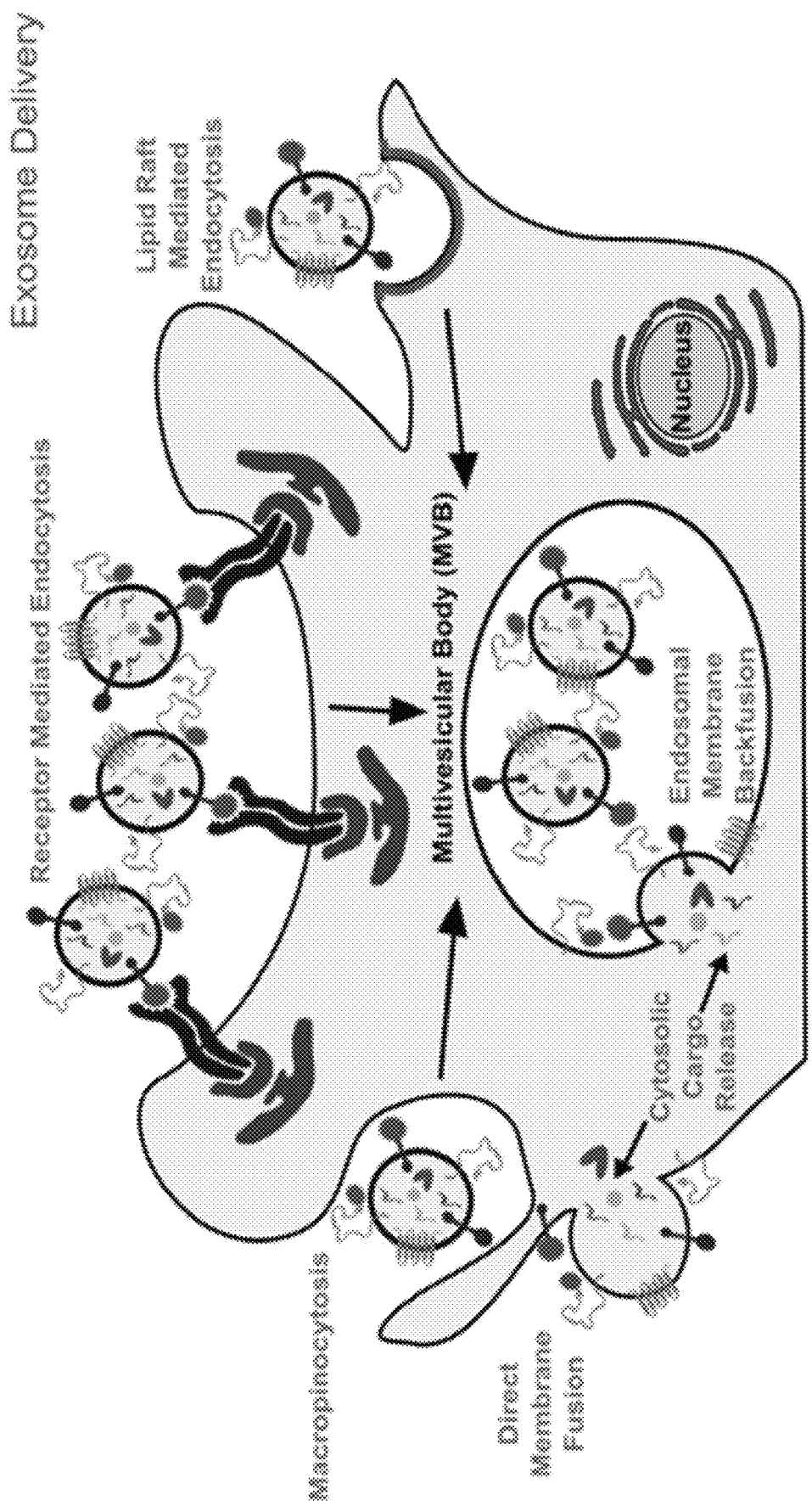
FIG. 2. Exosome Delivery: Exosomes are taken up by recipient cells by a variety of mechanisms, and exosome cargo is delivered to the cytoplasm of the recipient cell, where it is functional.

This Example relates to a Targeted and Modular Exosome Loading (TAMEL) system, which is a technology for directing the loading of RNA into exosomes. Secreted extracellular vesicles are emerging as important new features of the expanding landscape of intercellular communication. The process of secretion of exosomes by an exosome-producing cell and the process of uptake of the secreted exosomes by a recipient cell are illustrated schematically in FIGS. 1 and 2. A subset of extracellular vesicles in the 30-200 nanometer diameter range, known as exosomes, have been found to play a number of important roles in intercellular signaling, including shedding of obsolete proteins during reticulocyte maturation [1], presentation of antigens to T cells [2], activation of B and T cell proliferation [3], and induction of immune rejection of murine tumors, presumably by delivery or presentation of tumor antigens to the immune system [4]. Exosomes have generated great interest for their roles in intercellular communication and their potential to therapeutically modulate immune cell signaling. Subsequent investigations into exosome biogenesis, cargo packaging, and mediation of intercellular communication have identified new opportunities for harnessing and modifying exosomes to develop exosome-based therapeutics.

The TAMEL system disclosed here utilizes a "packaging protein" and a "cargo RNA." The "packaging protein" may be referred to as a EV-loading protein. (See Hung and Leonard, "A platform for actively loading cargo RNA to elucidate limiting steps in EV-mediated delivery," *J. Extracellular Vesicles,* 2016, 5: 31027, published 13 May 2016, the content of which is incorporated herein by reference in its entirety.) The packaging protein is an RNA-binding protein targeted to exosomes via fusion to an exosome-targeted domain of a lysosomal protein. The cargo RNA is an RNA molecule displaying the proper RNA-motif for binding by the packaging protein. This packaging system is novel in that it is the first method by which any type of RNA (e.g., miRNA, shRNA, mRNA, ncRNA) can be targeted for loading into exosomes via fusion to the RNA-motif, without the need for overexpression of the RNA of interest. Overexpression generally is disfavored because it can alter the physiology of the exosome-producing cell. The ability to selectively enrich RNAs in exosomes is essential to the engineering of exosomes as therapeutic delivery vehicles. RNA-loaded exosomes have a wide variety of potential therapeutic uses and are already being investigated as delivery vehicles for gene therapy, vaccines, and reprogramming factors in the generation of pluripotent stem cells. However, the therapeutic utility of exosomes is hampered by a general lack of control over which molecules are loaded from the parent cell into the exosomes. The technology disclosed herein provides the capability to control which RNA species are most abundant in exosomes.

DESCRIPTION

In this example, the TAMEL packaging protein consists of an RNA-binding protein fused to Lamp2b. Lamp2b has been previously shown to localize to exosomes [5]. Alvarez-Erviti et al. determined the orientation of Lamp2b in exosomes (N-terminus on the exterior of exosomes, C-terminus on the interior of exosomes) and showed that peptides fused to the N-terminus of Lamp2b could be displayed on the outside of exosomes [5]. (See FIG. 3 for schematic examples of Lamp2b fusion proteins for expressing a protein of interest on the surface of an exosome versus the lumen of the exosome). To direct the loading of RNA into the lumen of the exosome, we fused an RNA-binding protein to the C-terminus of Lamp2b. (See FIG. 4). We have tested the system using RNA-binding proteins that have been previously characterized, including bacteriophage coat proteins from the MS2 and LambaN bacteriophages [6].

The TAMEL system of this Example may be implemented as follows: (a) an RNA-binding protein, such as a bacteriophage coat protein, is chosen; (b) a packaging protein comprising Lamp2b on the N-terminus and the RNA-binding protein on the C-terminus is designed (see FIG. 4); (c) cargo RNA containing the packaging protein binding motif is designed (see FIG. 4); (d) DNA sequences encoding the packaging protein and cargo RNA are generated (by molecular biology and/or DNA synthesis) and inserted into a suitable expression vector (e.g., viral vector for cargo RNA, plasmid or viral vector for packaging protein); (e) the cargo RNA expression vector is transduced into a suitable cell for producing RNA (or RNA is produced in vitro and transduced into a suitable cell for producing exosomes) and the packaging protein vector is transfected or transduced into a suitable cell line for producing exosomes; (f) exosomes are harvesting from the cell line producing the exosomes; and (g) RNA is isolated from these exosomes and quantified by qPCR.

The mode of action of the TAMEL system is that the packaging protein fused to Lamp2b is capable both of localizing to exosomes through its Lamp2b domain and binding RNA through its RNA-binding domain. During the process of exosome biogenesis, the RNA-binding domain is initially localized in the cytoplasm, where it has access to cytoplasmic RNA species, including the cargo RNA. The inward budding of the multivesicular body (MVB) membrane to form intraluminal vesicles (ILVs), results in the RNA-binding domain localizing in the lumen of ILVs. Bound RNA should move in concert with the RNA-binding domain, also localizing to the ILV lumen. As ILVs are released from the exosome-producing cell, as exosomes, the RNA-binding domain and bound RNA remain in the vesicle lumen, ultimately resulting in their presence in the lumen of exosomes. (See FIG. 1). After being released from an exosome-producing cell, the exosomes may be delivered to a target cell (i.e., recipient cell) where the exosomes are taken up and the exosome cargo is delivered to the cytoplasm of the target cell. (See FIG. 2).

Figure 5:
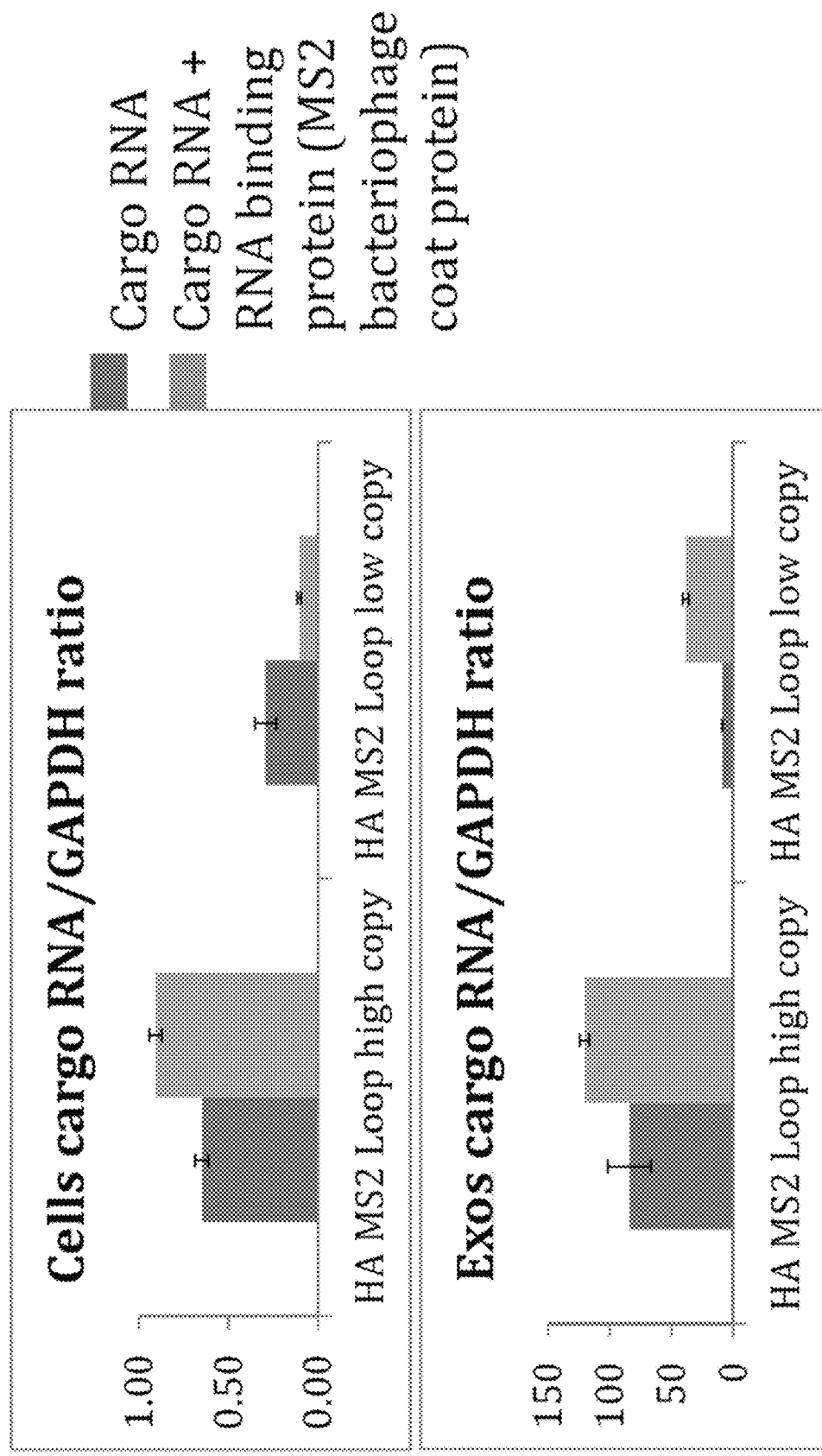
FIG. 5. Packaging of cargo RNA comprising the MS2 RNA packaging signal into exosomes in the presence of a fusion protein comprising the MS2 coat protein RNA-binding domain FIG. 6. Packaging of long cargo RNA into exosomes in the presence of TAMEL packaging protein.
Figure 6:
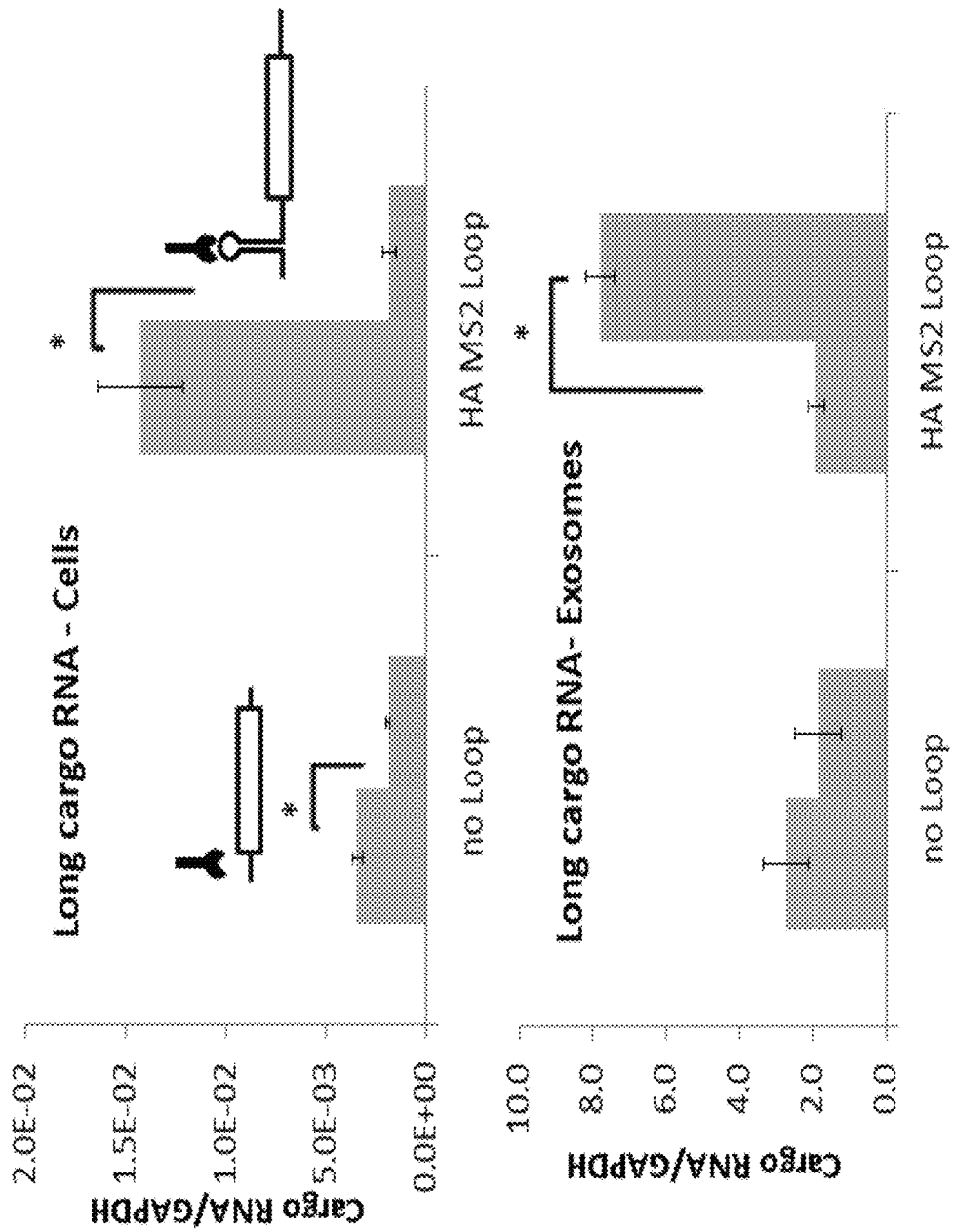

As illustrated in FIG. 5, cargo RNA bearing the MS2 RNA-binding loop was transduced into cells at high or low copy number, either in the presence or absence of the TAMEL packaging protein bearing the RNA-binding domain of the coat protein of MS2. The cargo RNA was a 187 base pair small RNA displaying the high affinity MS2 binding loop (HA MS2 Loop). The cargo RNA was transduced into cells at high copy or low copy number for high or low expression, respectively. Cargo RNA levels were normalized to GAPDH reference RNA in (top) cells and (bottom) exosomes. An observed increase in cargo RNA level in exosomes was significant by a student's t-test at a p-value of 0.05. Therefore, the TAMEL system increased the incorporation of a small (~190 bp) RNA into exosomes. In the presence of the Lamp2b-MS2 TAMEL packaging protein, the small cargo RNA level increased 1.4-4.4 fold in exosomes compared to no TAMEL packaging protein.

Figure 4:
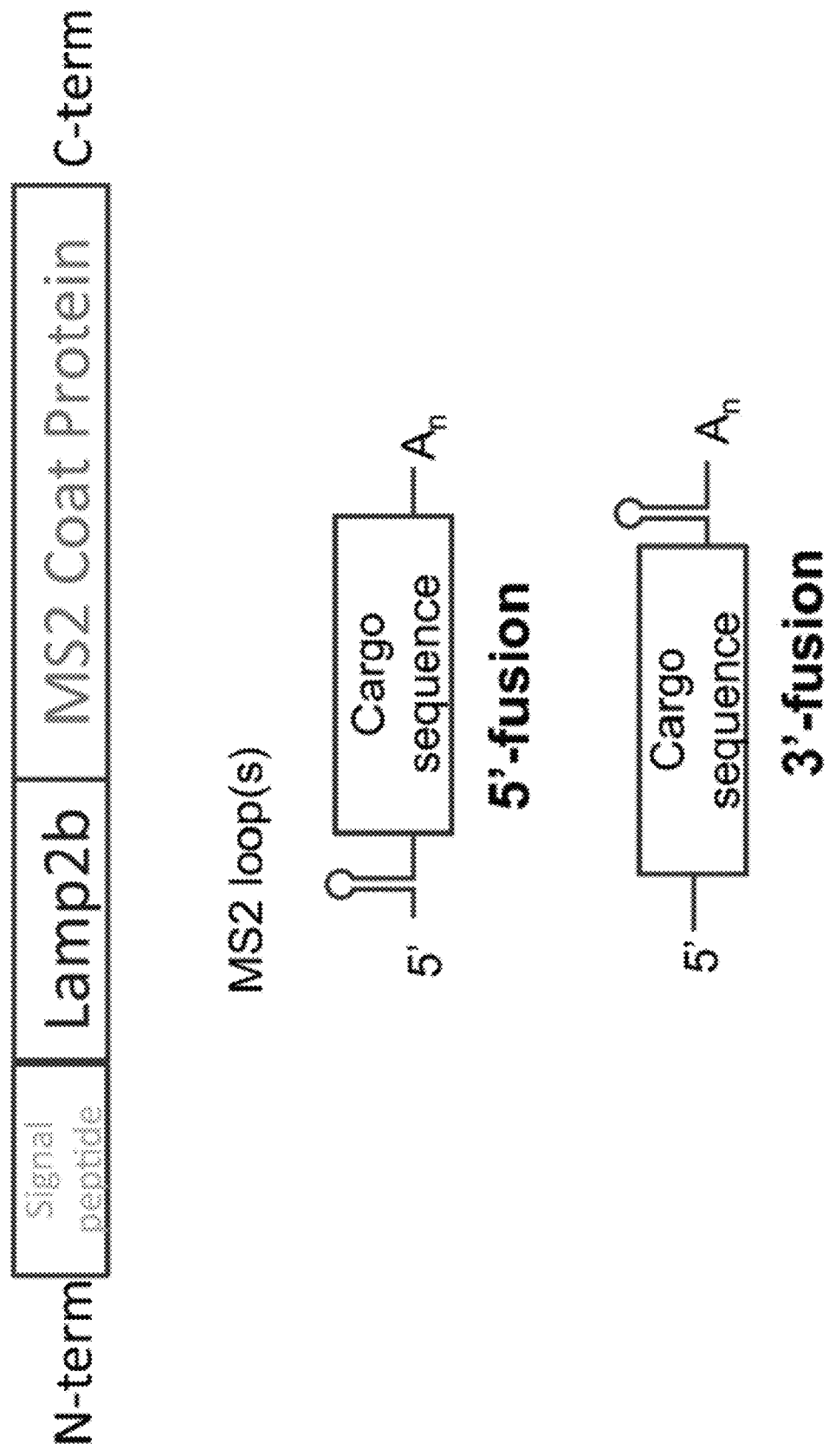
FIG. 4. Schematic representation of one embodiment of a packaging protein and cargo RNA as contemplated herein. The packaging protein is a fusion protein comprising from N-terminus to C-terminus: a signal peptide, at least a portion of LAMP2b comprising the exosome-targeting domain, and at least a portion of the MS2 coat protein comprising the RNA-binding domain. The cargo RNA comprises the high affinity binding loop of MS2 RNA fused at the 5'-terminus (top) or 3'-terminus (bottom) of a cargo sequence of interest.

To investigate whether "longer" cargo RNA could be incorporated into exosomes using the TAMEL system, we engineered lentiviral vectors driving expression of cargo RNA (~1700 nt plus 100-250 poly-A) via RNA Pol II. These cargo RNAs had either no MS2 binding loop or a high affinity MS2 binding loop, facilitating the cargo RNA to be bound by the Lamp2b-MS2 TAMEL packaging protein. We transfected cell lines with the Lamp2b-MS2 TAMEL packaging protein or a negative control protein (Lamp2b-neg). (See FIG. 4). Despite the fact that the cells transfected with the TAMEL packaging protein had lower levels of cargo RNA than those transfected with the negative control protein (FIG. 4, top), the presence of the TAMEL packaging protein increased the incorporation of the cargo RNA into exosomes by about 7 fold (FIG. 4, bottom versus top). These results indicate that the TAMEL system can be applied to package large RNAs into exosomes.

Discussion

The TAMEL system disclosed here offers advantages over two existing methods for enriching RNAs in exosomes: (1) overexpression and (2) RNA zipcodes [7]. Overexpression is a commonly utilized strategy for incorporating RNA into exosomes which comprises simply overexpressing the cargo RNA in the exosome-producing cells. This method potentially utilizes a mass action driving force to promote non-specific incorporation of cargo RNA into exosomes. Such cargo RNA overexpression in producer cells has been used to incorporate miRNA [8], [9], [10], chemically modified 3' benzen-pyridine miRNA [11], shRNA [9], and mRNA [12], [13] into exosomes. Upon incubation of exosomes carrying these RNAs with recipient cells, these overexpressed RNAs were all functional (i.e. the mRNA was translated into protein, and the shRNAs and miRNAs induced target gene knockdown). This strategy thus appears to be broadly applicable to a variety of RNA cargos and recipient cell types.

Nonetheless, this technique has not been explored broadly enough to determine whether it is robust and widely applicable. The observation that some RNA species that are highly abundant in cells are not present in the exosomes produced from those cells [14], [15], [16], [17] suggests that this strategy may have varying degrees of success for different types of RNA, and indeed may be incapable of mediating the packaging of RNAs that may be actively excluded from exosomes. Furthermore, overexpression of RNA can impact host cell physiology, causing changes in cell health, or possibly changes in exosome production itself. These effects may hinder the packaging of certain RNAs into exosomes, for example therapeutic RNAs intended to induce apoptosis in cancer cells. In contrast, the described TAMEL system is not dependent on high expression levels of the cargo RNA. In fact, the platform could be engineered for greater sensitivity to RNAs that are expressed only at low levels (for example, by engineering higher affinity RNA-binding domains). Furthermore, because TAMEL is independent of host packaging mechanisms, it is capable of loading any RNA into exosomes, even RNAs that have been observed to be excluded from exosomes.

RNA zipcodes refer to structural and sequence motifs that have been identified as enriched in exosomes, and may be utilized to direct the loading of RNA into exosomes. For example, deep sequencing of exosome RNA revealed that miRNAs with 3' modifications are enriched in exosomes [18]. Potentially, 3' modification of miRNA could be used to load specific miRNAs into exosomes, but this has not been tested. In the case of mRNA, however, RNA zipcodes have been used to enrich mRNA in exosomes. RNA zipcodes are sequence motifs in the 3' untranslated region (UTR) that direct mRNA localization within the cell. Bolukbasi et al. identified two features—a miR-1289 binding site and a core "CTGCC" motif—that are enriched in the 3' UTRs of a large proportion of mRNAs found in glioblastoma- and melanoma-derived exosomes. Replacing the 3' UTR of eGFP with a 25 nucleotide sequence containing the miR-1289 binding site and the "CTGCC" motif added was sufficient to increase eGFP mRNA incorporation into HEK293T exosomes by 2-fold compared to untagged eGFP mRNA. Overexpression of miR-1289 further increased the incorporation of the construct 6-fold compared to the untagged eGFP mRNA. This increase in exosome targeting depended on the presence of the miR-1289 binding site, as mutation of this site abrogated enrichment of the mRNA in exosomes [7]. This approach to RNA loading applies only to mRNA, which contain a 3' UTR. Whether or not these zipcodes could be placed in non-coding and small RNAs to mediate loading into exosomes is unknown. Furthermore, overexpression of miR-1289 increases the levels of endogenous mRNAs containing miR-1289 binding sites loaded into exosomes [7] which could be undesirable for certain applications.

In contrast to these RNA-motifs, the TAMEL system can be applied to any type of RNA and does require interfering with native exosome loading mechanisms. As such, the TAMEL system is widely applicable. For example, the TAMEL system may be used: (a) to enrich exosomes with therapeutic RNA for use of exosomes as gene therapy delivery vehicles; (b) to enrich exosomes with RNA as part of an exosome vaccine; (c) to enrich exosomes with reprogramming RNAs for generating pluripotent stem cells; (d) to enrich exosomes with a specific RNA for delivering the RNA to recipient cells as an alternative to transfection or transduction; (e) to study and characterize the factors that affect loading of native RNA into exosomes via using the TAMEL system as a model and modifying various aspects of the TAMEL system to determine how the modifications affect RNA loading.

Notably, as demonstrated here, the present TAMEL system can be utilized to incorporate relatively long mRNAs. This result is important because this indicates that the TAMEL system will be useful for designing exosomes for delivering mRNAs to target cells, which could be useful in a variety of therapeutic applications.

REFERENCES

1. Johnstone, R. M., et al., Vesicle formation during reticulocyte maturation. Association of plasma membrane activities with released vesicles (exosomes). J Biol Chem, 1987. 262(19): p. 9412-20.
2. Raposo, G., et al., B lymphocytes secrete antigen-presenting vesicles. J Exp Med, 1996. 183(3): p. 1161-72.
3. Skokos, D., et al., Mast cell-dependent B and T lymphocyte activation is mediated by the secretion of immunologically active exosomes. J Immunol, 2001. 166(2): p. 868-76.
4. Zitvogel, L., et al., Eradication of established murine tumors using a novel cell-free vaccine: dendritic cell-derived exosomes. Nat Med, 1998. 4(5): p. 594-600.
5. Alvarez-Erviti, L., et al., Delivery of siRNA to the mouse brain by systemic injection of targeted exosomes. Nat Biotechnol, 2011. 29(4): p. 341-5.
6. Keryer-Bibens, C., C. Barreau, and H. B. Osborne, Tethering of proteins to RNAs by bacteriophage proteins. Biol Cell, 2008. 100(2): p. 125-38.
7. Bolukbasi, M. F., et al., miR-1289 and "Zipcode"-like Sequence Enrich mRNAs in Microvesicles. Mol Ther Nucleic Acids, 2012. 1: p. e10.
8. Ohno, S., et al., Systemically injected exosomes targeted to EGFR deliver antitumor microRNA to breast cancer cells. Mol Ther, 2013. 21(1): p. 185-91.
9. Rechavi, O., et al., Cell contact-dependent acquisition of cellular and viral nonautonomously encoded small RNAs. Genes Dev, 2009. 23(16): p. 1971-9.
10. Kosaka, N., et al., Competitive interactions of cancer cells and normal cells via secretory microRNAs. J Biol Chem, 2012. 287(2): p. 1397-405.
11. Akao, Y., et al., Microvesicle-mediated RNA molecule delivery system using monocytes/macrophages. Mol Ther, 2011. 19(2): p. 395-9.
12. Hergenreider, E., et al., Atheroprotective communication between endothelial cells and smooth muscle cells through miRNAs. Nat Cell Biol, 2012. 14(3): p. 249-56.
13. Mizrak, A., et al., Genetically engineered microvesicles carrying suicide mRNA/protein inhibit schwannoma tumor growth. Mol Ther, 2013. 21(1): p. 101-8.
14. Valadi, H., et al., Exosome-mediated transfer of mRNAs and microRNAs is a novel mechanism of genetic exchange between cells. Nat Cell Biol, 2007. 9(6): p. 654-9.
15. Montecalvo, A., et al., Mechanism of transfer of functional microRNAs between mouse dendritic cells via exosomes. Blood, 2012. 119(3): p. 756-66.
16. Iguchi, H., N. Kosaka, and T. Ochiya, Secretory microRNAs as a versatile communication tool. Commun Integr Biol, 2010. 3(5): p. 478-81.
17. Kucharzewska, P., et al., Exosomes reflect the hypoxic status of glioma cells and mediate hypoxia-dependent activation of vascular cells during tumor development. Proc Natl Acad Sci USA, 2013. 110(18): p. 7312-7.
18. Koppers-Lallic, D. H., M.; van Eijndhoven, M. E.; Sabogal Pineros, Y.; Sie, D.; Ylstra, B.; Middeldorp, J. M.; Pegtel, D. M., Comprehensive deep-sequencing analysis reveals non-random small RNA incorporation into tumour exosomes and biomarker potential. Journal of Extracellular Vesicles, 2013. 2: p. 20826.
19. Lotvall, J. O. V., H., Exosome transfer of nucleic acids to cells, USPTO, 2007.

Example 2—A CD63-MS2 Fusion Protein as an RNA Packaging Protein for Exosomes

We previously demonstrated that the exosome-targeting domain of the protein Lamp2b can be used as a packaging protein for exosomes. (See U.S. Published Application No. 20150093433, the content of which is incorporated herein by reference in its entirety). We showed that Lamp2b fused to MS2 significantly enhances cargo RNA loading into exosomes. In this Example, we found that CD63 protein also includes a potential exosome-targeting domain. CD63 fused to MS2 significantly enhances cargo RNA loading into exosomes.

The MS2 coat protein dimer used previously was genetically fused to the C-terminus of CD63, including a 7 amino acid flexible spacer between the CD63 C terminus and the MS2 dimer N terminus, and an human influenza hemagglutinin (HA) affinity tag was added to the C-terminus of MS2. The HA affinity tag does not affect the function of MS2 and was included to enable using Western blot experiments to verify the presence of this engineered protein in exosomes. A similar control construct was generated by fusing the HA affinity tag (alone) to CD63 in place of "MS2-HA".

Figure 7:
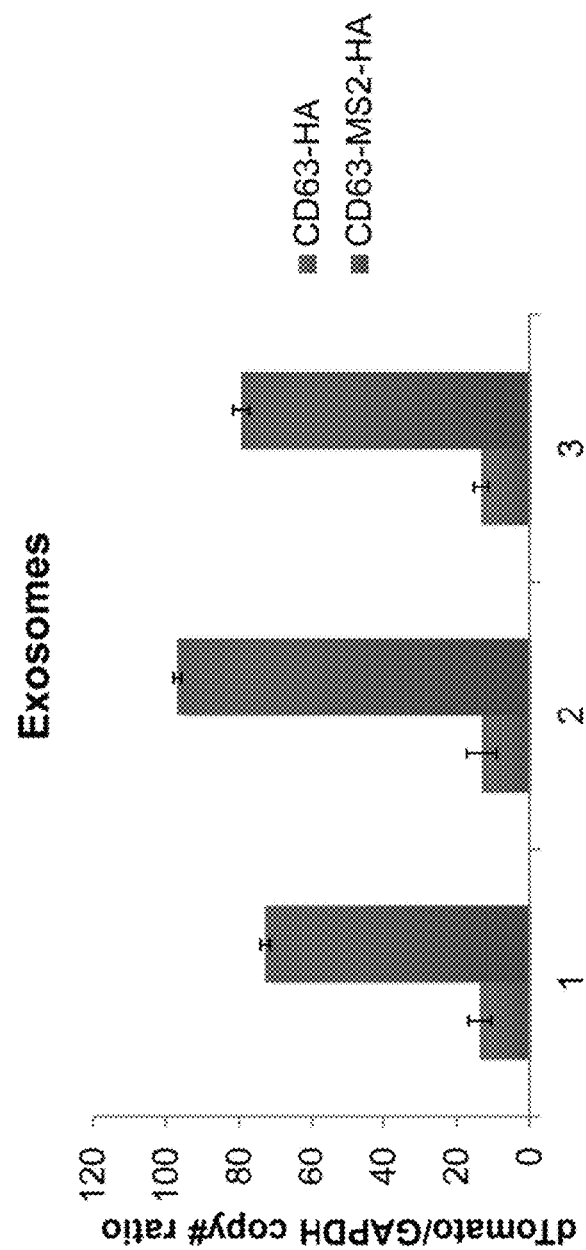
FIG. 7. Results of three experiments showing increased levels of dTomato cargo RNA in exosomes via CD63-MS2 active loading.

These proteins were expressed by transient transfection in the existing HEK293FT-based cell line, which constitutively expresses a dTomato-encoding cargo RNA that includes 3 MS2 binding loops in the 3' untranslated region. We then harvested exosomes from cells expressing the cargo RNA along with either CD63-MS2-HA or CD63-HA, and we used qPCR to determine the ratio of dTomato cargo RNA to GAPDH mRNA in the resulting exosome samples. This analysis revealed increased loading of the cargo RNA (per GAPDH mRNA) into exosomes when the exosome-producing cells expressed the CD63-MS2-HA protein rather than the CD63-HA control protein. (See FIG. 7).

Example 3—A VSVG-MS2 Fusion Protein as an RNA Packaging Protein for Exosomes

Cells transfected with Vesicular *Stomatis* Virus G protein (VSVG) produce extracellular vesicles called "gesicles." In this Example, we found that a VSVG-MS2 fusion significantly enhances cargo RNA loading into gesicles.

MS2-HA or HA was genetically fused to the C-terminus of VSVG in the same manner as was used to engineer CD63, as described above. Similar experiments were used to evaluated loading, except that the vesicles were harvested according to the protocol previously developed for harvesting vesicles containing VSVG ("gesicles") (See Mangeot et al., Molecular Therapy (2011) 19:9, 1656-1666).

Figure 8:
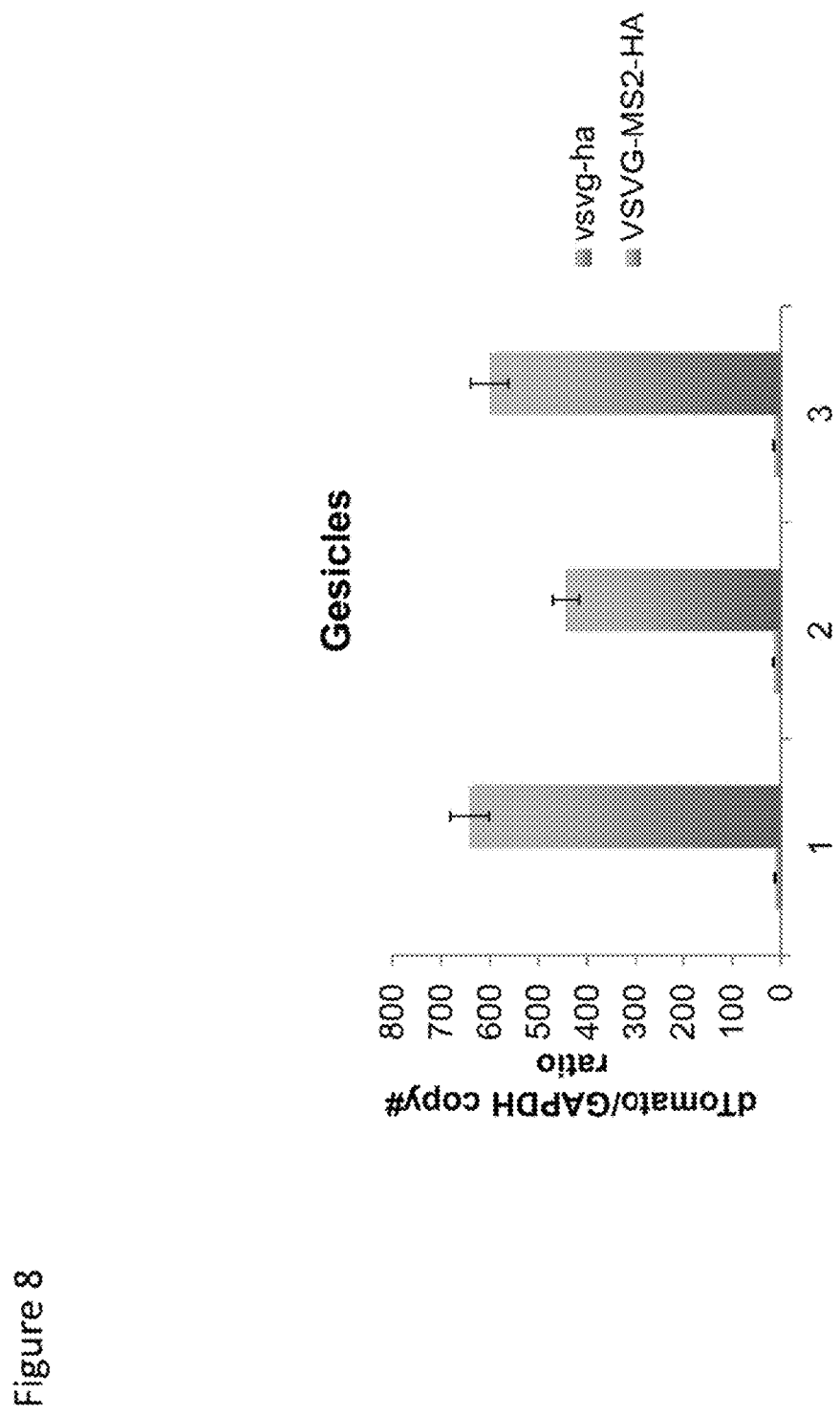
FIG. 8. Results of three experiments showing increased levels of dTomato cargo RNA in gesicles via VSVG-MS2 active loading.

Briefly, the difference between this protocol and the standard exosome purification protocol involved the use of centrifugation steps of different speeds and durations, such that potentially, a different pool of vesicles may be obtained. As observed for the CD63 experiments, expression of the VSVG-MS2-HA construct led to enhanced loading of the cargo RNA into vesicles (relative to cells expressing the VSVG-HA control protein). (See FIG. 8).

REFERENCES

1. Johnstone, R. M., et al., Vesicle formation during reticulocyte maturation. Association of plasma membrane activities with released vesicles (exosomes). J Biol Chem, 1987. 262(19): p. 9412-20.
2. Raposo, G., et al., B lymphocytes secrete antigen-presenting vesicles. J Exp Med, 1996. 183(3): p. 1161-72.
3. Skokos, D., et al., Mast cell-dependent B and T lymphocyte activation is mediated by the secretion of immunologically active exosomes. J Immunol, 2001. 166(2): p. 868-76.
4. Zitvogel, L., et al., Eradication of established murine tumors using a novel cell-free vaccine: dendritic cell-derived exosomes. Nat Med, 1998. 4(5): p. 594-600.
5. Alvarez-Erviti, L., et al., Delivery of siRNA to the mouse brain by systemic injection of targeted exosomes. Nat Biotechnol, 2011. 29(4): p. 341-5.
6. Keryer-Bibens, C., C. Barreau, and H. B. Osborne, Tethering of proteins to RNAs by bacteriophage proteins. Biol Cell, 2008. 100(2): p. 125-38.
7. Bolukbasi, M. F., et al., miR-1289 and "Zipcode"-like Sequence Enrich mRNAs in Microvesicles. Mol Ther Nucleic Acids, 2012. 1: p. e10.
8. Ohno, S., et al., Systemically injected exosomes targeted to EGFR deliver antitumor microRNA to breast cancer cells. Mol Ther, 2013. 21(1): p. 185-91.
9. Rechavi, O., et al., Cell contact-dependent acquisition of cellular and viral nonautonomously encoded small RNAs. Genes Dev, 2009. 23(16): p. 1971-9.
10. Kosaka, N., et al., Competitive interactions of cancer cells and normal cells via secretory microRNAs. J Biol Chem, 2012. 287(2): p. 1397-405.
11. Akao, Y., et al., Microvesicle-mediated RNA molecule delivery system using monocytes/macrophages. Mol Ther, 2011. 19(2): p. 395-9.
12. Hergenreider, E., et al., Atheroprotective communication between endothelial cells and smooth muscle cells through miRNAs. Nat Cell Biol, 2012. 14(3): p. 249-56.
13. Mizrak, A., et al., Genetically engineered microvesicles carrying suicide mRNA/protein inhibit schwannoma tumor growth. Mol Ther, 2013. 21(1): p. 101-8.
14. Valadi, H., et al., Exosome-mediated transfer of mRNAs and microRNAs is a novel mechanism of genetic exchange between cells. Nat Cell Biol, 2007. 9(6): p. 654-9.
15. Montecalvo, A., et al., Mechanism of transfer of functional microRNAs between mouse dendritic cells via exosomes. Blood, 2012. 119(3): p. 756-66.
16. Iguchi, H., N. Kosaka, and T. Ochiya, Secretory microRNAs as a versatile communication tool. Commun Integr Biol, 2010. 3(5): p. 478-81.
17. Kucharzewska, P., et al., Exosomes reflect the hypoxic status of glioma cells and mediate hypoxia-dependent activation of vascular cells during tumor development. Proc Natl Acad Sci USA, 2013. 110(18): p. 7312-7.
18. Koppers-Lallic, D. H., M.; van Eijndhoven, M. E.; Sabogal Pineros, Y.; Sie, D.; Ylstra, B.; Middeldorp, J. M.; Pegtel, D. M., Comprehensive deep-sequencing analysis reveals non-random small RNA incorporation into tumour exosomes and biomarker potential. Journal of Extracellular Vesicles, 2013. 2: p. 20826.
19. Lotvall, J. O. V., H., Exosome transfer of nucleic acids to cells, U.S. Published Patent Application No. 2007/0298118, 2007.
20. Hung, M. E. and Leonard, J., Stabilization of Exosome-targeting Peptides via Engineered Glycosylation, J. Biol. Chem., Vol. 290, NO. 13, pp. 8166-8172, Mar. 27, 2015.
21. Schulz, Chapter 2: Beyond the Sequon: Sites of N-Glycosylation, Biochemistry, Genetics and Molecular Biology "Glycosylation," edited by Stefana Petrescu, Sep. 26, 2012.
22. Bano-Polo, M., et al., N-Glycosylation efficiency is determined by the distance to the C-terminus and the amino acid preceding an Asn-Ser-Thr sequon, Protein Sci. 20, 179-186 (2011).
23. Kundra, R., et al., Asparagine-linked oligosaccharides protect Lamp-1 and Lamp-2 from intracellular proteolysis, J. Biol. Chem. 274, 31039-31046 (1999).

Example 5—Stabilization of Exosome-Targeting Peptides Via Engineered Glycosylation Reference is made to Hung, M. E. and Leonard, J., Stabilization of Exosome-targeting Peptides via Engineered Glycosylation, J. Biol. Chem., Vol. 290, NO. 13, pp. 8166-8172, Mar. 27, 2015, the content of which is incorporated herein by reference in its entirety.

Abstract

Exosomes are secreted extracellular vesicles that mediate intercellular transfer of cellular contents and are attractive vehicles for therapeutic delivery of bimolecular cargo such as nucleic acids, proteins, and even drugs. Efficient exosome-mediated delivery in vivo requires targeting vesicles for uptake by specific recipient cells. Although exosomes have been successfully targeted to several cellular receptors by displaying peptides on the surface of the exosomes, identifying effective exosome-targeting peptides for other receptors has proven challenging. Furthermore, the biophysical rules governing targeting peptide success remain poorly understood. To evaluate one factor potentially limiting exosome delivery, we investigated whether peptides displayed on the exosome surface are degraded during exosome biogenesis, for example by endosomal proteases. Indeed, peptides fused to the N terminus of exosome-associated transmembrane protein Lamp2b were cleaved in samples derived from both cells and exosomes. To suppress peptide loss, we engineered targeting peptide-Lamp2b fusion proteins to include a glycosylation motif at various positions. Introduction of this glycosylation motif both protected the peptide from degradation and led to an increase in overall Lamp2b fusion protein expression in both cells and exosomes. Moreover, glycosylation-stabilized peptides enhanced targeted delivery of exosomes to neuroblastoma cells, demonstrating that such glycosylation does not ablate peptide-target interactions. Thus, we have identified a strategy for achieving robust display of targeting peptides on the surface of exosomes, which should facilitate the evaluation and development of new exosome-based therapeutics.

Introduction

Lipid nanoparticles display many properties that make them excellent drug delivery vehicles, including the ability to enhance drug stability and solubility and alter drug pharmacokinetics to achieve higher drug concentrations in target tissues (1). Biologically derived nanoparticles are an emerging subset of lipid nanoparticles that have been shown to effectively deliver a wide range of functional biomolecules, evade or dampen immune responses, and accumulate in tumors (2-4). In particular, exosomes, which are endosomally derived secreted vesicles, have shown great promise as therapeutic delivery vehicles (5, 6). Exosomes have been used to deliver therapeutic RNA to neurons (7), ovarian cancers (8), glioblastomas (9), and colon cancers (10); to deliver proteins to glioblastomas (9); and to deliver small molecule drugs to breast cancers (11) and glioblastomas (12). Based on these successes, exosomes are now being investigated in clinical trials as delivery vehicles for cancer vaccines and small molecule drugs (13).

An attractive property of lipid nanoparticle-based drug delivery is the potential to target lipid nanoparticles for uptake by specific recipient cells by functionalizing these particles with ligands that bind receptors on recipient cells. The addition of targeting ligands to lipid nanoparticles enhances their uptake and retention in the desired recipient cell type or tissue. The addition of peptide-based targeting ligands to synthetic lipid nanoparticles is nontrivial as peptide ligands affect the stability and material properties of the lipid nanoparticle and increase the complexity of synthesis (14). In contrast, displaying targeting ligands on exosomes is relatively simple because peptide ligands can be genetically fused to the extra-exosomal termini of exosomal membrane proteins. This strategy has been applied to target exosome uptake by neurons by fusing a rabies viral glycoprotein (RVG)$^2$ peptide to the N terminus of lysosomal associated membrane protein 2b (Lamp2b) (7). Such a fusion resulted in RVG peptide being displayed on the surface of exosomes, leading to exosome uptake via the nicotinic acetylcholine receptor. Similarly, an internalizing RGD peptide fused to the N terminus of Lamp2b was used to target exosomes to breast cancer cells via $\alpha v \beta 3$ integrins (11). One alternative to Lamp2b, the transmembrane domain of platelet-derived growth factor receptor, has also been used as a fusion partner to display peptides on the surface of exosomes (8). However, it is not known whether such platelet-derived growth factor receptor fusion proteins localize to endosomally derived exosomes or rather to extracellular vesicles that bud from the plasma membrane. Finally, fusion of peptides to the C1C2 domain of lactadherin has been used to display peptides on the surface of exosomes for vaccines (15). However, lactadherin is a membrane-associated protein (16), not an integral membrane protein. Thus, peptides fused to lactadherin may be closely associated with the membrane, rather than freely accessible to interact with cell receptors.

Despite these successes, achieving efficient exosome targeting via surface display of targeting peptides is nontrivial. Although Alvarez-Erviti et al. (7) achieved neuronal targeting of exosomes via display of the RVG peptide, they were unable to achieve muscle targeting via display of a muscle-specific peptide similarly fused to Lamp2b. This suggests that different target-binding peptides may have different utility as exosome-targeting peptides, possibly due to variations in target binding affinity or level of peptide display on the exosome surface, or a combination of these factors. In this study, we demonstrate that some peptides fused to the N terminus of Lamp2b are not displayed effectively on the surface of exosomes. However, this display can be enhanced by introducing frequently glycosylated motifs at particular locations within the engineered fusion protein. We hypothesize that engineered glycosylation protects the targeting peptides from degradation in the endosomal system during exosome biogenesis and secretion. We also demonstrate that some glycosylation-protected peptides retain the ability to bind their target proteins and that this peptide protection strategy can be applied to targeting peptides displayed on the surface of exosomes.

Experimental Procedures

Plasmid Construction. Human Lamp2b cDNA was purchased from Open Biosystems and inserted into pcDNA3.1+ Hygro backbone. Peptide tags and glycine-serine amino acid spacers were added to the N and C termini of Lamp2b by PCR. The following tags were used: FLAG (DYKDDDDK), HA (YPYDVPDYA), and the glycosylation sequon (GNSTM) (17). Primer sequences are available upon request.

Cell Culture and Transfection. HEK293FT cells (Life Technologies) and Neuro2A cells (gift from Richard Morimoto) were maintained at 37° C. in 5% $CO_2$ in DMEM supplemented with 10% FBS, 1% penicillin-streptomycin, and 4 mm 1-glutamine HEK293FT cells were plated at ~60% confluency in 10- or 15-cm dishes, and 1-1.5 µg of DNA/ml was transfected using the $CaCl_2$-HEPES-buffered saline method.

Exosome Production and Characterization. Exosome-free medium was generated by pelleting FBS-derived exosomes from DMEM containing 20% FBS (see exosome pelleting protocol below) and combining the cleared supernatant with serum-free DMEM to achieve a final concentration of 10% FBS. HEK293FT cells were transfected with Lamp2b expression plasmids, and medium was changed to exosome-free medium 12-14 h after transfection. Conditioned medium was collected 2 days after medium change, and exosomes were concentrated by differential centrifugation. Conditioned medium was spun at 300×g for 10 min, 2,000×g for 10 min, and 10,000×g for 30 min to remove cells, cell debris, and apoptotic bodies. From this supernatant, exosomes were pelleted at 120,416×g for 135 min using an SW41 Ti rotor in an L-80 Optima XP ultracentrifuge (Beckman Coulter). Exosome pellets were washed in 10 ml of PBS and pelleted again via ultracentrifugation. Exosome morphology was evaluated by transmission electron microscopy using a 4% uranyl acetate negative stain. Exosome size distribution was profiled by NanoSight (Malvern) analysis.

Immunoblotting and Pulldown Assays. For Western blot analysis, cell extracts were prepared by lysis with radioimmunoprecipitation assay buffer. Exosomes were not lysed. Cell lysates, exosomes, and pulldowns were heated in Laemmli buffer at 70° C. Equal quantities of protein, as measured by BCA assay (Pierce), were loaded in each lane of a 4-15% gradient polyacrylamide gel (Bio-Rad). After transfer to a PVDF membrane (Bio-Rad), membranes were blocked for 1 h in 1% milk at room temperature, and then blotted with anti-HA (Cell Signaling Technology, C29F4), anti-FLAG (Abcam, ab1162), or anti-β-actin (Cell Signaling Technology, 8H10D10) antibodies. Primary antibodies were detected with horseradish peroxidase-conjugated anti-mouse (Invitrogen) or anti-rabbit (Invitrogen and Abcam) immunoglobulin G secondary antibody. For FLAG pulldown experiments, cell lysates or exosomes were precleared with Sepharose beads (Sigma) and then pulled down with FLAG M2 Sepharose beads (Sigma) and eluted with 3×FLAG peptide. When indicated, cell lysates were diluted 1:5 in TBS.

Inhibition of Endosomal Degradation. HEK293FT cells were transfected with Lamp2b expression plasmids. Cells were treated with 50 nm bafilomycin A1 (Sigma) or an equivalent amount of dimethyl sulfoxide (DMSO) for 9 h, or treated with 50 µm leupeptin (Sigma) for 24 h. Cells were then lysed and evaluated by immunoblotting as described above.

Measuring Exosome Uptake. After the first ultracentrifuge spin of the exosome isolation procedure described above, exosome pellets (~0.5 ml) were brought up to 1 ml in Diluent C (PKH67 kit, Sigma). This solution was mixed with 1 ml of Diluent C containing 6 µl of PKH67 dye and mixed via constant pipetting for 1 min Next, 2 ml of 1% BSA was added to halt staining. 4.5 ml of serum-free medium was added to bring the mixture up to 8.5 ml. Excess PKH67 dye can form micelles similar in size to exosomes, and these micelles cannot be separated from exosomes by ultracentrifugation alone (18). We observed that these micelles are less dense than exosomes (in 0.971 m sucrose, dye micelles float and exosomes pellet).[4] Thus, exosomes were purified via centrifugation through a 0.971 m sucrose cushion. Briefly, 1.5 ml of 0.971 m sucrose was slowly pipetted underneath the 8.5 ml of exosome solution containing BSA and excess dye. The entire mixture was centrifuged at 191,287×g for 2 h, and then the upper layer and interface were carefully aspirated. To generate a negative control for estimating uptake of dye micelles, 0.5 ml of serum-free medium was treated as an exosome pellet, labeled with PKH67, and subsequently processed exactly as were the exosome pellet samples. After purification through the sucrose cushion, exosomes were diluted 1:10 in PBS and re-concentrated in 100-kDa cut-off centrifugal filter units (Millipore UFC910024) to reduce the concentration of sucrose. Exosome concentration was then counted via Nano-Sight, and an equal number of exosomes from each sample (or all of the medium negative control, to be conservative) were added to Neuro2A recipient cells. Recipient cells were plated at 50% confluency in a 48-well plate. Exosomes and cells were incubated for 2 h at 37° C., as described (11). Cells were then washed with PBS and harvested for flow cytometry. Flow cytometry was performed on an LSRII flow cytometer (BD Bioscience) running FACSDiva software. Data were analyzed using FlowJo software (TreeStar). Live single cells were gated based upon scatter.

Results

Figure 9:
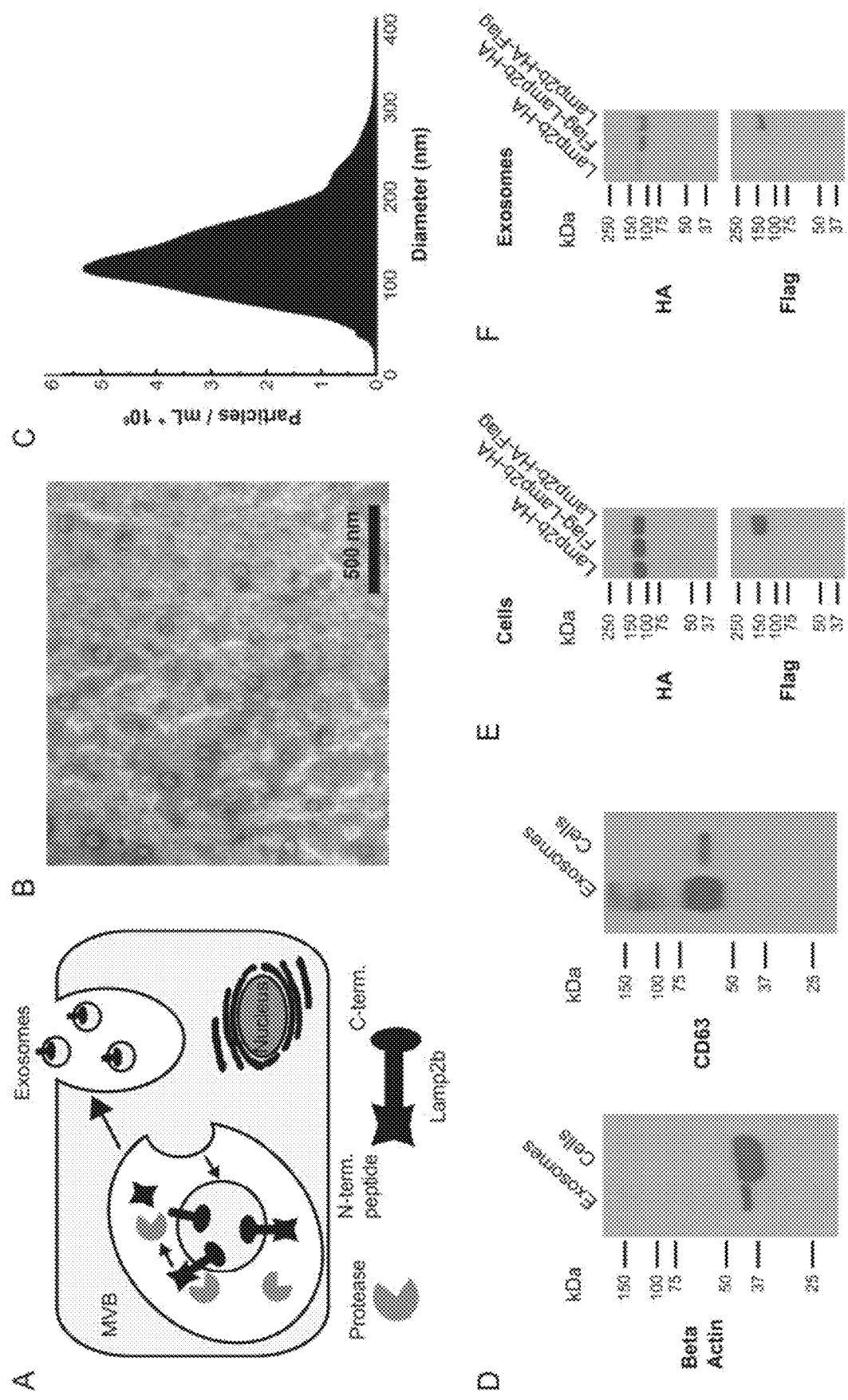
FIG. 9. Stability of exosome-targeting peptides. A, this graphic illustrates the orientation of Lamp2b in the endosomal membrane and exposure of N-terminal peptides (N-term. peptide) to proteases. MVB, multivesicular body. C.-term., C terminus. B, transmission electron microscopy image of exosomes isolated by differential centrifugation from HEK293FT cell supernatant. C, size distribution of exosomes secreted by HEK293FT cells. D, enrichment of exosome-associated protein CD63 in exosome preparations relative to β-actin. E and F, expression of Lamp2b fusion proteins in cell lysates (E) and exosomes (F), as evaluated by HA (C-terminal) and FLAG (N-terminal) Western blots.

Peptides Fused to the N Terminus of Lamp2b Are Not Detected in Cells and Exosomes. We hypothesized that peptides fused to the N terminus of Lamp2b would be vulnerable to proteolysis due to their localization in the lumen of endosomes (FIG. 9A). Indeed, when glycosylation is artificially inhibited, Lamp2b is also vulnerable to degradation by endosomal proteases (19). To test this hypothesis, HEK293FT cells were transfected with Lamp2b containing a C-terminal HA tag (Lamp2b-HA), two C-terminal tags (Lamp2b-HA-FLAG), or an N-terminal FLAG tag and a C-terminal HA tag (FLAG-Lamp2b-HA). Cell lysates and exosomes were harvested from these cells, and N- and C-terminal tags were analyzed by Western blots. Exosomes harvested from HEK293FT cells exhibited expected morphology and size (FIGS. 9, B and C). As compared with samples derived from whole cells, exosome samples were enriched in the exosomal protein CD63 relative to β-actin (FIG. 9D), as expected. The Lamp2b fusion proteins were expressed at similar levels in cells, as indicated by the HA Western blot. However, the FLAG peptide on FLAG-Lamp2b-HA could not be detected, although the C-terminal FLAG peptide of Lamp2b-HA-FLAG was detected (FIG. 9E). The same pattern was observed in exosomes (FIG. 9F). Together, these data indicate that the FLAG tag was lost from the N terminus of the Lamp2b protein.

Figure 10:
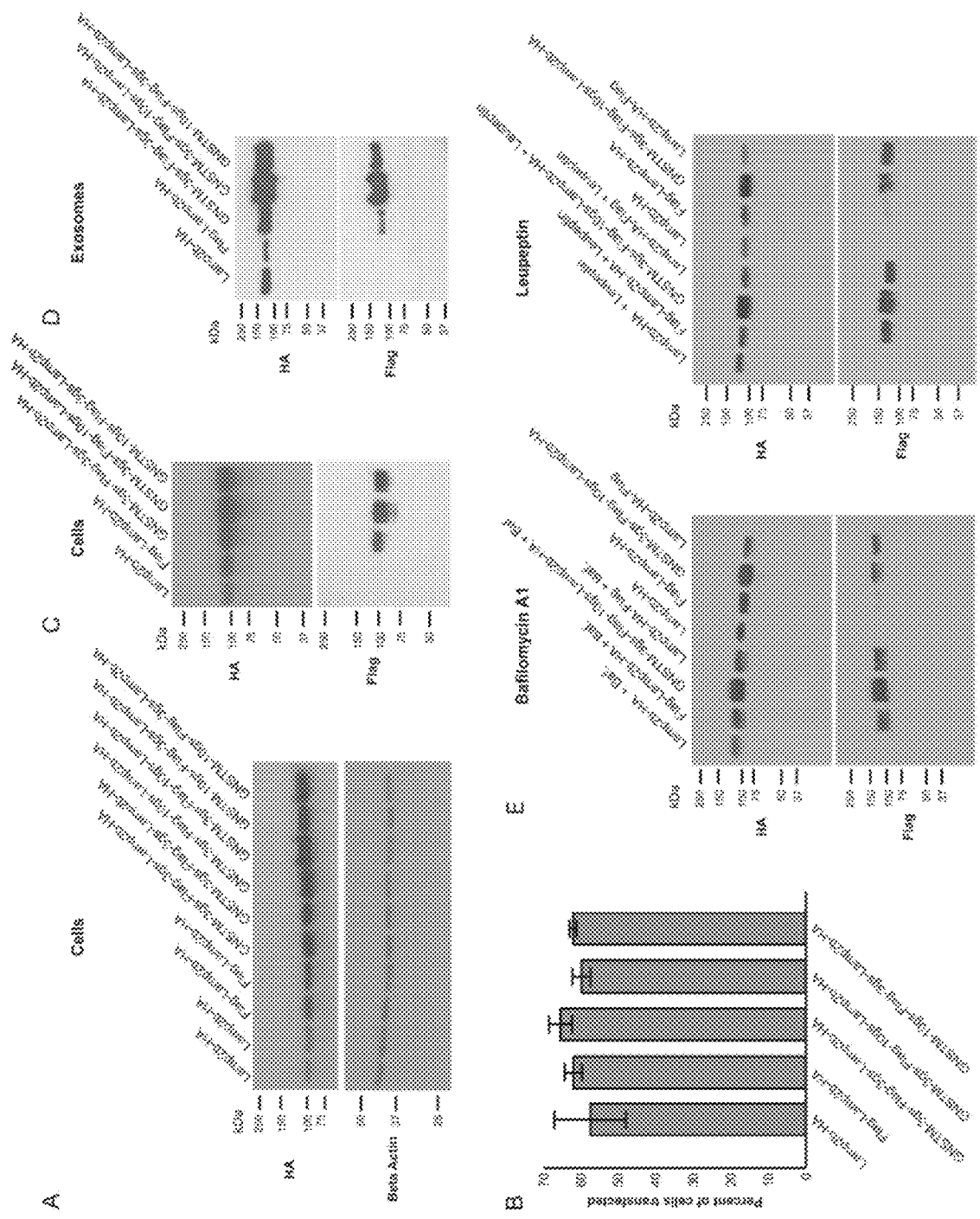
FIG. 10. Glycosylation motif-mediated stabilization of Lamp2b fusion proteins. A, expression of Lamp2b fusion proteins including an engineered GNSTM glycosylation motif in cells. In this and subsequent figures, the abbreviation "Xgs" is used to indicate a flexible linker X amino acids in length, comprising glycine and serine residues. B, transfection efficiency of cells expressing Lamp2b fusion proteins. Error bars indicate mean±S.D. C and D, expression of Lamp2b fusion proteins in cell lysates (C) and exosomes (D) measured by HA (C-terminal) and FLAG (N-terminal) Western blots. E, cells were treated with either bafilomycin A1 (Baf), which blocks endosomal acidification, or leupeptin, which inhibits endosomal proteases.

A Glycosylation Motif Protects Peptides on the N Terminus of Lamp2b and Enhances Expression of Lamp2b Fusion Proteins. Glycosylation of the Lamp2b protein protects it from proteolytic degradation (19). Therefore, we hypothesized that engineered glycosylation could also protect peptides fused to the N terminus of Lamp2b from proteolysis. To investigate, the amino acid sequence GNSTM was fused to the N terminus of FLAG-Lamp2b-HA. The NST sequence is a standard N-linked glycosylation sequon, and the amino acids G and M flanking the sequon may increase glycosylation frequency in mammals (11). To investigate how proximity to the GNSTM tag impacts targeting peptide stability and availability to bind cellular receptors, fusion proteins were engineered to include flexible amino acid spacers of various lengths between the GNSTM motif, the FLAG tag, and Lamp2b. Fusion protein expression was assessed in cells and exosomes. The GNSTM-tagged Lamp2b proteins accumulated to a greater level in cells than did Lamp2b-HA or FLAG-Lamp2b-HA (FIG. 10A), and this difference was not an artifact of differential transfection efficiency (FIG. 10B). The GNSTM-tagged Lamp2b proteins could also be detected by anti-FLAG Western blot in both cell lysates (FIG. 10C) and in exosomes (FIG. 10D). Notably, increased detection of the FLAG tag was not simply a consequence of increased protein expression (compare FLAG-Lamp2b-HA and GNSTM-3gs-FLAG-3gs-Lamp2b-HA in FIG. 10C, where 3gs indicates a flexible linker 3 amino acids in length comprising glycine and serine residues), although increased detection of the FLAG tag did correlate with increased protein expression. These results suggest that the GNSTM motif effectively confers protection of the N-terminal FLAG peptide. To test whether endosomal acidification was required for loss of the N-terminal FLAG peptide, cells were treated with bafilomycin A1. Bafilomycin A1 treatment preserved the FLAG peptide on FLAG-Lamp2b-HA but had no effect on either the FLAG peptide on the C terminus of Lamp2b-HA-FLAG or the glycosylated FLAG peptide. Inhibiting endosomal proteases with leupeptin yielded the same pattern (FIG. 10E). Together, these data confirm that peptides displayed on the N terminus of Lamp2b are degraded by acid-dependent proteolysis. Moreover, adding the GNSTM glycosylation motif protected such N-terminal peptides from this degradation.

Figure 11:
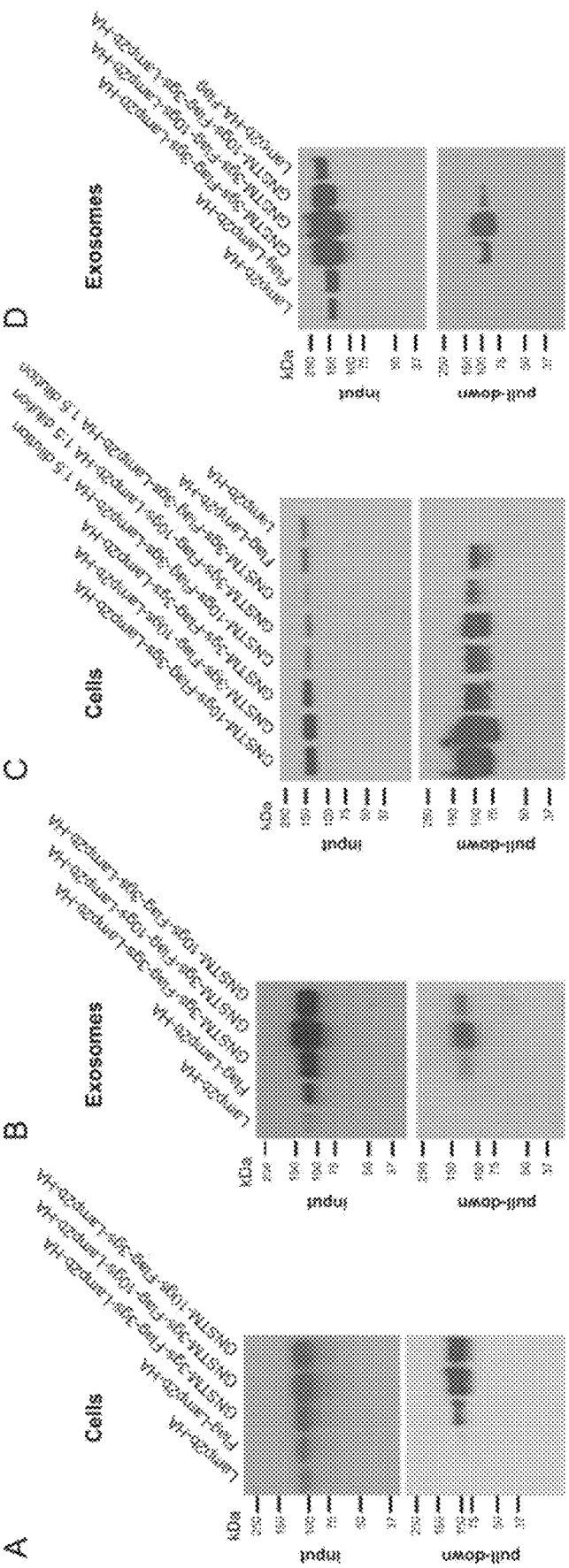
FIG. 11. Impact of engineered glycosylation motif on targeting peptide binding interactions. A and B, expression of FLAG-Lamp2b fusion proteins in cell lysates (A) and exosomes (B) before and after pulldown with anti-FLAG beads. C, lysates from cells expressing NST-tagged FLAG-Lamp2b proteins were diluted 1:5 in TBS (where indicated) and pulled down to confirm that apparent FLAG-mediated pulldown was not an artifact of variable levels of protein in the pulldown assay load. D, pulldown of intact exosomes requires that the FLAG tag be expressed on the Lamp2b N terminus (exosome exterior).

Peptides Protected by a Glycosylation Tag Retain the Capacity to Bind Cognate Peptide-binding Proteins. We next investigated whether GNSTM tag-stabilized peptide-Lamp2b fusion proteins retained the capacity to interact with binding partners. GNSTM-tagged FLAG-Lamp2b proteins were successfully pulled down by anti-FLAG beads in both cell lysates and intact exosomes (FIGS. 11, A and B). To verify that pulldown was FLAG-specific and not an artifact due to increased loading of the highly expressed GNSTM-tagged proteins, lysates from cells expressing GNSTM-tagged proteins were diluted 1:5 such that the amount of this Lamp2b fusion protein loaded into the pulldown was comparable with the amounts in FLAG-Lamp2b-HA and Lamp2b-HA samples. This pulldown indicated that the FLAG peptide was indeed necessary for pulldown (FIG. 11C). Moreover, FLAG-dependent pulldown efficiency was much greater for some GNSTM-tagged Lamp2b constructs as compared with the FLAG-Lamp2b-HA control. Also, pulldown of intact exosomes required that FLAG be on the exosome exterior because exosomes from cells expressing Lamp2b-HA-FLAG were not pulled down (FIG. 11D). Collectively, these results indicate that the GNSTM motif can protect targeting peptides fused to the N terminus of Lamp2b from degradation without precluding interactions between these peptides and their cognate protein targets.

Figure 12:
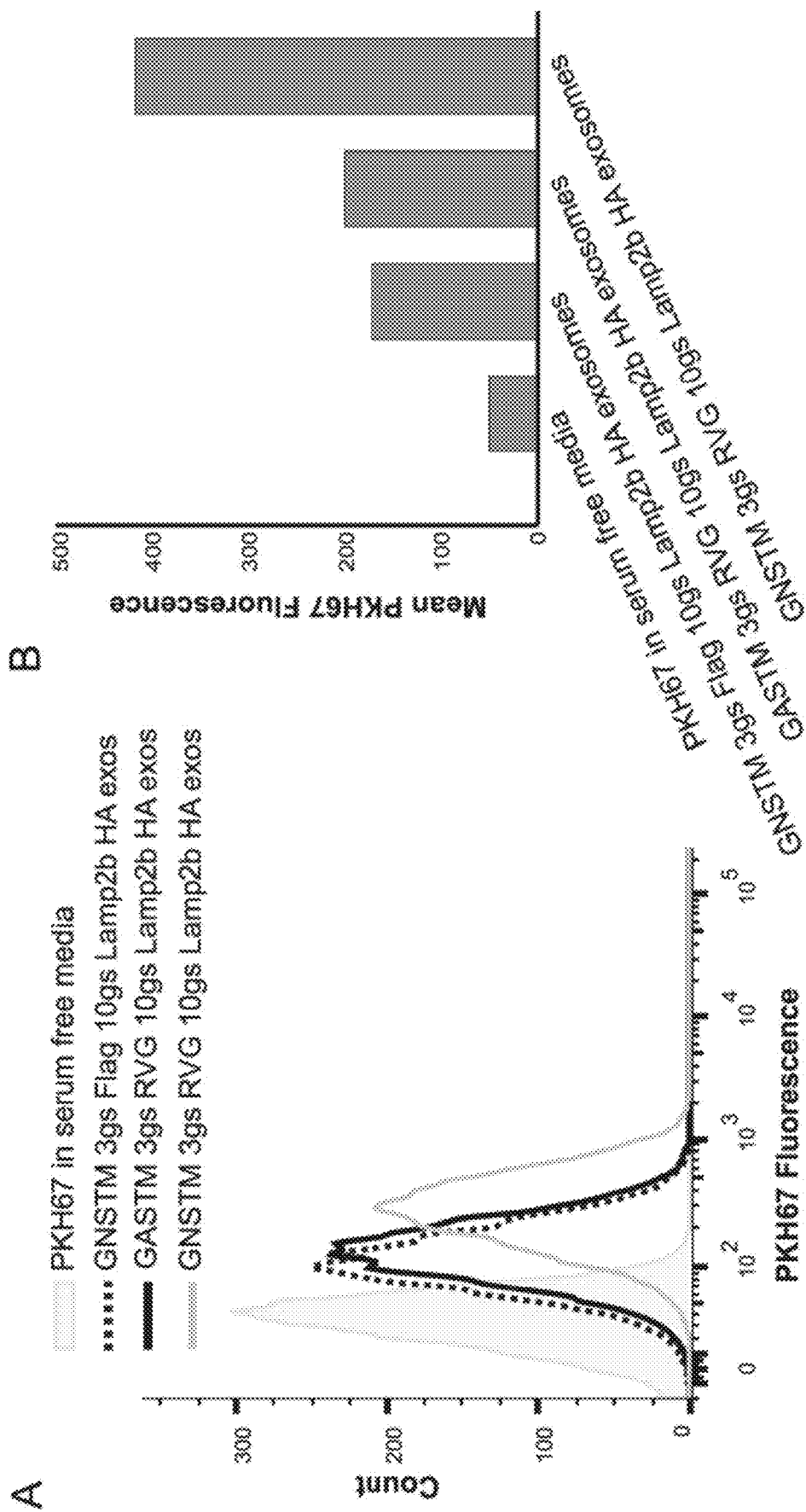
FIG. 12. Glycosylation-enhanced targeted delivery of exosomes to neuroblastoma cells. A, equivalent numbers of PHK67-labeled exosomes were incubated with Neuro2A cells for 2 h (~3×10$^9$ exosomes per 1×10$^5$ cells), and uptake was quantified by flow cytometry. The shaded histogram is the exosome-free negative control to evaluate excess dye and dye-derived micelles. exos, exosomes. B, quantification of peaks presented in panel A.

Targeting Peptides Protected by a Glycosylation Tag Enhance Exosome Uptake by Recipient Cells. We next evaluated whether our engineered glycosylation approach is compatible with a demonstrated exosome targeting strategy. To this end, we utilized the system described by Alvarez-Erviti et al. (7), in which display of the RVG peptide on exosomes mediated delivery to Neuro2A neuroblastoma cells. The RVG peptide was fused to the N terminus of Lamp2b along with either a GNSTM glycosylation motif or a mutated motif, GASTM, which is not glycosylated. Exosomes displaying GNSTM-FLAG-Lamp2b-HA were also included as negative controls. All exosomes were labeled with the lipophilic dye PKH67, and equal numbers of exosomes from each sample were incubated with Neuro2A cells for 2 h. Notably, uptake of GNSTM-RVG exosomes exceeded uptake of either GASTM-RVG or GNSTM-FLAG exosomes (FIGS. 12, A and B). Moreover, only the glycosylated RVG peptides mediated exosome uptake greater than was observed for negative control exosomes. Thus, in this system, engineered glycosylation of the targeting peptide did not prevent targeted exosome uptake, and indeed glycosylation was required to confer targeted exosome uptake.

Discussion

In this study, we found that peptides expressed on the N terminus of Lamp2b are susceptible to acid-dependent proteolytic degradation and that the glycosylation motif GNSTM protects such peptides from degradation. This strategy allows for the display of targeting peptides on the surface of exosomes. Furthermore, the GNSTM motif does not interfere with interactions between targeting peptides and their cognate protein targets. Indeed, in our hands, the GNSTM motif enhanced targeting peptide-mediated exosome uptake. In our investigation, the GNSTM motif conferred protection to peptides over a distance of at least 10 flexible amino acids, and larger spacers may also be feasible. Thus, there may exist a substantial design space for applying this strategy to many peptides of interest to ensure stable expression while avoiding interference with peptide-target interactions, although some optimization is likely to be required. Engineered glycosylation could also be useful for investigating and refining problematic exosome targeting strategies because without such modifications, candidate peptides may fail to enhance exosome uptake due to peptide loss rather than due to problems inherent to the targeting approach.

In addition to protecting N-terminal peptides from degradation, adding the GNSTM motif increased the total amount of Lamp2b fusion protein present in cells and exosomes. This increase could be due to decreased degradation because increasing the glycosylation of Lamp1 and Lamp2 during differentiation of the HL-60 promyelocytic cell line into granulocytes increases the half-life of these proteins (20). However, in this case, the complexity of the oligosaccharides on the proteins was increased, not the number of glycosylation sites. Because Lamp2b is already expected to include 16-20 N-linked glycosylation sites (19), whether adding one additional glycosylation site could increase the half-life of Lamp2b is unclear. Glycosylation also plays a role in the expression and sorting of other exosomal proteins. For example, sorting of the protein EWI-2 into exosomes is dependent on the presence of complex N-linked glycans on this protein (21). Mutation of even one of three N-linked glycosylation sites significantly decreased EWI-2 expression in extracellular vesicles. Furthermore, mutation of all three sites decreased both cellular and vesicle-associated EWI-2 levels. Thus, it is possible that altering the glycosylation of Lamp2b could have similar effects on expression in cells and exosomes.

Previous studies in which targeting peptides were fused to the N terminus of Lamp2b did not report targeting peptide degradation, although these characterizations focused on evaluating whether targeting peptide remained, rather than evaluating whether or not partial targeting peptide degradation occurred (7, 11). Notably, neither of the peptides used in these studies (RVG or internalizing RGD) contains any putative N-linked glycosylation sites that could protect the peptides from degradation. However, in these studies, exosomes were electroporated to load functional cargo molecules, and subsequent investigations have shown that electroporation can cause aggregation of exosomes as well as RNA (22, 23). Thus, it is possible that such aggregates may display different properties than did the exosomes used in our experiments. Furthermore, these prior studies utilized the mouse Lamp2b protein and isolated exosomes from murine dendritic cells, whereas we engineered human Lamp2b and isolated exosomes from human cells (HEK293FT). Thus, differences in protein trafficking and exosome secretion in different species and cell types may result in different susceptibilities of targeting peptides to degradation. Alternatively, any factors leading to increased stability of mouse Lamp2b-based constructs may lead to accumulation of higher levels of Lamp2b in cells and exosomes, such that some pool of intact peptide-Lamp2b escapes proteolytic cleavage prior to exosome secretion. Thus, the strategy proposed here may be especially important for engineering human Lamp2b and human cell-derived exosomes, and whether these benefits may extend to murine exosome engineering remains to be determined.

Because targeting exosomes to specific receptors is required for effective delivery of therapeutic molecules in vivo (7, 11), our strategy for increasing the expression of targeting peptides on exosomes may be particularly useful for translating promising exosome-based therapeutic strategies from preclinical investigations to human trials. Even if mouse Lamp2b could confer enhanced targeting peptide display when expressed in human exosome-producing cells (which remains undetermined), utilizing human Lamp2b is desirable to increase the immune compatibility of exosome-based therapeutics (24). Our strategy for enhancing peptide display via human Lamp2b could also increase peptide display via other exosomal membrane proteins because all such peptide fusions may be susceptible to degradation by endosomal proteases. Given the need for robust technologies for effectively directing exosomes to traffic to specific destinations in vivo, this strategy for enhancing display of targeting peptides could generally enable and enhance exosome-based therapeutics.

REFERENCES 1. van der Meel, R., Fens, M. H., Vader, P., van Solinge, W. W., Eniola-Adefeso, O., and Schiffelers, R. M. (2014) Extracellular vesicles as drug delivery systems: lessons from the liposome field. *J. Control. Release* 195, 72-85
2. Lai, C. P., Mardini, O., Ericsson, M., Prabhakar, S., Maguire, C. A., Chen, J. W., Tannous, B. A., and Breakefield, X. O. (2014) Dynamic biodistribution of extracellular vesicles in vivo using a multimodal imaging reporter. *ACS Nano* 8, 483-4-94
3. Li, X., Li, J. J., Yang, J. Y., Wang, D. S., Zhao, W., Song, W. J., Li, W. M., Wang, J. F., Han, W., Zhang, Z. C., Yu, Y., Cao, D. Y., and Dou, K. F. (2012) Tolerance induction by exosomes from immature dendritic cells and rapamycin in a mouse cardiac allograft model. *PLoS One* 7, e44045
4. Montecalvo, A., Shufesky, W. J., Stolz, D. B., Sullivan, M. G., Wang, Z., Divito, S. J., Papworth, G. D., Watkins, S. C., Robbins, P. D., Larregina, A. T., and Morelli, A. E. (2008) Exosomes as a short-range mechanism to spread alloantigen between dendritic cells during T cell allorecognition. *J. Immunol.* 180, 3081-3090
5. Marcus, M. E., and Leonard, J. N. (2013) FedExosomes: engineering therapeutic biological nanoparticles that truly deliver. *Pharmaceuticals* 6, 659-680
6. E L Andaloussi, S., Mager, I., Breakefield, X. O., and Wood, M. J. (2013) Extracellular vesicles: biology and emerging therapeutic opportunities. *Nat. Rev. Drug Discov.* 12, 347-357
7. Alvarez-Erviti, L., Seow, Y., Yin, H., Betts, C., Lakhal, S., and Wood, M. J. (2011) Delivery of siRNA to the mouse brain by systemic injection of targeted exosomes. *Nat. Biotechnol.* 29, 341-345
8. Ohno, S., Takanashi, M., Sudo, K., Ueda, S., Ishikawa, A., Matsuyama, N., Fujita, K., Mizutani, T., Ohgi, T., Ochiya, T., Gotoh, N., and Kuroda, M. (2013) Systemically injected exosomes targeted to EGFR deliver antitumor microRNA to breast cancer cells. *Mol. Ther.* 21, 185-191
9. Mizrak, A., Bolukbasi, M. F., Ozdener, G. B., Brenner, G. J., Madlener, S., Erkan, E. P., Ströbel, T., Breakefield, X. O., and Saydam, O. (2013) Genetically engineered microvesicles carrying suicide mRNA/protein inhibit schwannoma tumor growth. *Mol. Ther.* 21, 101-108
10. Akao, Y., Iio, A., Itoh, T., Noguchi, S., Itoh, Y., Ohtsuki, Y., and Naoe, T. (2011) Microvesicle-mediated RNA molecule delivery system using monocytes/macrophages. *Mol. Ther.* 19, 395-399
11. Tian, Y., Li, S., Song, J., Ji, T., Zhu, M., Anderson, G. J., Wei, J., and Nie, G. (2014) A doxorubicin delivery platform using engineered natural membrane vesicle exosomes for targeted tumor therapy. *Biomaterials* 35, 2383-2390
12. Sun, D., Zhuang, X., Xiang, X., Liu, Y., Zhang, S., Liu, C., Barnes, S., Grizzle, W., Miller, D., and Zhang, H. G. (2010) A novel nanoparticle drug delivery system: the anti-inflammatory activity of curcumin is enhanced when encapsulated in exosomes. *Mol. Ther.* 18, 1606-1614
13. György, B., Hung, M. E., Breakefield, X. O., and Leonard, J. N. (2015) Therapeutic applications of extracellular vesicles: clinical promise and open questions. *Annu. Rev. Pharmacol. Toxicol.* 55, 439-464
14. Kraft, J. C., Freeling, J. P., Wang, Z., and Ho, R. J. Y. (2014) Emerging research and clinical development trends of liposome and lipid nanoparticle drug delivery systems. *J. Pharm. Sci.* 103, 29-52
15. Zeelenberg, I. S., Ostrowski, M., Krumeich, S., Bobrie, A., Jancic, C., Boissonnas, A., Delcayre, A., Le Pecq, J. B., Combadière, B., Amigorena, S., and Théry, C. (2008) Targeting tumor antigens to secreted membrane vesicles in vivo induces efficient antitumor immune responses. *Cancer Res.* 68, 1228-1235
16. Véron, P., Segura, E., Sugano, G., Amigorena, S., and Théry, C. (2005) Accumulation of MFG-E8/lactadherin on exosomes from immature dendritic cells. *Blood Cells Mol. Dis.* 35, 81-88
17. Bañó-Polo, M., Baldin, F., Tamborero, S., Marti-Renom, M. A., and Mingarro, I. (2011) N-Glycosylation efficiency is determined by the distance to the C-terminus and the amino acid preceding an Asn-Ser-Thr sequon. *Protein Sci.* 20, 179-186
18. van der Vlist, E. J., Nolte-'t Hoen, E. N., Stoorvogel, W., Arkesteijn, G. J., and Wauben, M. H. (2012) Fluorescent labeling of nano-sized vesicles released by cells and subsequent quantitative and qualitative analysis by high-resolution flow cytometry. *Nat. Protoc.* 7, 1311-1326
19. Kundra, R., and Kornfeld, S. (1999) Asparagine-linked oligosaccharides protect Lamp-1 and Lamp-2 from intracellular proteolysis. *J. Biol. Chem.* 274, 31039-31046
20. Lee, N., Wang, W. C., and Fukuda, M. (1990) Granulocytic differentiation of HL-60 cells is associated with increase of poly-N-acetyllactosamine in Asn-linked oligosaccharides attached to human lysosomal membrane glycoproteins. *J. Biol. Chem.* 265, 20476-20487
21. Liang, Y., Eng, W. S., Colquhoun, D. R., Dinglasan, R. R., Graham, D. R., and Mahal, L. K. (2014) Complex N-linked glycans serve as a determinant for exosome/microvesicle cargo recruitment. *J. Biol. Chem.* 289, 32526-32537
22. Hood, J. L., Scott, M. J., and Wickline, S. A. (2014) Maximizing exosome colloidal stability following electroporation. *Anal. Biochem.* 448, 41-49
23. Kooijmans, S. A., Stremersch, S., Braeckmans, K., de Smedt, S. C., Hendrix, A., Wood, M. J., Schiffelers, R. M., Raemdonck, K., and Vader, P. (2013) Electroporation-induced siRNA precipitation obscures the efficiency of siRNA loading into extracellular vesicles. *J. Control. Release* 172, 229-238
24. Neefjes, J., and Ovaa, H. (2013) A peptide's perspective on antigen presentation to the immune system. *Nat. Chem. Biol.* 9, 769-775

In the foregoing description, it will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

Citations to a number of patent and non-patent references are made herein. The cited references are incorporated by reference herein in their entireties. In the event that there is an inconsistency between a definition of a term in the specification as compared to a definition of the term in a cited reference, the term should be interpreted based on the definition in the specification.

We claim:

1. A method of loading an extracellular vesicle with a cargo nucleic acid, the method comprising the steps of:
   expressing within a vesicle-producing cell that contains the cargo nucleic acid (i)
   a fusion protein comprising:
   (i) a nucleic acid-binding domain;
   (ii) a vesicle-targeting domain, and
   (iii) an engineered glycosylation site, wherein the engineered glycosylation site comprises an amino acid sequence that is not naturally present in the fusion protein or any of the components of the fusion protein;
   wherein:
   the cargo nucleic acid includes a binding motif that binds to the nucleic acid-binding domain of the fusion protein, and
   the vesicle-targeting domain of the fusion protein localizes to the extracellular vesicles released by the vesicle-producing cell,
   such that the cargo nucleic acid is loaded into the vesicle when the fusion protein and cargo nucleic acid are both present in by the vesicle-producing cell.

2. The method of claim 1, wherein the vesicle-targeting domain of the fusion protein is a domain of a lysosome-associated protein.

3. The method of claim 2, wherein the lysosome-associated protein is a lysosome-associated membrane protein (LAMP).

4. The method of claim 3, wherein the LAMP comprises a luminal N-terminus and a cytoplasmic C-terminus.

5. The method of claim 3, wherein the nucleic acid-binding domain of the fusion protein comprises a binding domain of a bacteriophage.

6. The method of claim 5, wherein the bacteriophage is a MS2 bacteriophage, a R17 bacteriophage, a lambdoid bacteriophage, a P22 bacteriophage, or a phi21 bacteriophage.

7. The method of claim 1, wherein the vesicle-targeting domain of the fusion protein comprises a sequence selected from a group consisting of SEQ ID NO:23, SEQ ID NO:24, SEQ ID NO:25, SEQ ID NO:27, SEQ ID NO:28, SEQ ID NO:29, SEQ ID NO:31, SEQ ID NO:34, SEQ ID NO:35, and SEQ ID NO:36.

8. The method of claim 1, wherein the vesicle-targeting domain of the fusion protein comprises a sequence having at least 80% amino acid sequence identity to a sequence selected from a group consisting of SEQ ID NO:23, SEQ ID NO:24, SEQ ID NO:25, SEQ ID NO:27, SEQ ID NO:28, SEQ ID NO:29, SEQ ID NO:31, SEQ ID NO:34, SEQ ID NO:35, and SEQ ID NO:36.

9. The method of claim 1, wherein the nucleic acid-binding domain of the fusion protein comprises a binding domain of a bacteriophage.

10. The method of claim 9, wherein the bacteriophage is a MS2 bacteriophage, a R17 bacteriophage, a lambdoid bacteriophage, a P22 bacteriophage, or a phi21 bacteriophage.

11. The method of claim 1, wherein the cargo nucleic acid is an RNA.

12. The method of claim 11, wherein the RNA is a therapeutic RNA.

13. The method of claim 11, wherein the binding motif comprises one or more high affinity binding loops comprising a sequence and structure selected from the group consisting of:

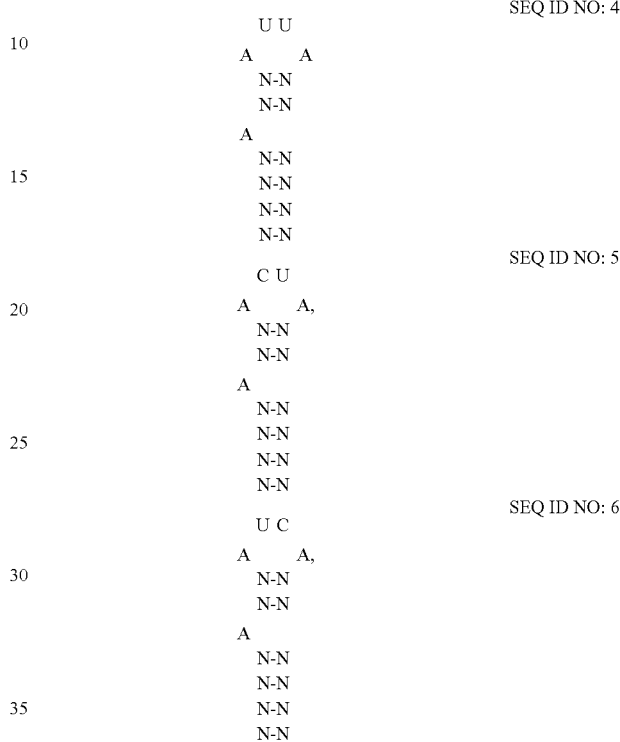

where N—N is any two base-paired RNA nucleotides.

14. The method of claim 1, wherein the vesicle-targeting domain of the fusion protein comprises a domain of a lysosome-associated membrane protein (LAMP), the nucleic acid-binding domain of the fusion protein comprises a binding domain of a bacteriophage, and the cargo nucleic acid is an RNA.

15. The method of claim 1, wherein the vesicle-targeting domain of the fusion protein comprises a sequence selected from a group consisting of SEQ ID NO:23, SEQ ID NO:24, SEQ ID NO:25, SEQ ID NO:27, SEQ ID NO:28, SEQ ID NO:29, SEQ ID NO:31, SEQ ID NO:34, SEQ ID NO:35, and SEQ ID NO:36; the nucleic acid-binding domain of the fusion protein comprises a binding domain of a bacteriophage selected from a group consisting of a MS2 bacteriophage, a R17 bacteriophage, a lambdoid bacteriophage, a P22 bacteriophage, and a phi21 bacteriophage; and the cargo nucleic acid is an RNA.

16. The method of claim 15, wherein the RNA is a therapeutic RNA.

17. The method of claim 15, wherein the binding motif comprises one or more high affinity binding loops comprising a sequence and structure selected from the group consisting of:

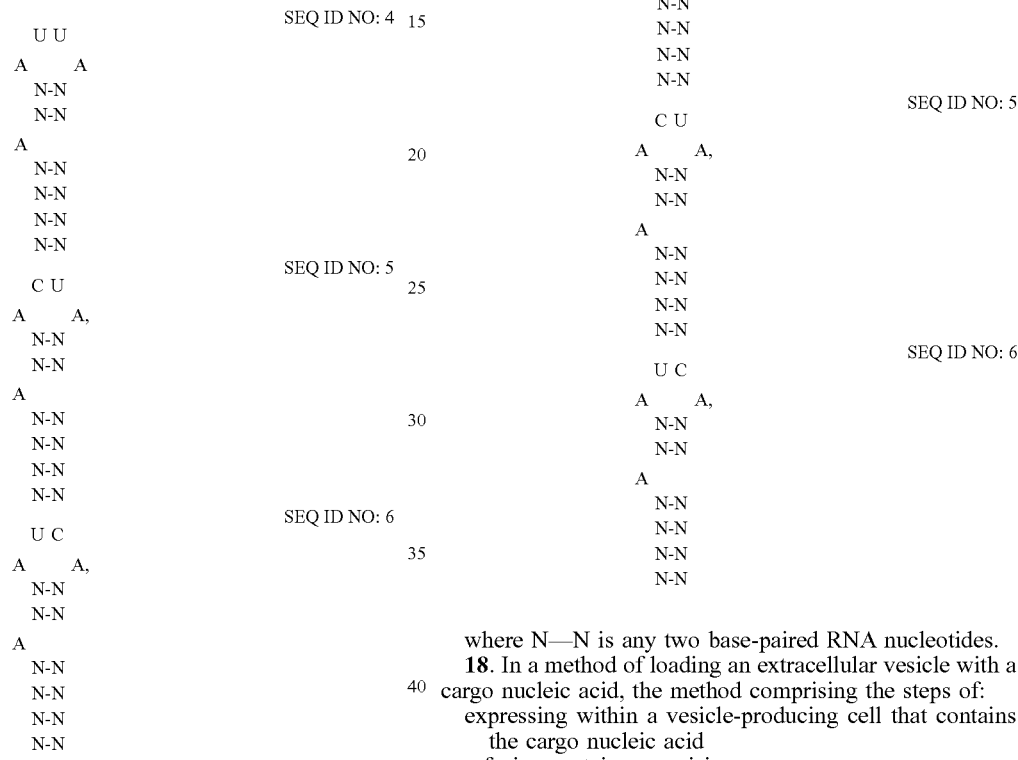

where N—N is any two base-paired RNA nucleotides.

18. In a method of loading an extracellular vesicle with a cargo nucleic acid, the method comprising the steps of:
expressing within a vesicle-producing cell that contains the cargo nucleic acid
a fusion protein comprising:
(i) a nucleic acid-binding domain; and
(ii) a vesicle-targeting domain, and
wherein:
the cargo nucleic acid includes a binding motif that binds to the nucleic acid-binding domain of the fusion protein, and
the vesicle-targeting domain of the fusion protein localizes the extracellular vesicles released by the vesicle-producing cell,
such that the cargo nucleic acid is loaded into the vesicle when the fusion protein and cargo nucleic acid are both present in the vesicle-producing cell;
the improvement that comprises engineering the fusion protein to comprise an engineered glycosylation site, wherein the engineered glycosylation site comprises an amino acid sequence that is not naturally present in the fusion protein or any of the components of the fusion protein.

* * * * *